United States Patent
Dubreuil et al.

(10) Patent No.: US 9,034,873 B2
(45) Date of Patent: May 19, 2015

(54) PYRIDAZINE AND PYRROLE COMPOUNDS, PROCESSES FOR OBTAINING THEM AND USES

(75) Inventors: Didier Max Dubreuil, Port Saint Pere (FR); Muriel Genevieve Pipelier, Nantes (FR); Jean-Paul Pradere, Sautron (FR); Hicham Bakkali, Nantes (FR); Patrice Lepape, Vertou (FR); Thierry Delaunay, Trevoux (FR); Alexandra Tabatchnik, La Baule (FR)

(73) Assignee: Centre National de la Recherche Scientifique (C.N.R.S.), Paris Cedex (FR)

( * ) Notice: Subject to any disclaimer, the term of this patent is extended or adjusted under 35 U.S.C. 154(b) by 977 days.

(21) Appl. No.: 12/309,585

(22) PCT Filed: Jul. 26, 2007

(86) PCT No.: PCT/FR2007/001287
§ 371 (c)(1),
(2), (4) Date: Jan. 23, 2009

(87) PCT Pub. No.: WO2008/012440
PCT Pub. Date: Jan. 31, 2008

(65) Prior Publication Data
US 2010/0298562 A1  Nov. 25, 2010

(30) Foreign Application Priority Data
Jul. 26, 2006 (FR) .................................. 06 06842

(51) Int. Cl.
| | |
|---|---|
| *C07D 213/55* | (2006.01) |
| *C07D 401/04* | (2006.01) |
| *C07D 471/04* | (2006.01) |
| *C07D 401/14* | (2006.01) |
| *C07F 7/22* | (2006.01) |
| *C09B 57/10* | (2006.01) |

(52) U.S. Cl.
CPC ............ *C07D 401/14* (2013.01); *C07D 213/55* (2013.01); *C07D 401/04* (2013.01); *C07D 471/04* (2013.01); *C07F 7/2212* (2013.01); *C09B 57/10* (2013.01)

(58) Field of Classification Search
CPC .. C07D 213/55; C07D 401/04; C07D 471/04; C07D 401/14; C09B 57/10; C07F 7/2212
USPC .......................... 544/238; 514/252.02, 252.03
See application file for complete search history.

(56) References Cited

U.S. PATENT DOCUMENTS

2004/0186288 A1   9/2004 Kruger et al.

OTHER PUBLICATIONS

Jones et. al. (Tetrahedron, 1996, 52(26), pp. 8707-8724).*

(Continued)

Primary Examiner — Susanna Moore
(74) Attorney, Agent, or Firm — Nixon & Vanderhye P.C.

(57) ABSTRACT

The present disclosure describes compounds of the following formula (Ia)

Figure 1:
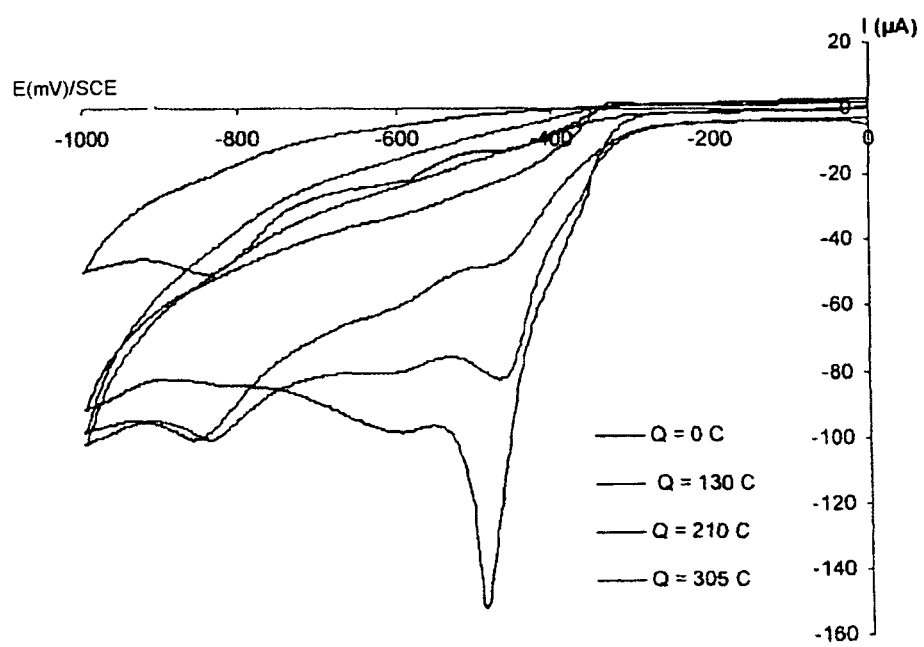

in which:
the groups A, which may be identical or different, represent a group

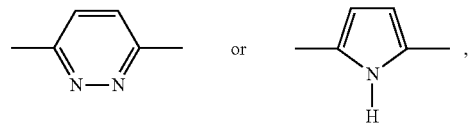

n is an integer equal to 1 or 2,
Y represents an oxygen or sulfur atom, a methylene, hydroxymethylene, carbonyl or thiocarbonyl group, or a group of formula

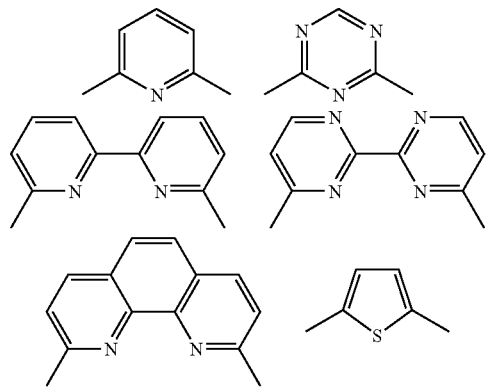

the groups R, which may be identical or different, represent a hydrogen, an alkyl, alkylamine, hydroxyl-alkyl or alkyloxy chain containing from 1 to 6 carbons, or a —COOH, —CONH$_2$, —COOR2 or —CONHR2 group in which R2 is an alkyl chain containing from 1 to 6 carbons, or, when the substituents R are identical in the 2-pyridinyl groups, the substituents R2 may together form an ethereal cyclic alkyl chain, with the exception of the compounds: 2,6-di[5-(2-pyridyl)pyrrol-2-yl]pyridine and bis[5-(6-methyl-2-pyridyl)pyrrol-2-yl]methane.

3 Claims, 12 Drawing Sheets

(56) References Cited

OTHER PUBLICATIONS

Neidle, Stephen, (Cancer Drug Design and Discovery, ed. (Elsevier/Academic Press, 2008) pp. 427-431).*

International Search Report for PCT/FR2007/001287, mailed Apr. 10, 2008.

Jones, R. Alan, et al., "Extended Heterocyclic Systems 1. The Synthesis and Characterisation of Pyrrolylpyridines, Alternating Pyrrole:Pyridine Oligomers and Polymers, and Related Systems", Tetrahedron, vol. 52, No. 26, (Jun. 1996), pp. 8707-8724.

Baxter, Paul N. W., et al., "Self-Assembly and Structure of Interconverting Multinuclear Inorganic Arrays: A [4×5]$Ag^I_{20}$ Grid and an $Ag^I_{10}$ Quadruple Helicate", Chemistry—A European Journal, vol. 6, No. 24, (Dec. 15, 2000), pp. 4510-4517.

Coates, William J., et al., "1,4-Bis(3-oxo-2,3-dihydropyridazin-6-yl)benzene Analogues: Potent Phosphodiesterase Inhibitors and Inodilators", Journal of Medicinal Chemistry, vol. 33, No. 6, (1990), pp. 1735-1741.

* cited by examiner

PYRIDAZINE AND PYRROLE COMPOUNDS, PROCESSES FOR OBTAINING THEM AND USES

This application is the U.S. national phase of International Application No. PCT/FR2007/001287, filed 26 Jul. 2007, which designated the U.S. and claims priority to France Application No. 0606842, filed 26 Jul. 2006, the entire contents of each of which are hereby incorporated by reference.

The present invention relates to nonlinear oligopyridazine compounds, to processes for obtaining them, to the uses thereof, and also to the regression thereof to oligopyrroles and to the uses of the pyridazinylpyrrole and oligopyrrole compounds obtained. The terms "oligopyridazine" and "oligopyrrole" denote compounds comprising a sequence of nitrogenous rings of pyridazine or pyrrole type, said sequence being composed of two symmetrical or nonsymmetrical parts, linked by a heterocyclic spacer group or a heteroatom. In the present application, these terms will in addition be limited to the compounds according to the invention, which have a strictly defined structure.

Since the end of the 1980s, nitrogenous compound coordination chemistry has experienced a rapid development owing to the diversity of the chemical and catalytic properties of organometallic complexes containing one or more nitrogenous functions in their coordination sphere. This diversity is essentially linked to that of the nitrogenous functions involved in these complexes: amine, imine, nitrile, azide, etc.

Coordination chemistry plays a fundamental role in supramolecular chemistry and, in this field, oligopyridines were the first to attract particular attention. Oligopyridines are polydentate ligands which can also be categorized according to the number of nitrogen atoms participating in the chelation of the metal in the complex: bidentates (bipyridines), tridentates (terpyridines), tetradentates (quater-pyridines), etc., having the structure:

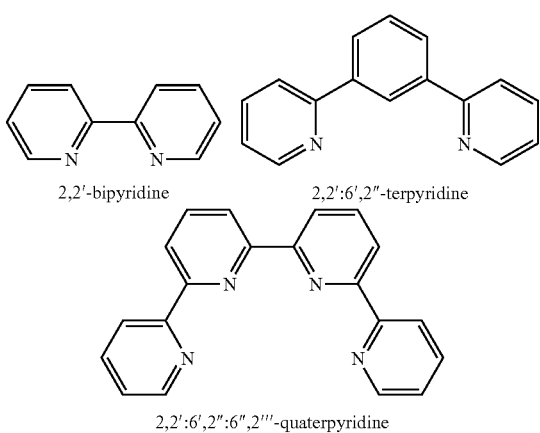

2,2'-bipyridine 2,2':6',2"-terpyridine 2,2':6',2":6",2'''-quaterpyridine 2,2'-Bipyridines have for a long time been the ligands most commonly used in coordination chemistry, in particular when they express asymmetric induction properties linked to the presence of groups which induce a chirality factor. More recently, 2,2':6',2"-terpyridines (tpy) have opened up an area of investigation through the expression of polydentate sites favoring the formation of complexes with transition metals at a higher oxidation state. This property has been exploited, for example, for the oxidation of alcohols and the carbonylation of aromatic compounds. Even more recently, the chemistry of polydentate ligands of this type has been developed for catalytic activation in the context of the decontamination of radioactive waste.

Setting aside heterogeneous structures constituted of pyridine and pyrimidine units, which express a variety of polydentate coordination sites, relatively few studies have related to oligoheterocyclic ligands incorporating diazine units.

Examples of such ligand structures are given below:

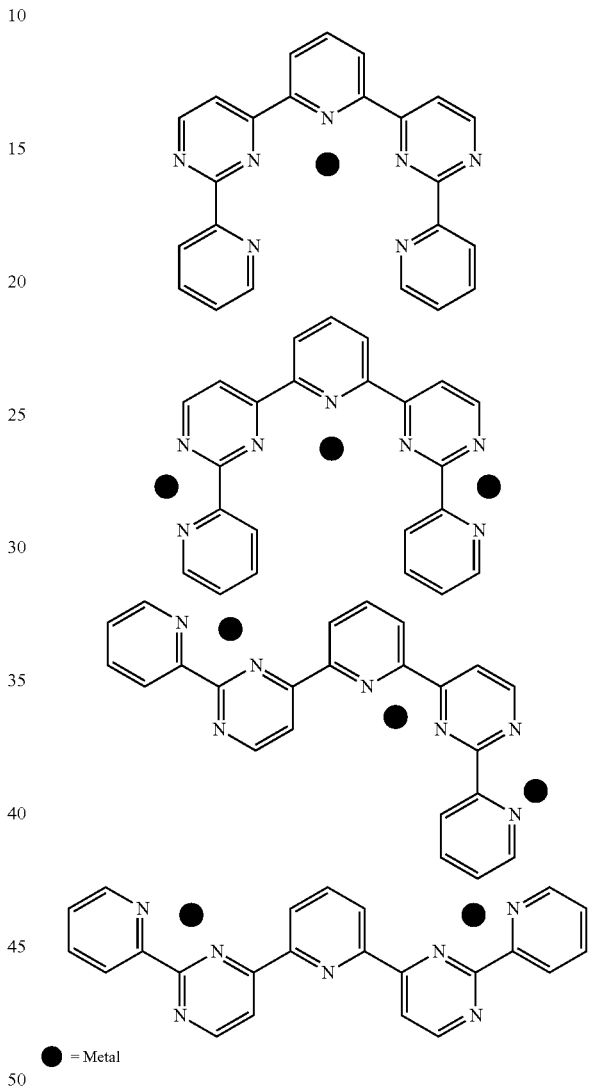

● = Metal

Just like the studies mentioned on the bidentate 3,6-bis (pyridin-2-yl)pyridazine ligands 80 (Hoogenboom, R. et al., Eur. J. Org. Chem., 2003, p. 4887; see scheme below), polydentate ligands based on pyridazine heterocycles have been developed only very recently owing to the fact that the approaches for synthesizing them are tricky, although their potential in the coordination chemistry field now appears to be obvious.

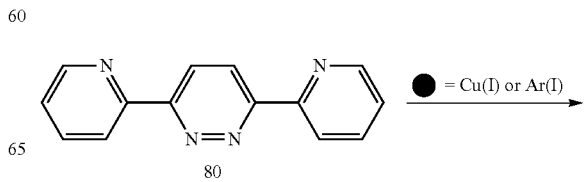

80

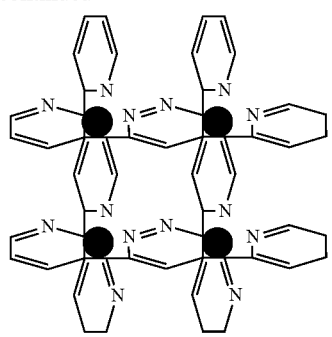

6,6'-Bis(6-methylpyridin-2-yl)-3,3'-bipyridazine 2 has, moreover, shown a strong supramolecular organization potential in the presence of various metals, such as silver (I) (Baxter, P. N. W.; Lehn, J.-M., Fisher, J.; Youinou, M, -T Angew. Chem. 1994, 106, 2432).

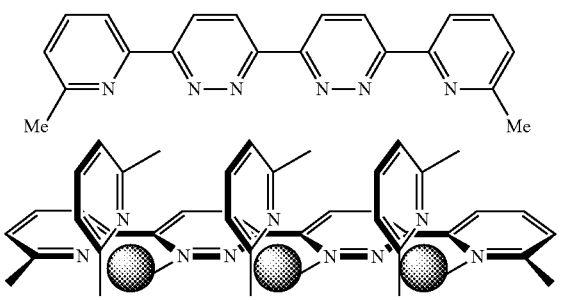

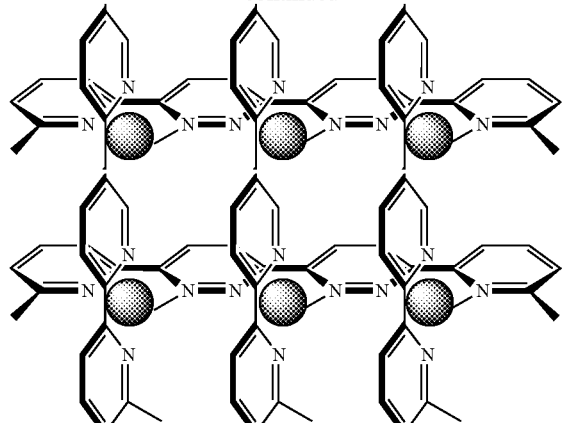

In 2000, the same authors, using reactions for homocoupling halogenated bipyridazines, synthesized a pyridazine tetramer starting from a dichlorobipyridazine precursor 17 (Baxter, P. N. W.; Lehn, J.-M.; Baum, G.; Fenske, D. Chem Eur. J. 2000, 6, 4510).

Like its dimeric homolog, this α,α'-tetrapyridazine ligand has a linear geometry and can therefore only express sequences of coordination sites that are polybidentate for the same molecule. In the presence of silver, this tetramer preferentially results in a supramolecular arrangement of square grid type, as is the case for the bipyridazine 2. However, the elongation of the pyridazine chain also in this case enables self-assembly of four monomers resulting in a helicoidal organization formed of a tetramer in equilibrium with the square grid.

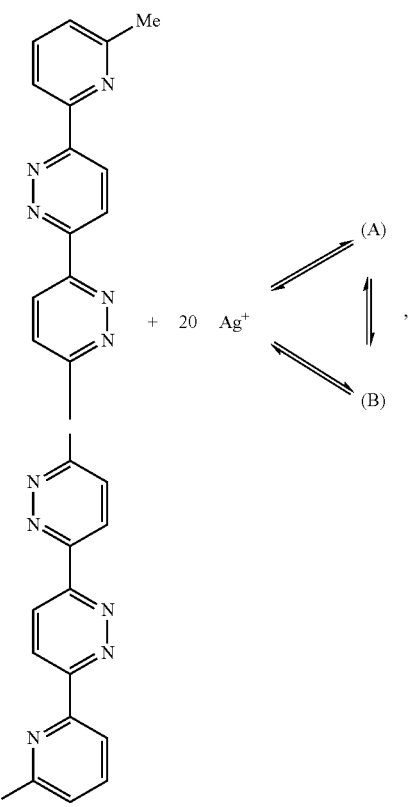

-continued
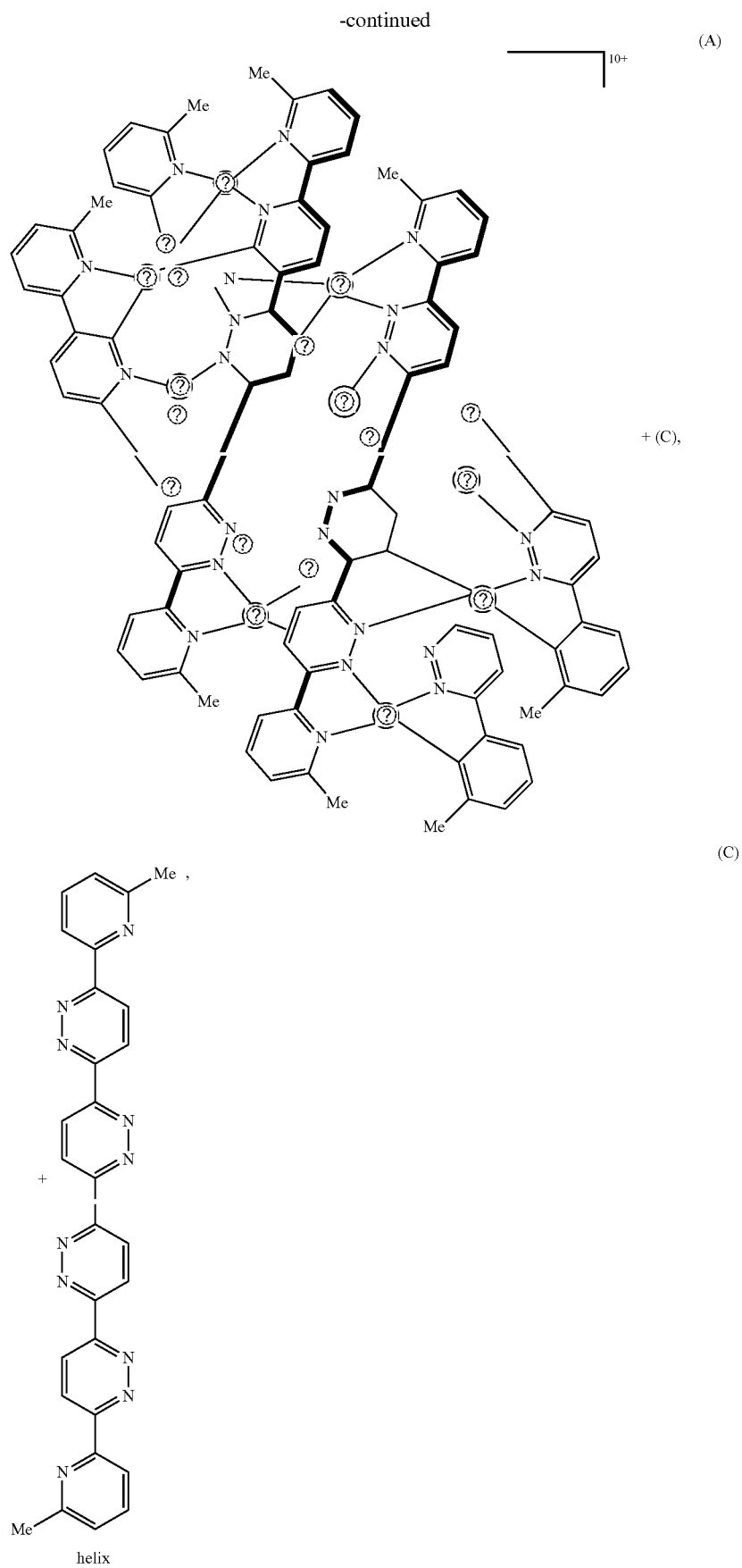

-continued

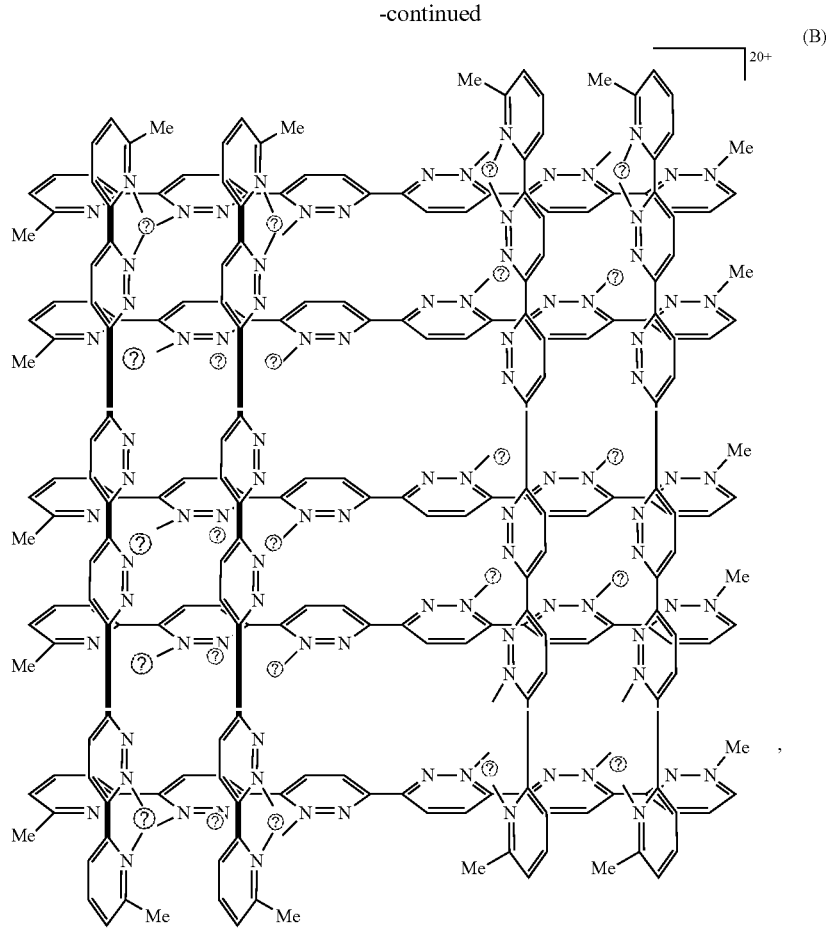

where (A) is helix and (B) is square grid.

In view of the strong potential of the compounds described above and of the absence of a synthetic pathway that can be generalized to these compounds and analogs thereof, of which, moreover, there are few, the inventors decided to attempt to open up the pathway to a new generation of pyridazine and pyrrole ligands.

Now, during prior studies, the inventors had developed a method of electrochemical reduction for reducing monopyridazine compounds to monopyrroles (Manh G. T. et al., Electrochimica Acta, 2002, 2833).

The inventors therefore put forward the premise that it might be possible to carry out an electrochemical reduction of oligopyridazine compounds under conditions to be determined, despite the presence of several pyridazine rings within the same molecule, said rings being capable of considerably modifying its structure and its electronic properties.

In order to validate this premise the inventors had to, in a first step, develop pathways for synthesizing the oligopyridazine compounds.

In a second step, the reduction of the pyridazine sequences to oligopyrroles could be attempted. Unexpectedly, this reduction is not only effective under specific conditions developed and optimized by the inventors, but, in addition, it does not produce cyclization between the pyridazine residues or any other potential side reactions. Furthermore, the reduction may also take place pyridazine ring by pyridazine ring, making it possible to obtain just one or several site(s) of reduction on the molecule, thus opening up the route to the preparation of mixed pyridazinylpyrrole compounds.

The inventors also sought to identify the potential biological applications of these new compounds. These compounds were then found to have therapeutic properties of great interest, in particular antiparasitic, anticancer and antibacterial properties.

The present invention therefore relates to nonlinear oligopyridazine compounds, to the processes for obtaining them, to the uses thereof, and also to the reduction thereof to oligopyrroles and to the uses of the pyridazinylpyrrole and oligopyrrole compounds obtained.

According to a first aspect, the invention relates to compounds of formula

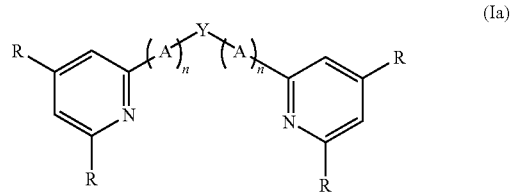

(Ia)

in which:
the groups A, which may be identical or different, represent a group

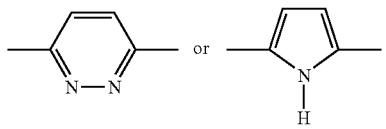

n is an integer equal to 1 or 2,
Y represents an oxygen or sulfur atom, a methylene, hydroxymethylene, carbonyl or thiocarbonyl group, or a group of formula

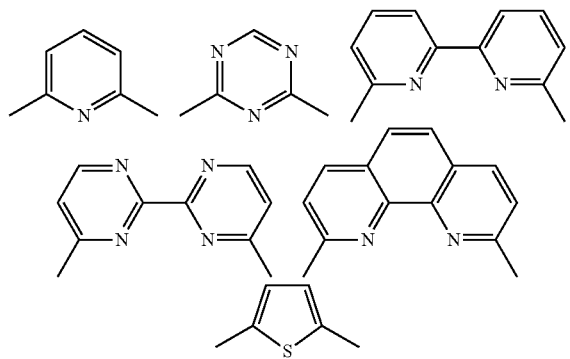

the groups R, which may be identical or different, represent a hydrogen, an alkyl, alkylamine, hydroxyalkyl or alkyloxy chain containing from 1 to 6 carbons, or a —COOH, —CONH$_2$, —COOR2 or —CONHR2 group in which R2 is an alkyl chain containing from 1 to 6 carbons, or, when the substituents R are identical in the 2-pyridinyl groups, the substituents R2 may together form an ethereal cyclic alkyl chain, with the exception of the compounds:
2,6-di[5-(2-pyridyl)pyrrol-2-yl]pyridine,
bis[5-(6-methyl-2-pyridyl)pyrrol-2-yl]methane.

Preferably, the alkyl, alkylamine, hydroxyalkyl and alkyloxy chains are methyls, methylamines, hydroxymethyls and methoxy, and the ethereal cyclic chain is of —CH$_2$H$_5$—(O—C$_2$H$_5$—)$_p$ type, it being possible for p to be between 1 and 4, limits included.

Advantageously, Y will represent an oxygen or sulfur atom or a group of formula

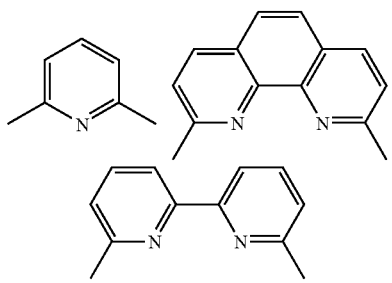

and the groups R, which may be identical or different, will represent a hydrogen, an alkyl or alkyloxy chain containing from 1 to 6 carbons, or a —COOH or —COOR2 group, in which R2 is an alkyl chain containing from 1 to 6 carbons.

The preferred compounds of the invention are more particularly those listed below:
2,9-bis[5-(pyridin-2-yl)pyrrol-2-yl]-1,10-phenanthroline,
2,6-bis[5-(pyridin-2-yl)pyrrol-2-yl]pyridine,
2,6-bis[5-(6-methylpyridin-2-yl)pyrrol-2-yl]-pyridine,
di(6-pyridin-2-yl)pyridazine ether,
di(6-pyridin-2-yl)pyridazine thioether,
2,6-bis[6-(pyridin-2-yl)pyridazin-3-yl]-pyridine,
2,6-bis[6-(6-methylpyridin-2-yl)pyridazin-3-yl]pyridine,
2,6-bis[3-(2-carboxypyridin-6-yl)pyridazin-6-yl]pyridine,
6,6'-bis[6-(pyridin-2-yl)pyridazin-3-yl]-2,2'-bipyridine,
2,9-bis[6-(pyridin-2-yl)pyridazin-3-yl]-1,10-phenanthroline,
2,6-bis[6-(6-methylpyridin-2-yl)pyridazin-3-yl]-2,2'-bipyridine,
2,6-bis[5-(6-methylpyridin-2-yl)pyrrol-2-yl]-2,2'-bipyridine,
6,6'-bis[5-(pyridin-2-yl)pyrrol-2-yl]-2,2'-bipyridine
2,9-bis[6-(6-methylpyridin-2-yl)pyridazin-3-yl]-1,10-phenanthroline,
2,9-bis[5-(6-methylpyridin-2-yl)pyrrol-2-yl]-1,10-phenanthroline.

In order to prepare these compounds, the inventors had to firstly synthesize an entire series of precursors.

According to a second aspect of the invention, the latter is directed toward precursors of the compounds according to the invention, in particular the compounds of formula

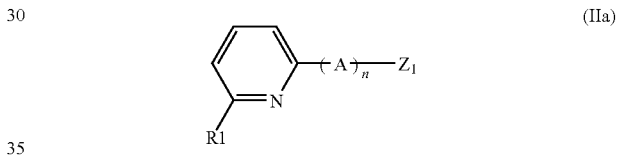

(IIa)

in which:
when n is an integer equal to 1,
A represents a group

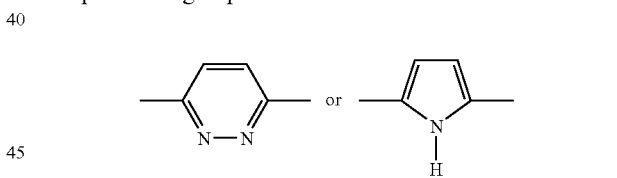

R1 represents a hydrogen, or an alkyl or alkyloxy chain containing from 1 to 6 carbons,
Z$_1$ represents a mercapto group or an SnE$_3$ group, in which E represents a methyl, butyl or phenyl chain, or,
when n is an integer equal to 2,
the groups A, which may be identical or different, represent a group

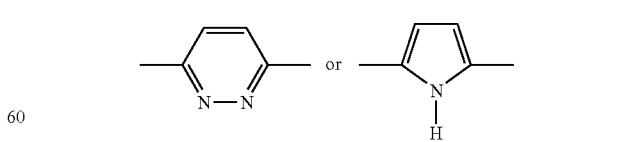

R1 represents a hydrogen, or an alkyl or alkyloxy chain containing from 1 to 6 carbons,
Z$_1$ represents a halogen, an alkyl or alkyloxy chain containing from 1 to 6 carbons, or a hydroxyl, mercapto or SnE$_3$ group, in which E is as defined above, with the exception of 3-chloro-6-[6-(6-methylpyridin-2-yl)pyridazin-3-yl]pyridazine.

Preferably, the precursors will have identical groups A, and $Z_1$ will represent a halogen or alkoxy, an $SnE_3$ group, a hydroxyl or a mercapto.

These precursor compounds were themselves prepared by means of processes developed by the inventors. According to a third aspect, the invention relates to processes for preparing said precursors.

A first process for preparing the precursors makes it possible to prepare the compounds of general formula

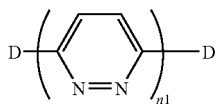

(XIX)

in which the groups D represent a halogen or an alkyloxy chain containing from 1 to 6 carbons, preferably methoxy or ethoxy, and n1 is an integer between 2 and 4, limits included, by coupling at least two halopyridazines of formula

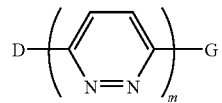

(XX)

in which G represents a halogen, D is as defined above, and m is an integer between 1 and 3, limits included, in the presence of a stoichiometric mixture of zinc, dibromobis(triphenylphosphine)nickel and tetrabutylammonium iodide in distilled and degassed dimethylformamide, the coupling being followed by a step of purification by decomplexation.

The functions which react during this coupling are the halogen functions.

These reactions are carried out at between 50 and 60° C. approximately.

This process has the advantage of allowing the incrementation of the number of pyridazine rings in the molecule.

The purification step is necessary in order to decomplex the product of the reaction from the reaction medium. This purification process can be carried out according to two distinct procedures:

According to a first procedure, the process for purifying the compounds is carried out by decomplexation of said compounds in a saturated aqueous solution of potassium cyanide or sodium cyanide under cold conditions for approximately 1 h 30 to 4 h, preferably about 2 h to 3 h.

The expression "under cold conditions" is intended to mean temperatures ranging from 0 to 25° C. approximately, preferably about 18 to 20° C.

According to a second procedure, the process for purifying the compounds is carried out by decomplexation of said compounds in a saturated aqueous solution of potassium halide or tetrabutylammonium halide, preferably potassium fluoride, or in a saturated aqueous solution of ammonia, the organic phase subsequently being washed with sodium hydrogen carbonate or potassium hydrogen carbonate, and then extracted with chloroform, dichloromethane, ethyl acetate or ether, etc.

A second process for preparing the precursors makes it possible to prepare the compounds of general formula

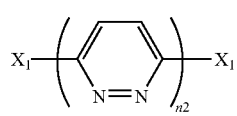

(XXIa)

in which n2 is an integer between 1 and 4, limits included, and the groups $X_1$, which may be identical or different, represent an alkyl or alkyloxy chain containing from 1 to 6 carbons, or a group chosen from the following groups:

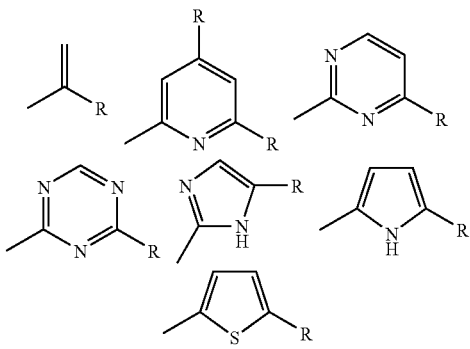

in which R represents a hydrogen, an alkyl or alkyloxy chain containing from 1 to 6 carbons, or a phenyl.

This process implements Stille coupling, in proportions ranging from 1:2 to 1:3, between a compound of formula

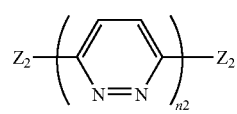

(XXII)

and a compound of formula $$X_1—Z_3$$

in which $Z_2$ and $Z_3$, which different, represent either a halogen, or a stannyl group of formula $SnE_3$, in which E represents a methyl, butyl or phenyl chain, and $X_1$ is as defined above in relation to formula (XXIa).

This process enables coupling of the end groups on the oligopyridazine compounds.

As an alternative to these synthetic processes which are purely organic in nature, the inventors also developed processes using electrochemical synthesis pathways.

The inventors therefore propose a process for electrochemical homocoupling of a pyridazine halide of formula

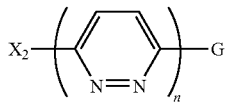

(XXIIIa)

in which n is equal to 1 or 2, G is a halogen and $X_2$ represents a halogen, an alkyl or alkyloxy chain containing from 1 to 6 carbons, or a group chosen from the following groups:

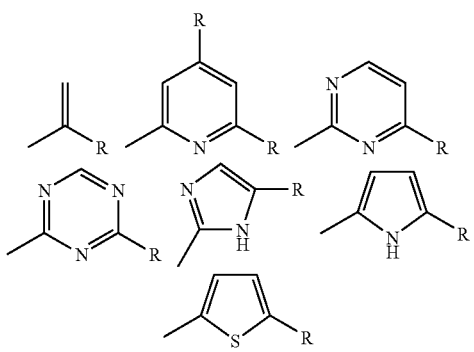

in which R represents a hydrogen, an alkyl or alkyloxy chain containing from 1 to 6 carbons, or a phenyl, the electrolysis conditions being the following:

the anode is constituted of at least 50% iron, the electrolysis medium comprises nickel, an element chosen from halogens, and pyridine or its derivatives.

Preferably, the anode used is an Fe/Ni (64/36) anode. The reaction solvent advantageously comprises at least 50% of DMF and a polar cosolvent. For example, use may be made of a mixture of dimethylformamide (DMF) and of pyridine, in a ratio ranging from 90/10 to 50/50, limits included, preferably 80/20. The catalyst used is preferably a nickel complex, such as a nickel halide hydrate. When the solvent does not contain pyridine, a nickel halide-bipyridine complex may advantageously be used as catalyst.

The support electrolyte is preferably a tetrabutylammonium halide or an equivalent such as tetrabutylammonium tetrafluoroborate, advantageously in amounts ranging from approximately 10 to 20 mol %, limits included, preferably 13 to 17%, relative to the pyridazine substrate.

The intensity used during the reaction is, for example, about 0.05 A to 0.2 A, limits included, preferably 0.06 A to 0.1 A. The reaction may be carried out at ambient temperature (about 18-25° C.).

Moreover, the inventors also propose a process for electrochemically heterocoupling a pyridazine halide of formula

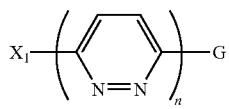

(XXIIIb)

in which n is an integer equal to 1 or 2, G is a halogen and G represents an alkyl or alkyloxy chain containing from 1 to 6 carbons, or a group chosen from the following groups:

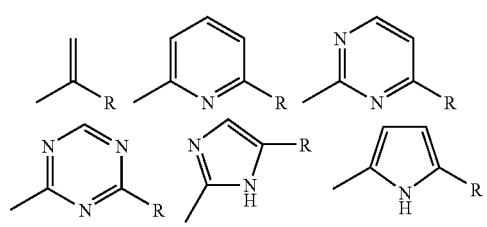

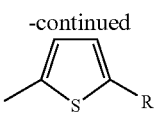

in which R represents a hydrogen, or an alkyl or alkyloxy chain containing from 1 to 6 carbons, with an aromatic ring halide of formula Ar-G, in which $X_1$ is as defined above and Ar represents an optionally substituted, 5- or 6-membered aromatic ring, the electrolysis conditions being the following:

the anode is constituted of iron, the catalyst is chosen from nickel halide-bipyridine complexes.

Preferably, the solvent used is DMF, while the support electrolyte is a tetrabutylammonium halide or an equivalent such as tetrabutylammonium tetrafluoroborate in amounts ranging from approximately 10 to 20 mol %, limits included, preferably from 13 to 17%, relative to the pyridazine substrate. The intensity used during the reaction is from 0.15 to 0.35 A, limits included, preferably about 0.2 A. The reaction may be carried out at ambient temperature (about 18-25° C.)

The aromatic ring is preferably a phenyl, pyridinyl or thiophenyl nucleus, which is optionally monosubstituted.

The compound of formula

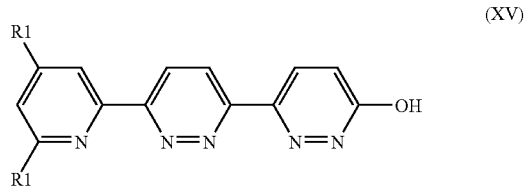

(XV)

in which the groups R1, which may be identical or different, represent a hydrogen, or an alkyl or alkyloxy chain containing from 1 to 6 carbons is obtained by hydrolysis of the compound of formula

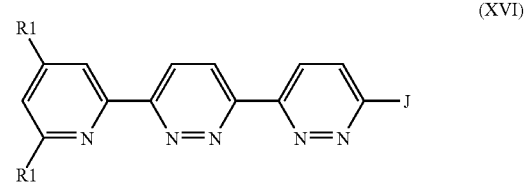

(XVI)

in which J represents a halogen or a methoxy.

In addition to the processes described above, the compounds of formula (XV) may alternatively be prepared starting from 3-acetyl-6-(pyridin-2-yl)pyridazine, itself obtained starting from 3-chloro-6-(pyridin-2-yl)pyridazine. To this effect, glyoxylic acid is then condensed with 3-acetyl-6-(pyridin-2-yl)pyridazine in the presence of potassium carbonate, and then the resulting intermediate is treated in an acetic acid medium and in the presence of hydrazine monohydrate.

The compounds of formula

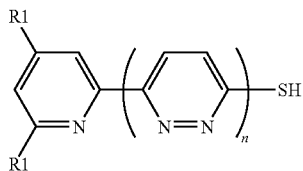
(XVII)

in which n is an integer equal to 1 or 2, and the groups R1, which may be identical or different, represent a hydrogen or an alkyl or alkyloxy chain containing from 1 to 6 carbons, are obtained by reacting phosphorus pentasulfide with the compound of formula

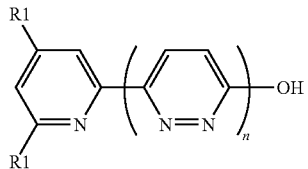
(XVIII)

The invention is also directed toward the process for preparing the compounds of formula

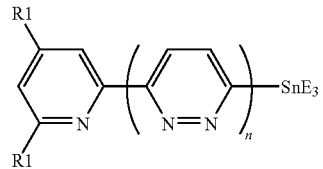
(IXa)

in which the groups R1, which may be identical or different, represent a hydrogen or an alkyl or alkyloxy chain containing from 1 to 6 carbons, and E represents a methyl, butyl or phenyl chain, by reacting the halogenated precursor with the corresponding hexaalkyl distannate in the presence of palladium(0) at a temperature of 90-110° C.

Another precursor of interest synthesized by the inventors is 6,6'-bis(tributylstannyl)-2,2'-bipyridine. This compound is obtained by reacting 6,6'-dihalo-2,2-bipyridine with hexabutyl distannate in the presence of palladium(0) at a temperature of approximately 90-110° C. 6,6'-Dihalo-2,2'-bipyridine has been described in Nakhmanovich et al., *Synthetic metal,* 1997, 84: 883-884.

Two other precursors of interest are, moreover, described in the example section and also exhibit biological activities. They are 2,6-bis(3-oxo-2H-pyridazin-6-yl)pyridine and 2,6-bis(3-chloropyridazin-6-yl)pyridine.

Finally, the pyrrole precursors may be obtained by reduction, to pyrroles, of the corresponding pyridazine compounds.

It involves in particular the following process, implementing the reduction, to pyrrole, of a compound of formula

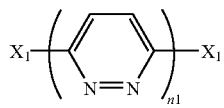
(XXIb)

in which n1 is an integer between 2 and 4, limits included, and the $X_1$ groups, which may be identical or different, represent an alkyl or alkyloxy chain containing from 1 to 6 carbons or a group chosen from the following groups:

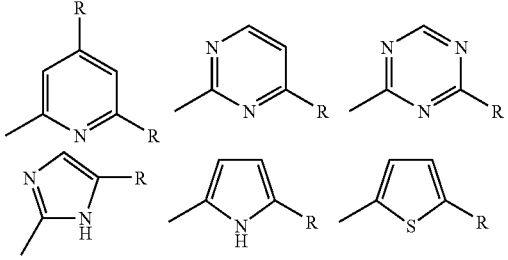

in which R represents a hydrogen, an alkyl or alkyloxy chain containing from 1 to 6 carbons, or a phenyl, electrochemically, by extrusion of a nitrogen atom on one or more pyridazine ring(s), in which the electrolysis conditions are the following:
the anode is a large-area electrode,
the electrolysis medium is a proton-donating polar medium.

Some of the processes described above, although not claimed in the present application, are, however, novel and form the subject of a co-filing.

The precursors having been prepared, the compounds according to the invention can be synthesized. According to a fourth aspect of the invention, the latter is directed toward the processes for preparing the compounds according to the invention using the precursors described above.

The invention thus proposes, in particular, a process for preparing the compounds of the formula

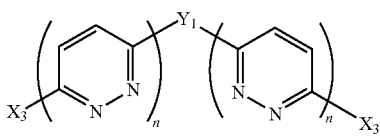
(IIIa)

in which:
n is an integer equal to 1 or 2,
$Y_1$ represents an oxygen or a sulfur,
the groups $X_3$, which may be identical or different, represent a hydrogen or a substituent of formula

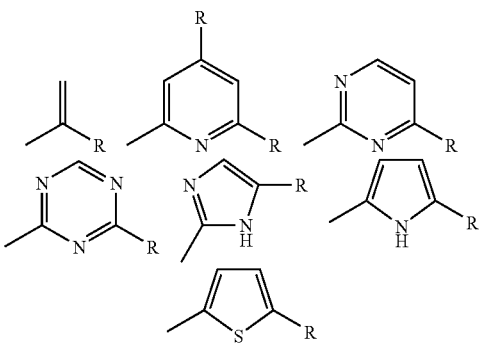

in which the groups R, which may be identical or different, represent a hydrogen or an alkyl or alkyloxy chain containing from 1 to 6 carbons, by coupling, in the presence of a strong base, between a compound of formula

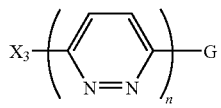  (IVa)

and a compound of formula

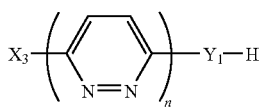  (V)

in which $Y_1$, $X_3$ and n are as defined above, and G represents a halogen.

The reaction temperature is preferably between 80-110° C., limits included. Advantageously, the following strong bases will be used: NaH, NaOH, and as solvent, DMF or DMSO.

More particularly, the process according to the invention makes it possible to prepare the compounds of formula

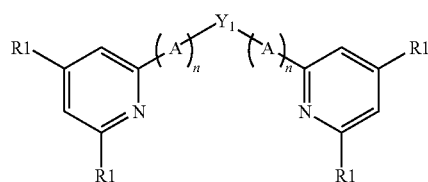  (VI)

in which:
the groups A, which may be identical or different, represent a group

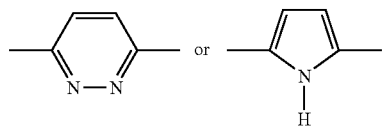

$Y_1$ represents an oxygen or a sulfur,
n is an integer equal to 1 or 2,
the groups R1, which may be identical or different, represent a hydrogen or an alkyl or alkyloxy chain containing from 1 to 6 carbons,
by coupling, in the presence of a strong base, between a compound of formula

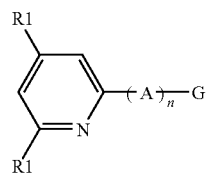  (IIb)

and a compound of formula

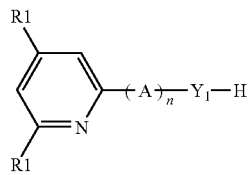  (VII)

in which A, $Y_1$, n and R1 are as defined above and G represents a halogen.

Preferably, the groups A are identical.

The invention also proposes a process for preparing the compounds of formula

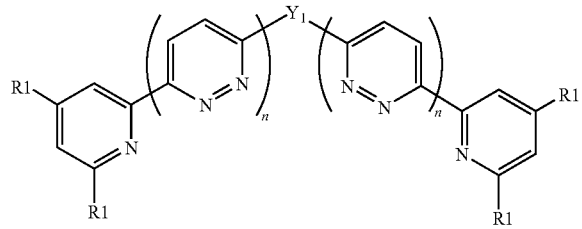  (IIIb)

in which:
$Y_2$ represents a group of formula

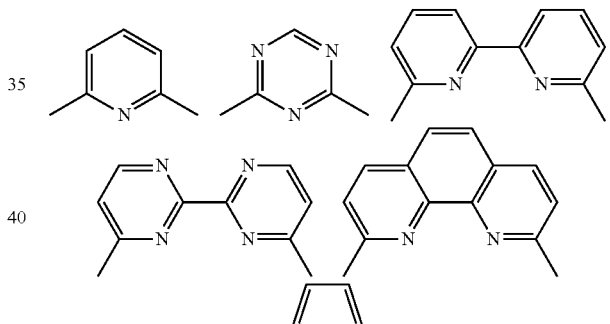

n is an integer equal to 1 or 2,
the groups R1, which may be identical or different, represent a hydrogen or an alkyl or alkyloxy chain containing from 1 to 6 carbons,
by Stille coupling between a compound of formula

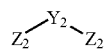  (VIII)

and at least one compound of formula

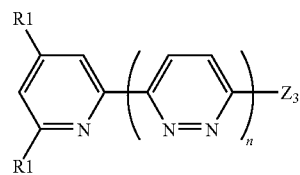  (IXb)

$Z_2$ and $Z_3$ representing either a halogen, or a stannylated group of formula $SnE_3$, in which E represents a methyl, butyl or phenyl chain, and $Y_2$, R1 and n being as defined above.

More specifically, the invention proposes a process for preparing the compounds of formula

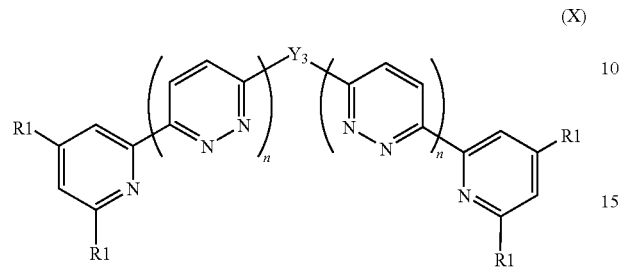

(X)

in which:
$Y_3$ represents a methylene, hydroxymethylene, carbonyl or thiocarbonyl group,
n is an integer equal to 1 or 2,
the groups R1, which may be identical or different, represent a hydrogen or an alkyl or alkyloxy chain containing from 1 to 6 carbons,
by coupling two organomagnesium or organocuprate compounds of formula

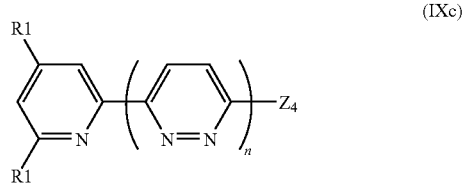

(IXc)

in which $Z_4$ represents MgG or Cu, G being a halogen, in the presence of methyl formate, of carbonyldiimidazole or of thiocarbonyldiimidazole.

The obtaining of the organomagnesium and organocuprate derivatives is well known to those skilled in the art. The conventional reaction uses the halogenated compound corresponding to the desired organomagnesium-/organocuprate compound. The insertion of the magnesium or of the copper into the compound is carried out by addition of magnesium or of copper halide (CuI, CuCl) to the reaction medium, in the presence of a solvent such as, for example, $Et_2O$ or THF.

Some of the reactions described above are sometimes limited to a few quite specific substituents. The other functions claimed can be obtained by means of reactions well known to those skilled in the art. By way of example, mention will be made of the obtaining of a carbonyl function by oxidation of a methyl substituent.

The following molecule

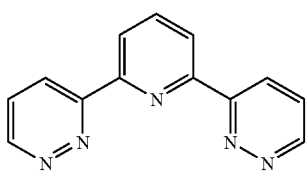 [SMILES: c1cnnc(-c2cccc(-c3cccnn3)n2)c1]

was prepared by the inventors according to a novel multistep synthetic pathway.

In a first step, the compound of formula

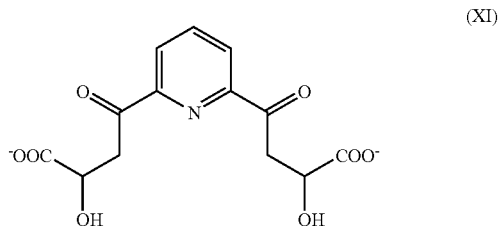

(XI)

is prepared by condensation-aldolization, in a basic medium, of glyoxylic acid with the compound of formula

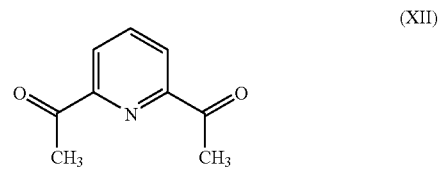

(XII)

This reaction preferentially uses two equivalents of glyoxylic acid. Advantageously, the base may be chosen from potassium carbonate or potassium hydroxide. This reaction is preferably carried out at ambient temperature (about 18-25° C.).

According to a second step, the compound of formula

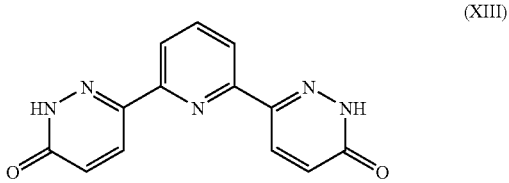 [SMILES: O=c1ccc(-c2cccc(-c3ccc(=O)[nH]n3)n2)n[nH]1]

(XIII)

is obtained by addition of hydrazine at reflux in an acidic medium, preferably acetic acid, and then cyclization-dehydration of a 4,4'-(pyridin-2,6-yl)bis(2-dihydroxy-4-dioxo) butanoate salt.

According to a third step, 2,6-bis(6-halopyridazin-3-yl) pyridine is obtained by halogenation, with phosphorus oxyhalide, of the 2,6-bis(6-2H-pyridazin-3-one)pyridine compound. This reaction is advantageously carried out at a temperature of about 80 to 110° C.

Finally, 2,6-bis(pyridazin-3-yl)pyridine is prepared by reduction of the halogen functions of the 2,6-bis(6-halopyridazin-3-yl)pyridine, by catalytic hydrogenation.

The latter reaction is catalyzed by palladium-on-charcoal, under a dihydrogen atmosphere. Advantageously, ethanol will be used as solvent. This reaction can be carried out at ambient temperature.

The invention is also directed toward a process for condensation-aldolization, in a basic medium, of glyoxylic acid with the compound of formula

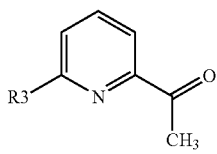
(XIV)

in which R3 represents a hydrogen, an alkyl chain containing from 1 to 6 carbons, or a —COCH$_3$ group, characterized in that the base used is potassium carbonate, introduced in an amount of at least three equivalents of said carbonate relative to the compound of formula (XIV).

Depending on the nature of the substituent R3, 1 or 2 equivalents of glyoxylic acid will be introduced into the medium. Advantageously, the weak bases may be chosen from calcium carbonate or potassium carbonate.

The reaction can be carried out at ambient temperature.

The invention also proposes a process for preparing a compound

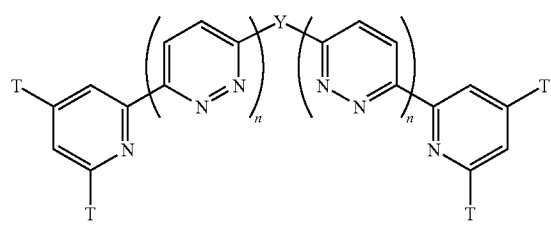
(XXIX)

in which:
n is an integer equal to 1 or 2,
Y represents an oxygen or sulfur atom, a methylene, hydroxymethylene, carbonyl or thiocarbonyl group or a group of formula

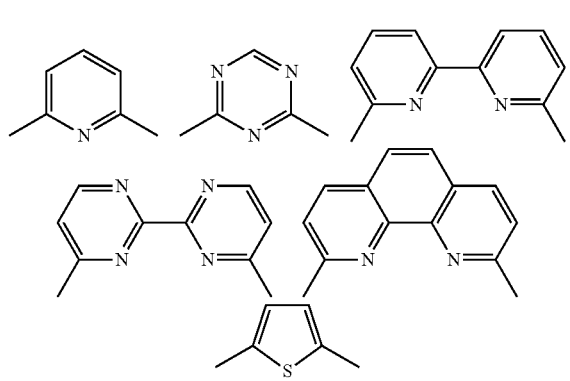

the groups T, which may be identical or different, represent a hydrogen or an alkyl chain containing from 1 to 6 carbons, by coupling between a compound of formula

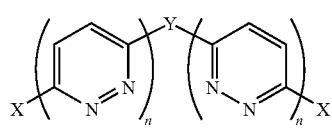
(XXX)

in which the groups X, which are identical, are a halogen, and Y and n are as defined above, and a compound of formula

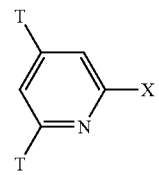
(XXXI)

in which X and T are as defined above, in the presence of butyllithium, of a solvent, of a zinc reactant and of palladium (0).

Advantageously, the solvent will be THF or ether, the zinc reactant will be ZnCl$_2$ and the palladium(0) will be (Pd(Ph$_3$)$_4$) or palladium dibenzylidene acetone (Pd$_2$dba$_3$).

According to a fifth aspect of the invention, the latter relates to a process for reducing the oligopyridazines according to the invention to oligopyrroles.

The process therefore makes it possible to reduce, to pyrrole(s), the compounds of formula

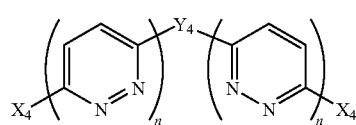
(IIIc)

in which:
Y$_4$ represents a methylene group or a group of formula

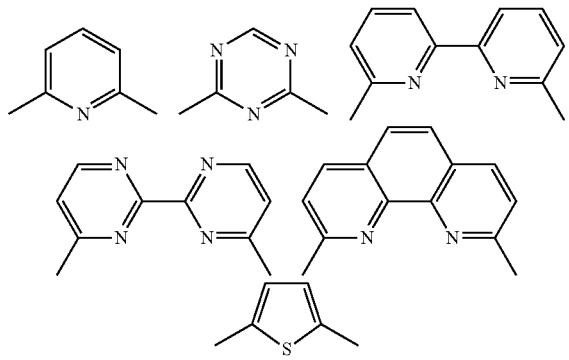

n is an integer equal to 1 or 2,
the groups X$_4$, which may be identical or different, represent a hydrogen, a hydroxyl or mercapto group or a substituent of formula

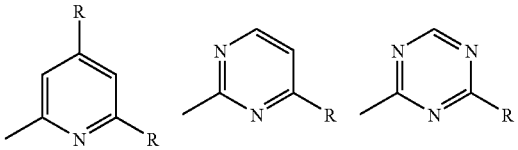

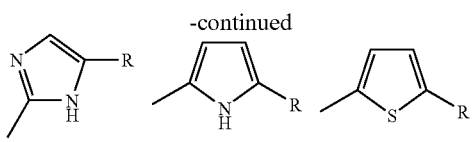

in which the groups R, which may be identical or different, represent a hydrogen, an alkyl or alkyloxy chain containing from 1 to 6 carbons, or a phenyl, electrochemically, by extrusion of a nitrogen atom on one or more pyridazine ring(s), the electrolysis conditions being the following:
the anode is a large-area electrode,
the electrolysis medium is a proton-donating polar medium.
Preferably, $Y_4$ represents

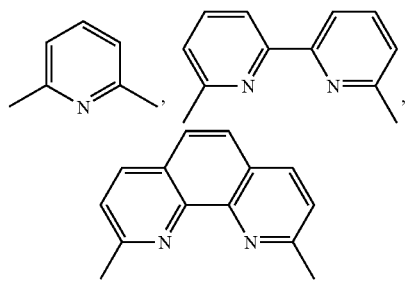

and the groups $X_4$, which may be identical or different, represent a hydrogen, a hydroxyl or a substituent of formula

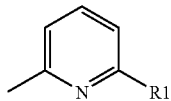

in which R1 is a methyl or a methoxy.

By way of example, the proton-donating polar medium may be constituted of an organic polar solvent (such as DMF, acetonitrile, etc.) supplemented with a proton donor (such as phenol, acetic acid, etc.), and, optionally, when the resulting medium is not conductive, a support electrolyte such as quaternary ammonium salts or an alcoholic acid aqueous medium.

Advantageously, the quaternary ammonium salts are chosen from tetrabutylammonium hexafluorophosphate or tetrabutylammonium hydrogen sulfate, and the alcoholic acidic medium is constituted of a mixture of sulfuric acid or acetic acid to which ethanol has been added.

Preferably, the cathode is chosen from mercury film electrodes 4.5 cm in diameter, large-area carbon electrodes or screen-printed carbon electrodes.

The intensity used is about 10 to 50 mA. The reaction is carried out at ambient temperature (about 18-25° C.)

The reduction potential imposed, which varies according to the substrates studied, should be controlled in order to control the Coulomb amount consumed during the electrolysis, i.e. the number of electrons used: 4 for monopyrrole and 8 for bipyrrole, etc.

This process completes the studies by the inventors on the reduction of a pyridazine ring to pyrrole (Manh G. T. et al, *Electrochimica Acta*, 2002, 2833).

Unexpectedly, this electrochemical reduction effective on monopyridazines was also found to be applicable, after development of the appropriate reaction conditions, to oligopyridazine compounds.

In fact, it was not easy to obtain regression of the pyridazine rings, owing to the modification of the electronic environment of the rings, this modification being mainly due to the fact that the pyridazine rings that had to react were in a different electronic environment linked to the presence of rings in their respective surroundings. In addition, this modification was also capable of generating synthesis intermediates having different electroreduction properties. Furthermore, in the case where the regression could be carried out, it was probable that the electrochemical reduction steps, performed simultaneously on several pyridazine structures close to one another, interact with one another and result, for example, in degradations, internal rearrangements, and partial reductions so as to give di- or tetrahydropyridazine intermediates in place of the pyrrole sequences. In the case where the regression was found to be sequential (pyridazine ring by pyridazine ring), it was a question of evaluating the influence of the possible formation of a first pyrrole or of a dihydropyridazine intermediate on the reduction potential of the mixed systems then generated.

The term "regression" is intended to mean two steps of reduction in an acidic medium, the regression being the mechanistic result of the electrochemical reductions.

The studies by the inventors made it possible to establish a protocol suitable for the reduction of oligopyridazine compounds and to demonstrate the nature of this reduction, either sequential or simultaneous depending on the number of electrons, and the potential applied during the electroreduction.

In all the processes above, reference has been made to alkyl and alkyloxy chains containing 1 to 6 carbons. Advantageously, said chains contain 1 to 3 carbons, they are preferably methyl, ethyl, methoxy or ethoxy.

According to a sixth aspect, the invention aims to cover the multiple uses of the compounds synthesized.

The compounds according to the invention are particularly suitable for use as ligands.

The term "compound according to the invention" is intended to mean the compounds of formula

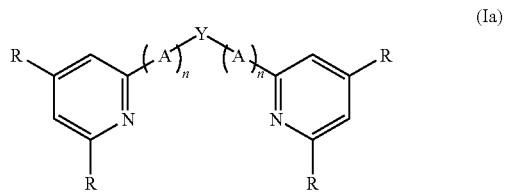

(Ia)

in which Y, A, R and n are as defined in relation to formula (Ia) above.

Preferably, the alkyl, alkylamine, hydroalkyl and alkyloxy chains are methyls, methylamines, hydroxymethyls and methoxy, and the ethereal cyclic chain is of $—C_2H_5—(O—C_2H_5—)_p$ type, p being as defined above.

Advantageously, Y will represent an oxygen or sulfur atom or a group of formula

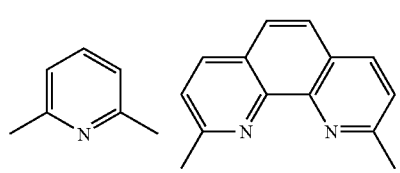

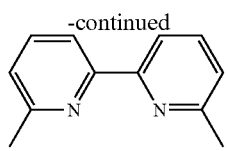

and the groups R, which may be identical or different, will represent a hydrogen, an alkyl or alkyloxy chain containing from 1 to 6 carbons, or a —COOH or —COOR2 group, in which R2 is an alkyl chain containing from 1 to 6 carbons.

The preferred compounds of the invention are more particularly those listed below:
2,9-bis[5-(pyridin-2-yl)pyrrol-2-yl]-1,10-phenanthroline,
2,6-bis[5-(pyridin-2-yl)pyrrol-2-yl]pyridine,
2,6-bis[5-(6-methylpyridin-2-yl)pyrrol-2-yl]-pyridine,
di(6-pyridin-2-yl)pyridazine ether,
di(6-pyridin-2-yl)pyridazine thioether,
2,6-bis[6-(pyridin-2-yl)pyridazin-3-yl]-pyridine,
2,6-bis[6-(6-methylpyridin-2-yl)pyridazin-3-yl]pyridine,
2,6-bis[3-(2-carboxypyridin-6-yl)pyridazin-6-yl]pyridine,
6,6'-bis[6-(pyridin-2-yl)pyridazin-3-yl]-2,2'-bipyridine,
2,9-bis[6-(pyridin-2-yl)pyridazin-3-yl]-1,10-phenanthroline,
2,6-bis[6-(6-methylpyridin-2-yl)pyridazin-3-yl]-2,2'-bipyridine,
2,6-bis[5-(6-methylpyridin-2-yl)pyrrol-2-yl]-2,2'-bipyridine,
6,6'-bis[5-(pyridin-2-yl)pyrrol-2-yl]-2,2'-bipyridine
2,9-bis[6-(6-methylpyridin-2-yl)pyridazin-3-yl]-1,10-phenanthroline,
2,9-bis[5-(6-methylpyridin-2-yl)pyrrol-2-yl]-1,10-phenanthroline.

In particular, the compounds according to the invention are ligands which complex metal ions particularly well, in particular cations of iron, copper, ruthenium, europium, silver and bismuth type. They may be used alone or, as a variant, several identical ligands may be used in combination with one another.

By way of nonlimiting examples of ligands, mention will be made of the metallocatenanes formed from compounds according to the invention.

The inventors have, moreover, investigated the possible biological properties of their compounds and demonstrated therapeutic properties of interest.

The invention is therefore directed toward the compounds according to the invention for use as a medicament, and their use as an active ingredient in therapeutic compositions.

The therapeutic interest of these compounds is described more specifically in Example 52 hereinafter.

The compounds according to the invention have several biological uses that may lead to therapeutic uses.

According to a first therapeutic use, the compounds according to the invention may be used for obtaining a medicament for treating parasitic diseases. The parasitic diseases covered by the invention are in particular leishmaniasis, aspergillosis and candidiasis.

The compounds according to the invention that are preferred for this use are of formula (Ia)
in which:
the group A represents a group

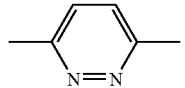

Y represents a sulfur atom, or a group of formula

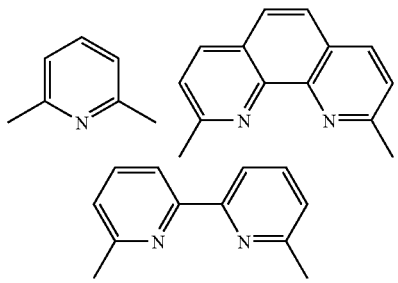

the groups R, which may be identical or different, represent a hydrogen, an alkyl chain containing from 1 to 6 carbon atoms, or a —COOH or —COOR2 group, in which R2 is an alkyl chain containing from 1 to 6 carbons.

In particular, they are the following compounds:
di(6-pyridin-2-yl)pyridazine thioether,
2,6-bis[6-(pyridin-2-yl)pyridazin-3-yl]-pyridine,
2,6-bis[6-(6-methylpyridin-2-yl)pyridazin-3-yl]pyridine,
2,6-bis[3-(2-carboxypyridin-6-yl)pyridazin-6-yl]pyridine,
6,6'-bis[6-(pyridin-2-yl)pyridazin-3-yl]-2,2'-bipyridine,
2,9-bis[6-(pyridin-2-yl)pyridazin-3-yl]-1,10-phenanthroline.

According to a second use, these compounds according to the invention have a cytotoxic activity with respect to cancer cells. They are therefore particularly suitable for the preparation of anticancer medicaments.

Preferably, the cancer targeted by the invention is a carcinoma, for example an ENT carcinoma, a lung carcinoma, a uterine carcinoma, a carcinoma of the digestive tract (esophagus, colon, liver), a skin carcinoma, a breast carcinoma, a prostate carcinoma, an ovarian carcinoma, etc. 6,6'-di(1-ethoxyvinyl)-3,3'-bipyridazine, 6-(pyridin-2-yl)-2H-pyridazine-3-thione, 2,6-bis[6-(6-methylpyridin-2-yl)pyridazin-3-yl]pyridine 49, 2,6-bis[3-(2-carboxypyridin-6-yl)pyridazin-6-yl]-pyridine 50 and di(6-pyridin-2-yl)pyridazine thioether 11, in particular, have shown a very high cytotoxic activity in a cancer cell model: an in vitro test on KB, Caco, Huh7 and fibroblast cells.

The compounds that are preferred according to the invention for this second use are of formula (Ia) in which:
the group A represents a group

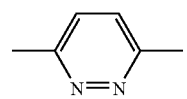

Y represents a group of formula

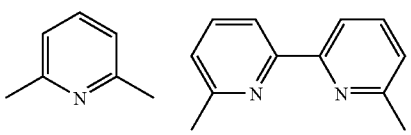

R represents a hydrogen, an alkyl or alkyloxy chain containing from 1 to 6 carbons, or a —COOH or —CONH₂ group.

In particular, they are the following compounds:
2,6-bis[6-(pyridin-2-yl)pyridazin-3-yl]-pyridine,
2,6-bis[6-(6-methylpyridin-2-yl)pyridazin-3-yl]pyridine,
6,6'-bis[6-(pyridin-2-yl)pyridazin-3-yl]-2,2'-bipyridine.

According to a third use, the compounds according to the invention are suitable for the preparation of antibacterial medicaments, for example for the treatment of dysentery or meningitis.

According to a fourth use, some of the compounds according to the invention are vectors of radioactive metals of great interest in the context of radioligands. Consequently, when they are complexed with an appropriate metal, such as bismuth or europium, they make it possible to obtain a medicament for use in radioimmunotherapy.

In particular, they are the compounds of formula (Ia) in which:
if the group A represents a group

the groups R, which may be identical or different, represent a —COOR2 or —CONHR2 group in which the substituents R2 together form an ethereal cyclic alkyl chain,
if the groups A represent a group

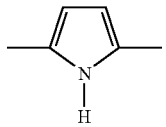

the groups R, which may be identical or different, represent a hydrogen, an alkyl, alkylamine, hydroxyalkyl or alkyloxy chain containing from 1 to 6 carbon atoms, or a —COOH, —CONH$_2$, —COOR2 or —CONHR2 group in which R2 is an alkyl chain containing from 1 to 6 carbon atoms or, when the substituents R are identical in the groups X$_7$, the substituents R2 can together form an ethereal cyclic alkyl chain.

Preferably, the ethereal cyclic alkyl chain is a chain of —C$_2$H$_5$—(O—C$_2$H$_5$—)$_p$ type, p being as defined above.

These compounds are tridentate or tetradentate, mixed N, O or N-donor ligands. They are consequently particularly suitable for complexing metal ions.

According to a fifth use, the compounds according to the invention can selectively complex nucleic acids. In particular, they can be used as selective agents for complexing DNA and RNA, including that of HIV. They in fact act on the reverse transcriptase of cells, by inhibition of its primer on the viral RNA. They are therefore particularly suitable for the preparation of antiviral medicaments. These compounds can also be used as DNA-cleaving agents (metallonuclease, in particular when they are complexed with a metal of Cu type, for example).

The inventors have also defined uses in the environmental, materials and electronics field.

The invention is therefore also directed toward the use of the compounds according to the invention for the decontamination of cations in liquid media.

Preferably,
the groups A, which may be identical or different, represent a group

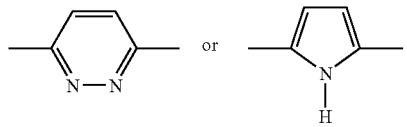

n is an integer equal to 1 or 2,
Y represents a group of formula

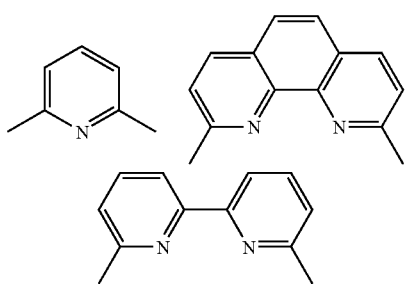

the groups R, which may be identical or different, represent a hydrogen, an alkyl or alkyloxy chain containing from 1 to 6 carbon atoms, or a —COOH, —CONH$_2$, —COOR2 or —CONHR2 group in which R2 is an alkyl chain containing from 1 to 6 carbons or, when the substituents R are identical in the groups X, the substituents R2 may together form an ethereal cyclic alkyl chain.

As already mentioned, these compounds are particularly suitable for complexing metal ions. They can optionally be used alone, or, as a variant, several identical ligands can be used in combination with one another.

Preferably, the compound will be chosen from the following group:
2,9-bis[5-(pyridin-2-yl)pyrrol-2-yl]-1,10-phenanthroline,
2,6-bis[5-(pyridin-2-yl)pyrrol-2-yl]pyridine,
2,6-bis[5-(6-methylpyridin-2-yl)pyrrol-2-yl]-pyridine,
di(6-pyridin-2-yl)pyridazine ether,
di(6-pyridin-2-yl)pyridazine thioether,
2,6-bis[6-(pyridin-2-yl)pyridazin-3-yl]-pyridine,
2,6-bis[6-(6-methylpyridin-2-yl)pyridazin-3-yl]pyridine,
2,6-bis[3-(2-carboxypyridin-6-yl)pyridazin-6-yl]pyridine,
6,6'-bis[6-(pyridin-2-yl)pyridazin-3-yl]-2,2'-bipyridine,
2,9-bis[6-(pyridin-2-yl)pyridazin-3-yl]-1,10-phenanthroline,
2,6-bis[6-(6-methylpyridin-2-yl)pyridazin-3-yl]-2,2'-bipyridine,
2,6-bis[5-(6-methylpyridin-2-yl)pyrrol-2-yl]-2,2'-bipyridine,
6,6'-bis[5-(pyridin-2-yl)pyrrol-2-yl]-2,2'-bipyridine
2,9-bis[6-(6-methylpyridin-2-yl)pyridazin-3-yl]-1,10-phenanthroline,
2,9-bis[5-(6-methylpyridin-2-yl)pyrrol-2-yl]-1,10-phenanthroline.

For the use in decontaminating cations in liquid media, the above compounds will advantageously be employed in combination with a carboxylic acid, in particular α-bromocapric acid. The inventors in fact noted a synergy in the decontaminating activity when this specific combination was used with respect to actinide cations in particular.

The invention also covers the materials composed of a supramolecular organization of compounds according to the invention. In particular, some of the compounds according to the invention have self-assembling properties. Others can self-assemble around metal cations.

These materials have, in addition, advantageous linear optics properties. They make it possible in particular to produce liquid crystals, optical fibers, etc.

The invention is also directed toward, as such, the subgroups of compounds defined for the various applications/uses as products.

Figure 2:
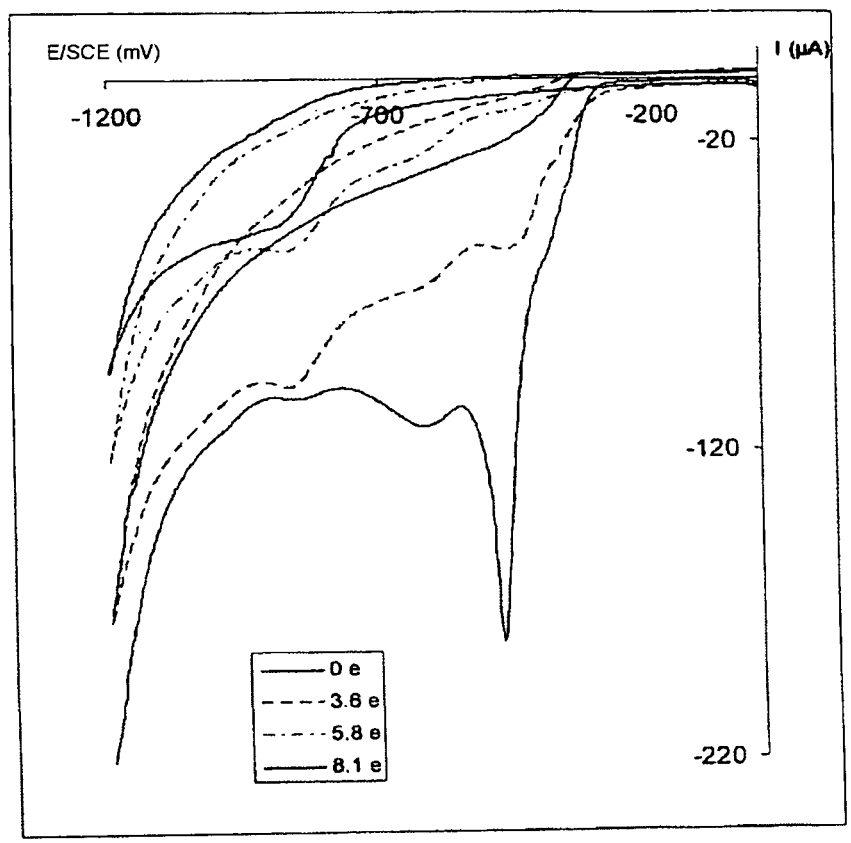
Figure 3:
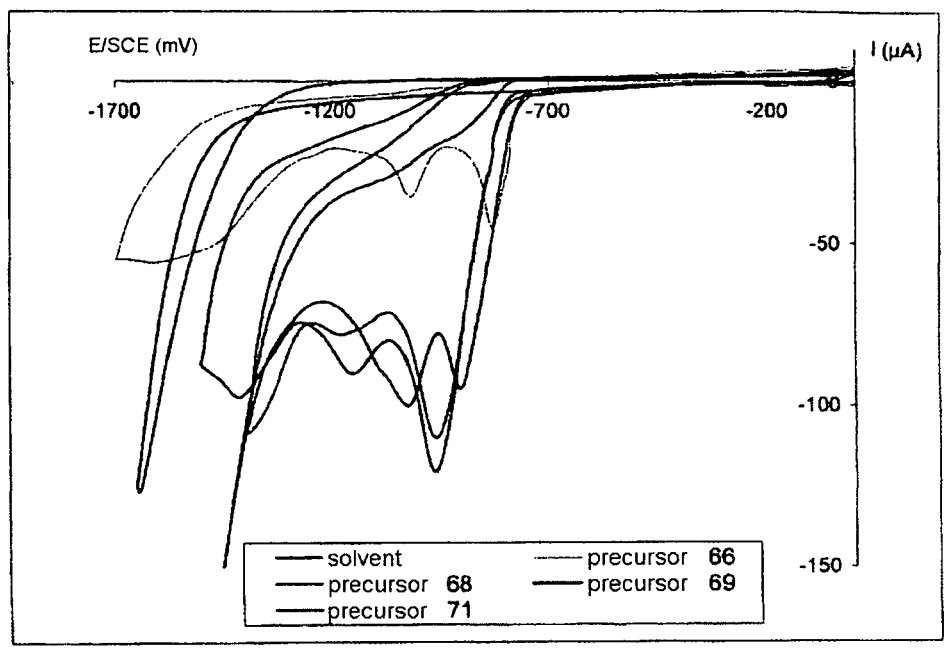
Figure 4:
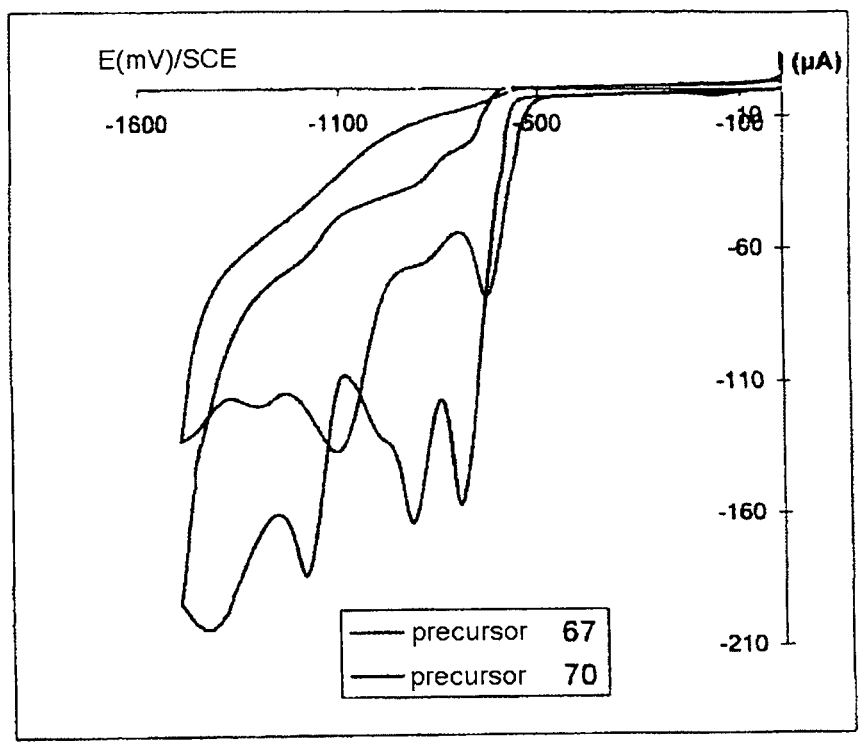
Figure 5:
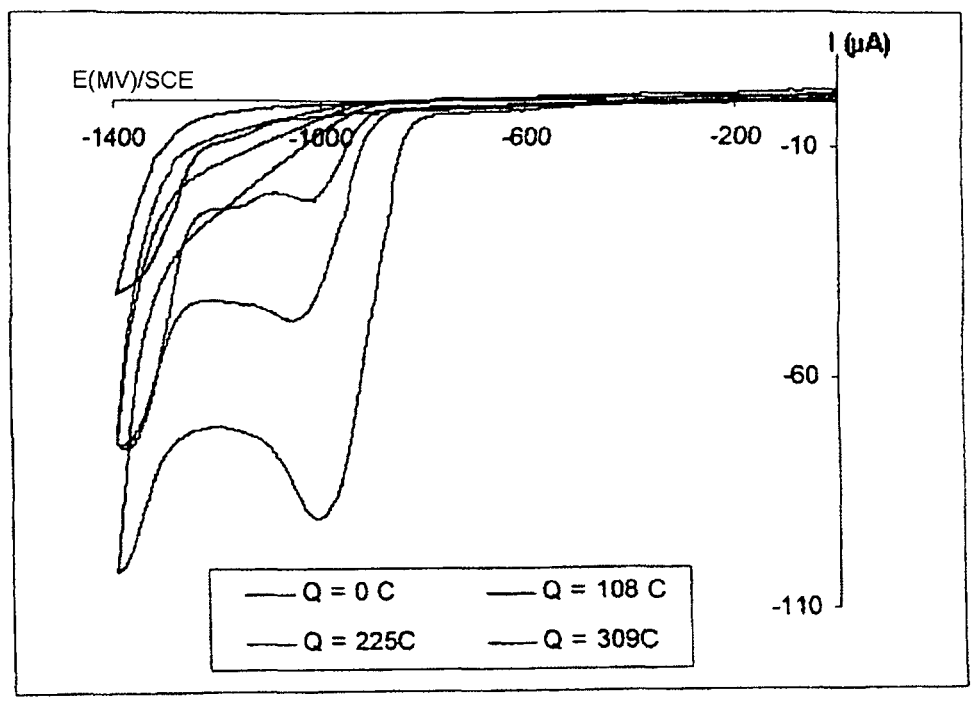
Figure 6:
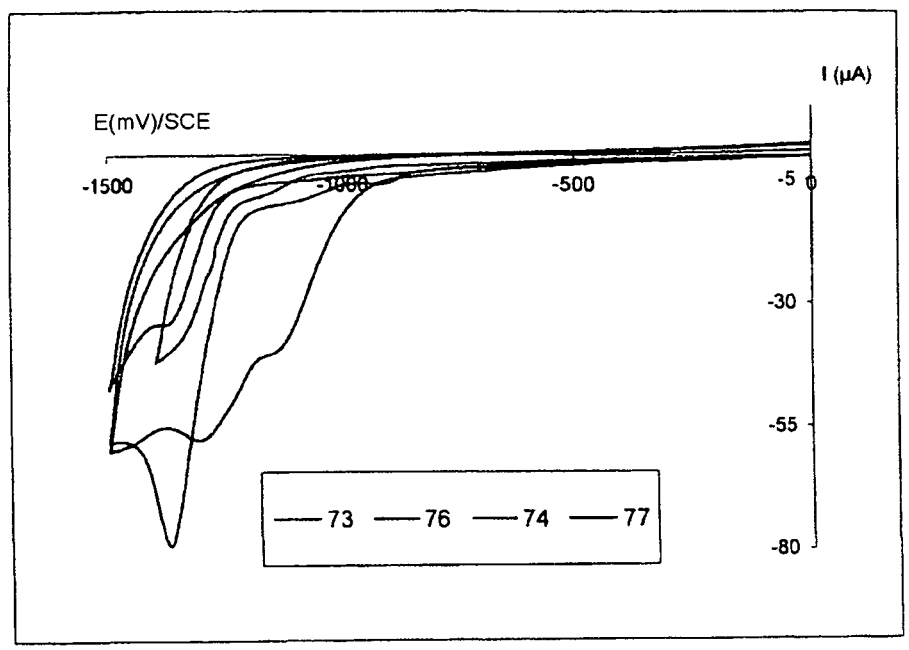
Figure 7:
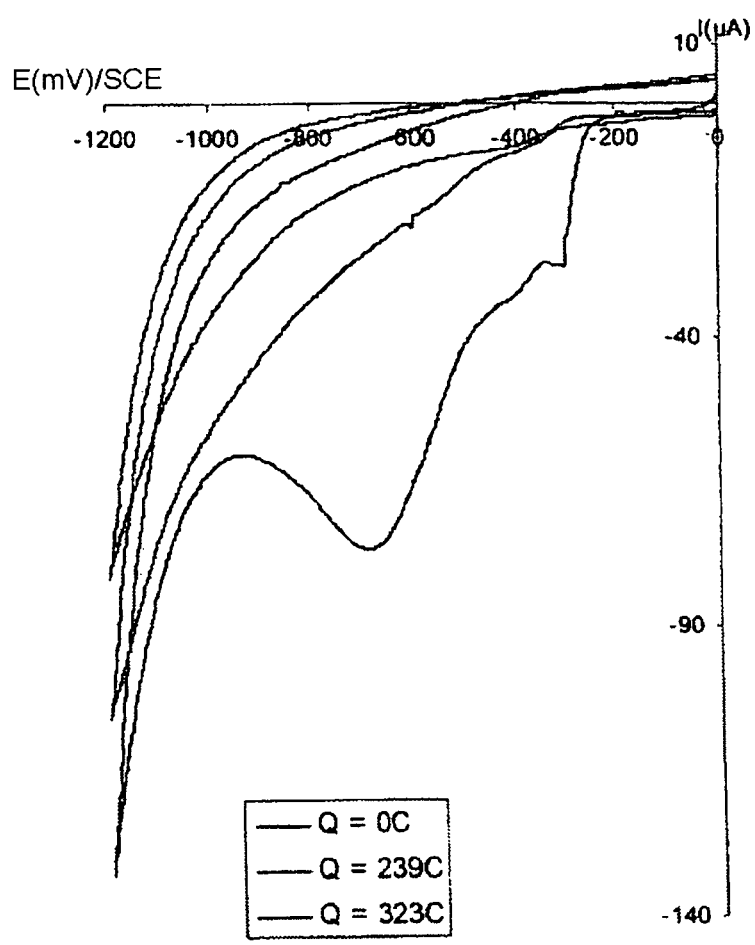
Figure 8:
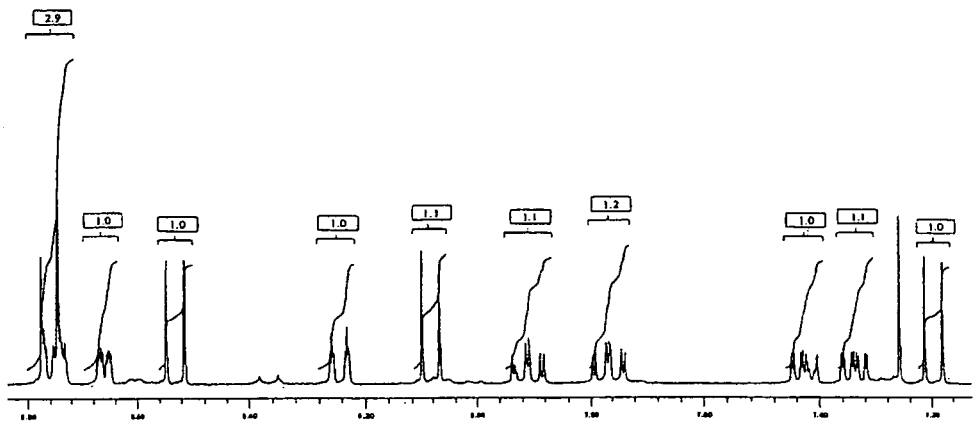
Figure 9:
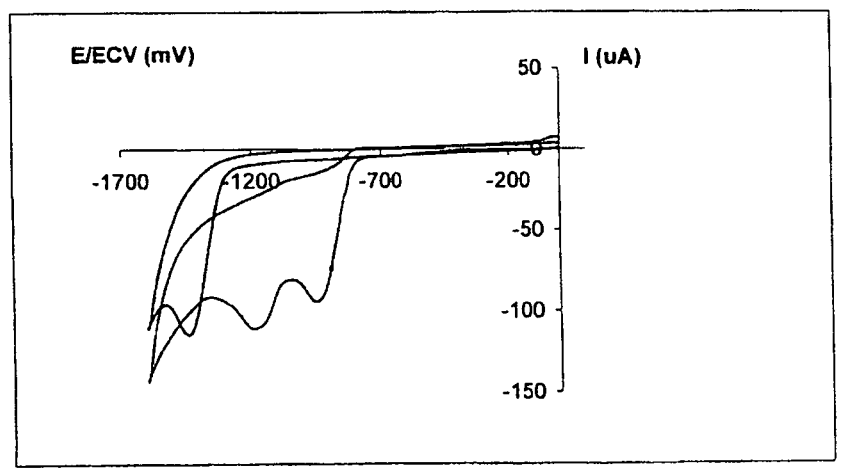
Figure 10:
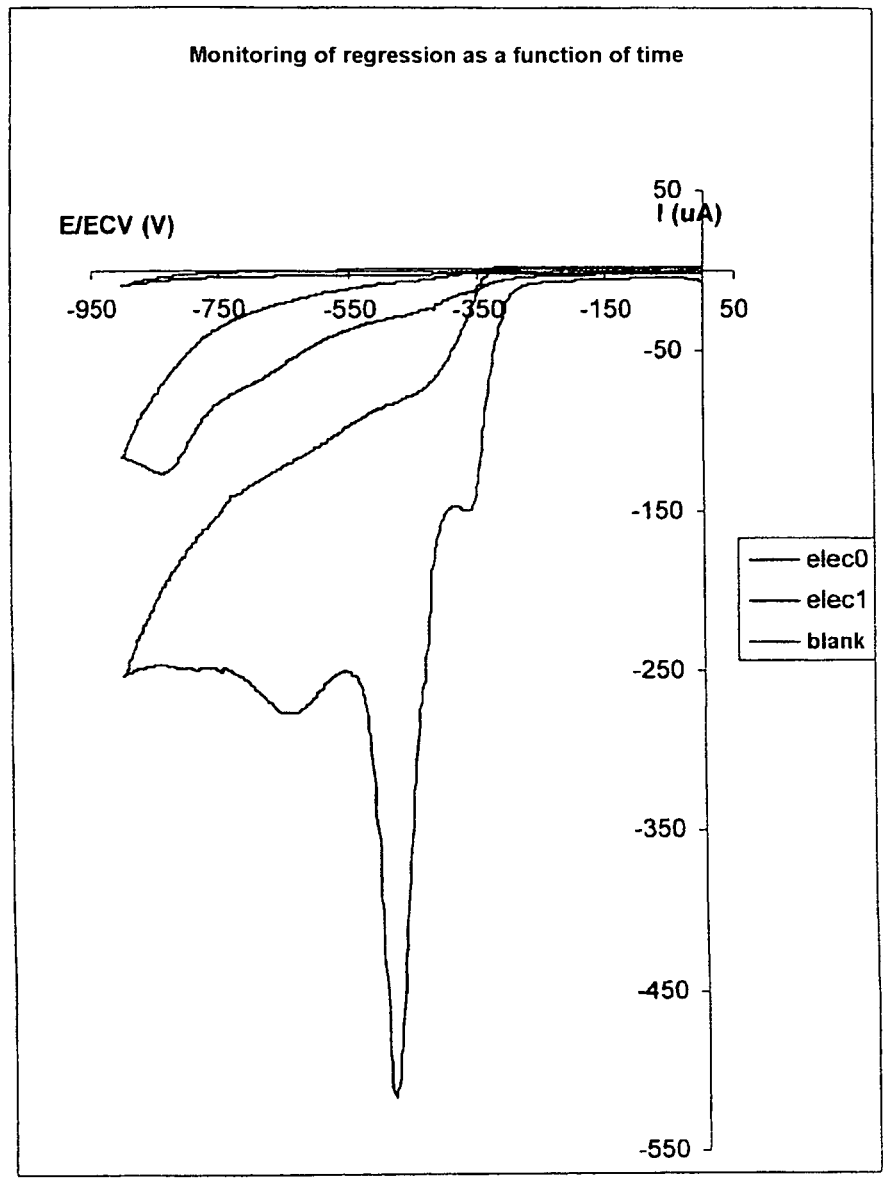
Figure 11:
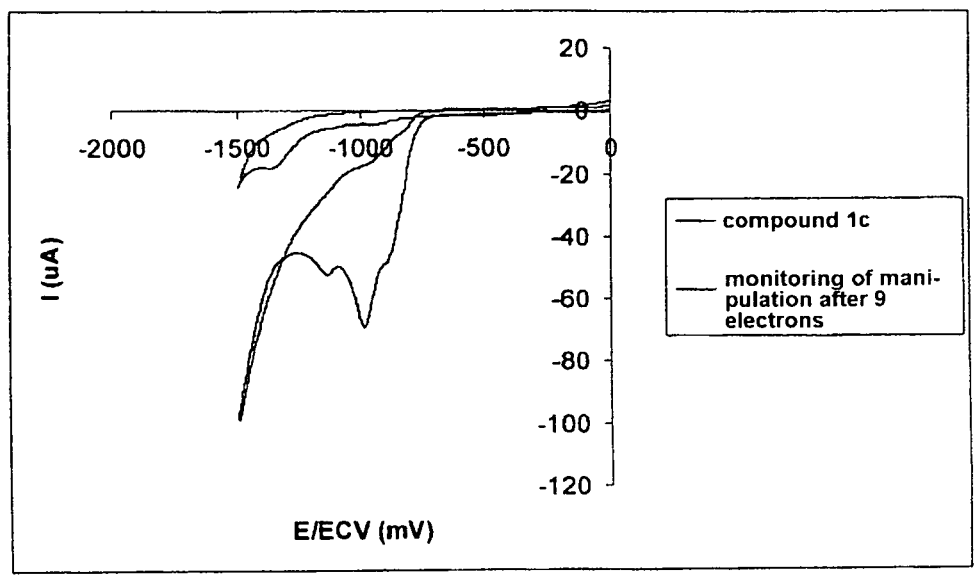
Figure 12:
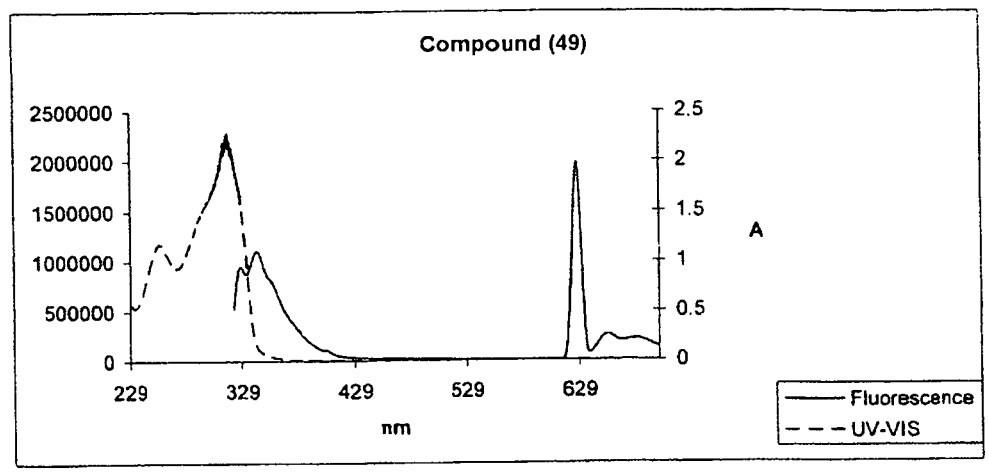
Figure 13:
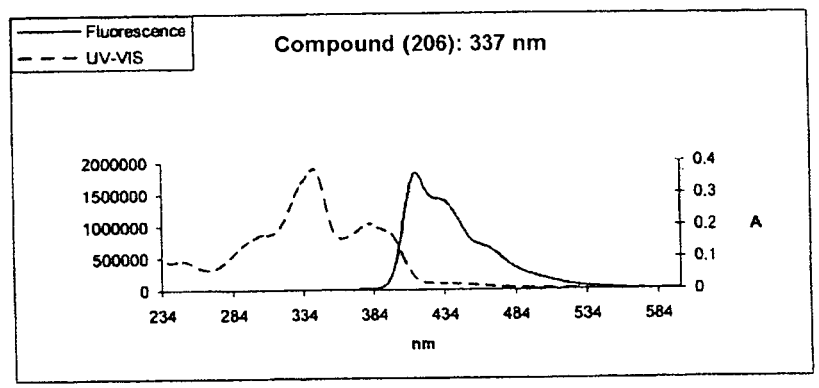
Figure 14:
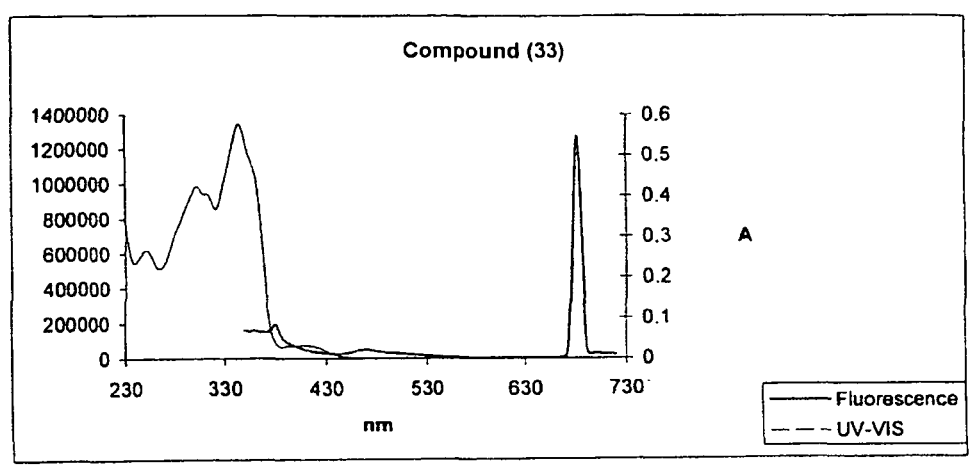

Other characteristics and advantages of the invention will emerge in the examples which follow, with references to the figures, which represent, respectively:

FIG. 1, cyclic voltammograms during the preparative electrolysis, medium $H_2SO_4$ 0.5 $mol \cdot L^{-1}$, ethanol (1/1), C=6× $10^{-3}$ mol/L, v=100 mV/s, FIG. 2, cyclic voltammograms during the preparative electrolysis of 6,6'-bis(6-methylpyridin-2-yl)-3,3'-bipyridazine 2, (—before electrolysis, —during electrolysis, —at the end of electrolysis), vitreous carbon electrode, v=100 mV/s, FIG. 3, cyclic voltammograms of the solvent and of 3,6-bis (pyridin-2-yl)pyridazines in acetic buffer and ethanol medium, C=$10^{-3}$ $mol \cdot L^{-1}$, V=100 mV/s, FIG. 4, cyclic voltammograms of 4-carbomethoxy-3,6-bis (pyridin-2-yl)pyridazine 84 and of 3,6-bis(pyridin-4-yl) pyridazine 81 in acetic buffer and ethanol medium, C=$10^{-3}$ $mol \cdot L^{-1}$, V=100 mV/s, FIG. 5, cyclic voltammograms during the preparative electrolysis of 4-(1-hydroxyethyl)-3,6-bis(pyridin-2-yl)pyridazine 82, (—before electrolysis, —during electrolysis, —at the end of electrolysis), vitreous carbon electrode, v=100 mV/s, FIG. 6, voltammograms of various pyrrole derivatives at the end of preparative electrolysis in the cathode compartment, vitreous carbon electrode, v=100 mV/s, FIG. 7, cyclic voltammograms during the preparative electrolysis of 2,9-di[6-(pyridin-2-yl)pyridazin-3-yl]-1,10-phenanthroline, (—before electrolysis, —during electrolysis, —at the end of electrolysis), vitreous carbon electrode, v=100 mV/s, FIG. 8 is a $^1H$ NMR analysis of the di(6-pyridin-2-yl)pyridazine thioether 11, FIG. 9 gives the voltammograms recorded in the THF/acetic buffer (pH=4.6)/acetonitrile mixture using 2,6-bis[6-(6-methylpyridin-2-yl)pyridazin-3-yl]pyridine 49, FIG. 10 is a voltammogram of the reaction for preparative electrolysis of 6,6'-bis(pyridin-2-yl)-3,3'-bipyridazine (19), blank=reference voltammogram in the absence of product, elec 0=control voltammogram at time 0, elec 1=voltammogram after consumption of 8 electrons, FIG. 11 is a voltammogram of the reaction for preparative electrolysis of 6,6'-bis(4,6-dimethylpyridin-2-yl)-3,3'-bipyridazine 105, FIG. 12 gives the fluorescence and UV-visible absorption spectra for 2,6-bis[6-(6-methylpyridin-2-yl)pyridazin-3-yl]pyridine 49, FIG. 13 gives the fluorescence and UV-visible absorption spectra for 2,6-bis(5-(6-methylpyridin-2-yl)pyrrol-2-yl) pyridine 206, FIG. 14 gives the fluorescence and UV-visible absorption spectra for 2,6-bis[6-(pyridin-2-yl)pyridazin-3-yl]pyridine 33.

GENERAL CONDITIONS AND PROCEDURES RELATING TO THE EXPERIMENTAL SECTION

Nuclear Magnetic Resonance

The $^1H$ and $^{13}C$ NMR spectra were recorded on a Bruker Avance 300 spectrometer. The irradiation frequencies are respectively 300 MHz and 75.5 MHz, the chemical shifts are given in parts per million (ppm) with tetramethylsilane as internal standard. The coupling constants are given in Hertz (Hz) and the multiplicity of the signals is described as follows: s (singlet), bs (broad singlet), d (doublet), dd (doublet of doublets), t (triplet), q (quadruplet), m (multiplet).

UV and Fluorescence Analyses

The UV-visible absorption spectra were recorded on a Shimadzu UV-2401PC spectrometer. The fluorescence spectra were recorded on an SPEX Fluoromax fluorimeter. All the spectra recorded by the machines described above were carried out in a UV-visible quartz cell (1 cm).

Gas Chromatography

The chromatograms were recorded on the HP 6890 machine equipped with a JW 1701 column (30 m×0.25 mm, stationary phase: cyanopropylphenylmethylsilane), and with a flame ionization detector, and nitrogen as vector gas (flow rate=1.3 ml/min). The oven temperature was programmed in the following way: 1 minute at 80° C., then 12° C. per minute up to 280° C.

Thin Layer Chromatography

All the reactions are monitored by thin layer chromatography (Kieselgel 60$F_{254}$, Merck, on aluminum sheet). The plates are developed under UV light or using the Mohr test (10% $FeSO_4$ in water).

Mass Spectroscopy

The mass spectra were recorded on a Thermoelectron DSQ machine by electron impact (70 eV), by chemical ionization (ammonia), by direct introduction or by GC-MS coupling.

Solvent

All the solvents used are purchased pure for synthesis. The tetrahydrofuran (THF) is freshly distilled over sodium/benzophenone under argon. The dichloromethane (DCM) and the N,N-dimethylformamide (DMF) are freshly distilled over calcium hydride under argon. The toluene is freshly distilled over sodium under argon.

Procedure A: General Procedure for the Ullmann-Type Homocoupling Reaction

Tetrabutylammonium bromide, activated zinc powder and dibromo(bistriphenylphosphine)nickel(II) are added to a round-bottomed flask. The whole mixture is dried under vacuum and placed under argon. DMF that has been freshly distilled and degassed is added to the medium via a hollow tube. The solution is stirred at ambient temperature until a homogeneous solution is obtained. The halopyridazine is solubilized in the DMF that has been freshly distilled and degassed and added to the reaction medium via a hollow tube. The solution is stirred for 15 hours at 55° C. The blackish solution is cooled to ambient temperature, treated with an aqueous ammonia solution (25 N) and extracted with DCM. After having dried the organic phase over $Na_2SO_4$ and evaporated off the solvent under reduced pressure, the residue is subsequently purified.

Procedure B: General Procedure for the Acid Hydrolysis

Methoxypyridazine and a solution of HBr at 33% in acetic acid are stirred for 48 hours at 60° C., in a round-bottomed flask surmounted by a condenser. The solution is cooled and concentrated under vacuum. The precipitate is filtered off and washed with acetone. The grayish solid is suspended in water. The solution is brought to reflux and neutralized with a 1M solution of NaOH. The precipitate is filtered off, washed with water and dried under vacuum.

Procedure C: General Procedure for the Chlorination $POCl_3$ and pyridazinone are refluxed for 18 hours, in a round-bottomed flask surmounted by a condenser. After a return to ambient temperature, the excess $POCl_3$ is removed by distillation under vacuum and the residue is hydrolyzed with ice. The solution is subsequently neutralized by adding 1M sodium hydroxide and extracted with dichloromethane. The organic phase is dried over $Na_2SO_4$ and concentrated under reduced pressure.

Procedure D: General Procedure for the Stille Coupling

The previously dried reactants (haloaryl, stannylpyridine, palladium catalyst) are placed in a round-bottomed flask surmounted by a condenser, and the freshly distilled and degassed solvent is added to the reaction medium via a hollow tube. The solution is heated and stirred until the starting product has completely disappeared. After a return to ambient temperature, the solvent is evaporated off under reduced pressure, and the residue is taken up in DCM. The solution is filtered through Celite and washed with DCM. The organic phase is subsequently washed successively with a concentrated aqueous ammonia solution (25 N) and a saturated solution of KF. The organic phase is dried over $Na_2SO_4$ and concentrated under reduced pressure.

Procedure E: General Procedure for the Negishi Coupling

A solution of bromopyridine (1.6 eq.) in freshly distilled and degassed THF is cooled to −78° C., in a three-necked round-bottomed flask surmounted by a condenser. Butyllithium (2.5M in hexane, 1.6 eq.) is added slowly and the reaction medium is stirred for 30 minutes at −78° C. A solution of zinc chloride (previously sublimated, 1.6 eq.) in degassed THF is added, at −78° C., to the reaction medium via a hollow tube. The solution is stirred at ambient temperature for 30 minutes and then a solution of tetrakis(triphenylphosphine)palladium(0) (0.1 eq.) and of halopyridazine (1 eq.) in THF is added to the reaction medium via a hollow tube. The solution is stirred for 48 hours at a temperature dependent on the substrate. The medium is treated with a saturated solution of $NaHCO_3$. The solution is filtered through Celite, and washed successively with DCM and with a concentrated aqueous ammonia solution (25 N). The organic phase is dried over $Na_2SO_4$ and concentrated under reduced pressure.

Procedure F: General Procedure for the Electrochemical Ring Contraction

The compound to be reduced is dissolved either in a three-solvent system (THF/acetic buffer/$CH_3CN$: 5/4/1), or in a 0.5M $H_2SO_4$ solution, and placed in the anode compartment of the electrochemical cell. An identical solvent system is placed in the cathode compartment and the appropriate voltage is imposed until 8 electrons have passed. The organic phase is evaporated under vacuum if necessary. The aqueous phase is subsequently treated with a saturated solution of $Na_2CO_3$ until an alkaline pH is obtained. The medium is extracted with DCM, and the organic phase is dried over $Na_2SO_4$, filtered and concentrated under vacuum. The residue is purified by silica column chromatography (PE/EtOAc: the ratio depends on the compounds).

Example 1

Synthesis of 6,6'-bis(pyridin-2-yl)-3,3'-bipyridazine 19, of 6,6'-bis(5-methylpyridin-2-yl)-3,3'-bipyridazine 2 and of 6,6'-dipicoline-4,4'-dimethyl-2-yl [3,3']bipyridazine 105

A first conventional pathway for access to the 6,6'-bis(pyridin-2-yl)-3,3'-bipyridazine 19 was envisioned according to the following retrosynthetic analysis (Retrosynthesis 1), which is based on the strategy of J. M. Lehn (Baxter, Lehn et al., 2000).

Retrosynthesis 1

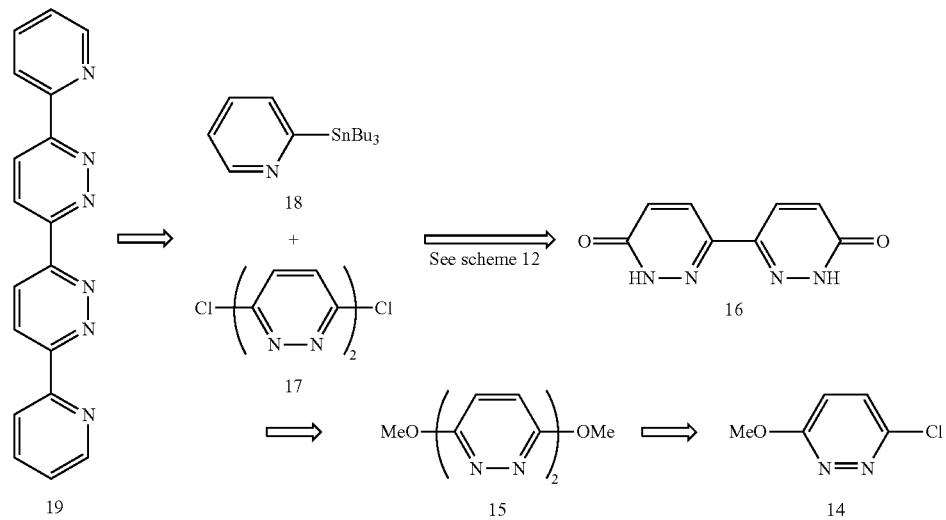

Specifically, it was envisioned, firstly, to use the 6,6'-dichloro-3,3'-bipyridazine dimer 17, which, when subjected to Stille heterocoupling in the presence of two equivalents of 2-tributylstannylpyridine 18, should produce the expected 6,6'-bis(pyridin-2-yl)-3,3'-bipyridazine 19.

The yield from preparation of the 6,6'-bismethoxy-bipyridazine 15 could thus be optimized at 95%, whereas this synthesis was described in three steps starting from the halopyridazine 14 with a 70% yield in the presence of zinc, $NiCl_2(H_2O)_4$ and $PPh_3$ (1:1:4) (Baxter, Lehn et al., 2000). For this, the reaction was reproduced at 55° C., in DMF, starting from a stoichiometric mixture of zinc, $NiBr_2(PPh_3)_2$ and $nBu_4NI$, in a respective proportion of 1:0.3:1 (Scheme 7). The 6,6'-dichloro-3,3'-bipyridazine 17 is subsequently accessible in 2 steps, of hydrolysis and of chlorination with POCl$_3$.

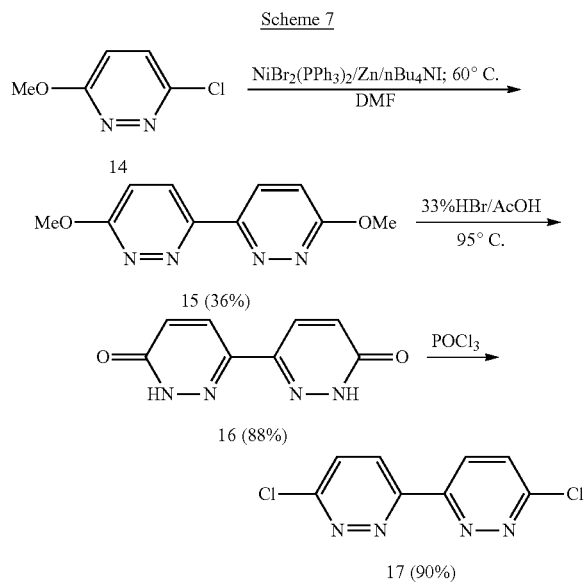

Stille coupling starting from the 6,6'-dichloro-3,3'-bipyridazine 17 was subsequently carried out in the presence of two mol of tributylstannylpyridine 18 and 10% of Pd(PPh$_3$)$_4$ catalyst, so as to give a new 6,6'-bis(pyridin-2-yl)-3,3'-bipyridazine 19 with a yield of 62% (Scheme 8). In parallel, the formation of the homocoupling product 21 (23%) was observed. The use of an excess of organostannane makes the purification of the dimer more difficult.

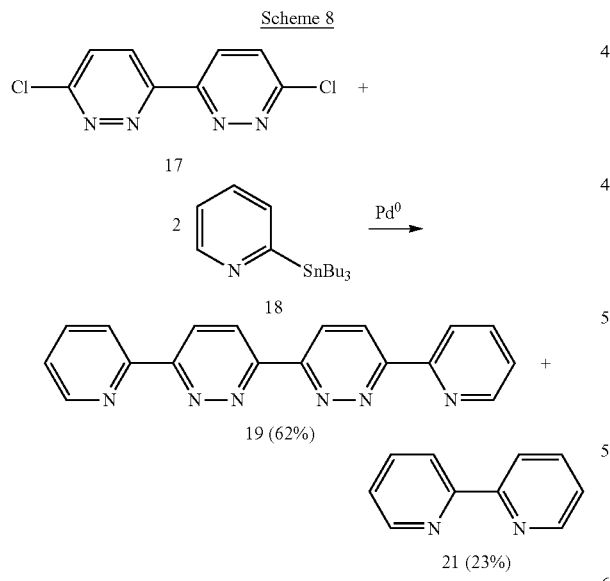

This protocol was also reproduced for the preparation of the 6,6'-bis(6-methylpyridin-2-yl)-3,3'-bipyridazine 2, which was obtained with a 37% yield. The Stille coupling is in this case carried out starting from the 6,6'-dichloro-3,3'-bipyridazine 17 in the presence of the 6-methyl-3-tributylstannylpyridine 22 with a yield of 83% (Scheme 9).

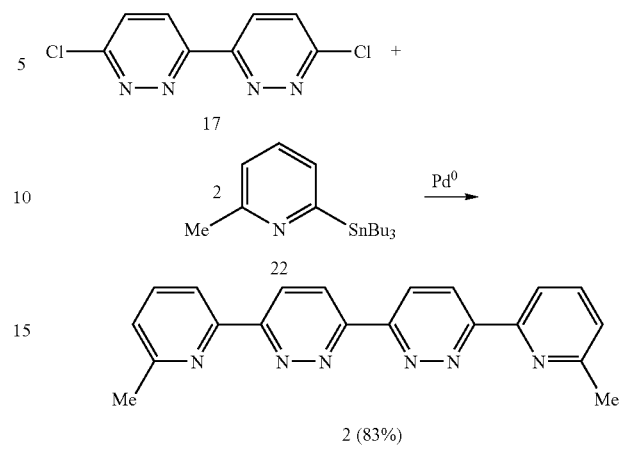

Thus, starting from the same initial precursor, the 6,6'-dichloro-3,3'-bipyridazine 17, it was possible to improve the overall yield of the preparation of bipyridazines 19 and 2, moving from a 53% to a 60% yield in five steps in the case of the bipyridazine 2. This 6,6'-dichloro-3,3'-bipyridazine precursor 17 has the advantage of enabling the introduction of a variety of functionalities at position 6 and 6' on the bipyridazine backbones.

Synthesis of 6,6'-dipicoline-4,4'-dimethyl-2-yl[3,3']-bipyridazine 105

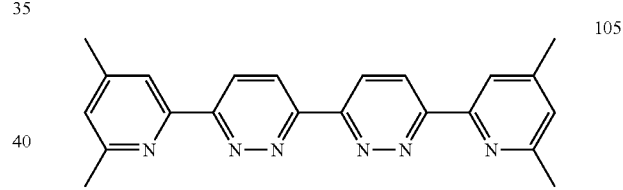

The synthesis pathway used also corresponds to pathway 4 of point 1. The addition of a further methyl substituent on the 6-methylpyridinyl group makes it possible to increase the solubility of the compound and thus to facilitate the electrochemical ring regression.

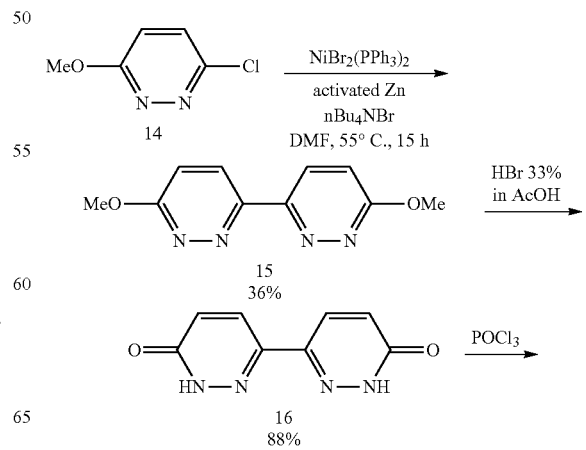

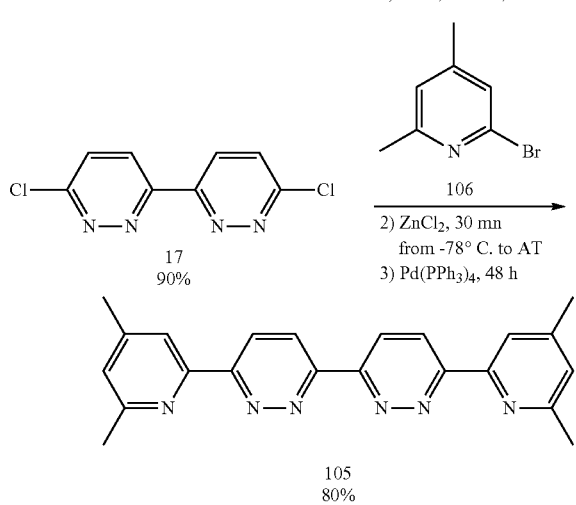

Example 2

Synthesis of 2,2,6,6'-bis(1-ethoxyvinyl)-3,3'-bipyridazine 24 via 6,6'-dichloro-3,3'-bipyridazine 17

Starting from the 6,6'-dichloro-3,3'-bipyridazine 17, many functional modifications are permitted, including access to the 6'-bis(1-ethoxyvinyl)-3,3'-bipyridazine which was obtained with a yield of 68% in the presence of tributyl(1-ethoxyvinyl)tin and of trans-bis(triphenylphosphine)palladium(II) [Pd(PPh$_3$)$_2$Cl$_2$], in DMF at 80° C. (scheme 10).

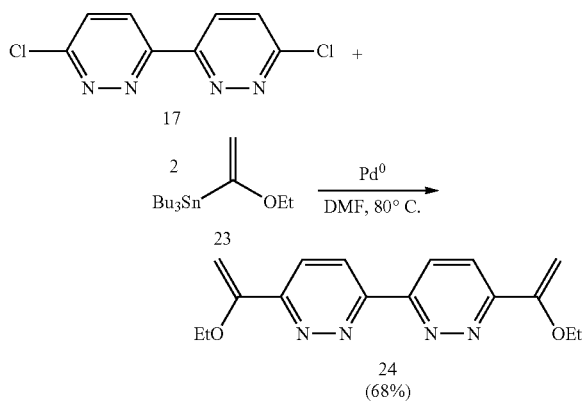

This molecule exhibits a strong cytotoxic potential on KB cancer cells with an IC$_{50}$ of 0.3 μg/ml, and also affects the tonB protein involved in the iron transport process used for bacterial growth.

Example 3

Synthesis of Linear Oligopyridazine Ligands Electrochemically

The consumable anode process (J. Chaussard, J.-C. folest, J.-Y. Nédélec, J. Périchon, S. Sibille, M. Troupel, *Synthesis*, 1990, 369-381) made it possible to carry out aromatic and heteroaromatic halide couplings.

1. Description of the Electrochemical Process Employed

The coupling of aromatic halides is possible by virtue of a process of indirect electrolysis catalyzed by nickel complexes. The process employed is the consumable anode process.

The precursor of the catalyst is introduced in the form of nickel salts (NiBr$_2$, xH$_2$O) or by oxidation of a metal bar containing nickel (stainless steel or Fe/Ni (64/36) steel).

The material used is provided in the following way:

The electrochemical cell is constituted of a glass wall, the lower part of which ending in a thread onto which is threaded a bakelite base (black, SVL40) containing a leaktight seal. In its upper part, four inlets of SVL 15 type are placed around a central inlet SVL22 making it possible to fit a metal bar which will play the role of anode. The cathode, constituted of a nickel foam (40 cm$^2$), is placed concentrically around the anode. The solvent is stirred inside the cell by means of a magnetic bar. The various side inlets have the function of enabling the cathode to be electrically connected by means of a stainless steel wire, and of allowing inlet and outlet of a gas such as argon, which provides an inert atmosphere in the electrochemical cell. The fourth inlet makes it possible to take samples or to add reactants to the reaction medium during electrolysis. One of the inlets may, if necessary, be used to place a reference electrode for measuring the change in potential of the cell during a reaction.

The cell is placed on an oil bath-magnetic stirrer, allowing possible heating, if necessary. DMF is the solvent used in the process. The medium is made conductive through the introduction of support electrolytes, such as quaternary ammonium salts. The supply of electricity to the cell is provided by a stabilized supply which makes it possible to work under galvanostatic conditions of 10 to 300 mA.

The two reactions involved during an electrolysis take place simultaneously. The cathodic reaction concerns the reduction of the most readily reducible species, which, in the present case, is the precursor of the catalyst (nickel II salts). The nickel(II) is thus reduced to nickel(0) stabilized by ligands present in the medium (pyridine or bipyridine). At the anode, the counterreaction is the oxidation of the metal bar, made of iron or of an iron/nickel alloy with a 64/36 composition. The metal salts generated in the medium thus contribute to a correct progression of the reaction. The process involved around the nickel(0) is shown in schemes 1 and 2, according to the intensity imposed: strong (scheme 1) or weak (scheme 2).

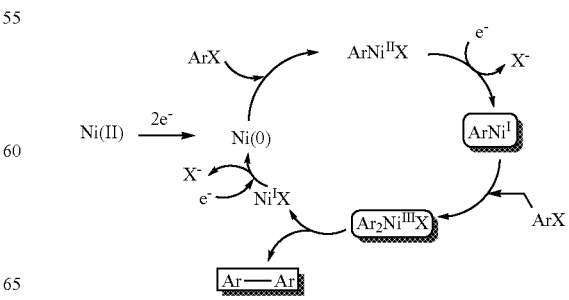

Scheme 2

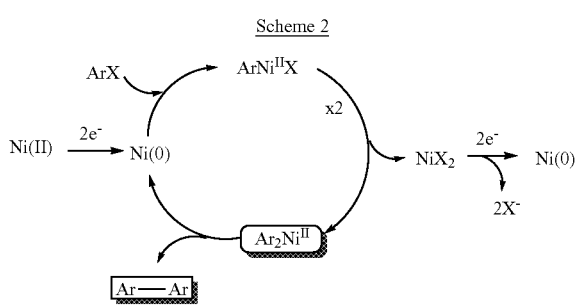

If the anode is made of iron, the precursor of the catalyst used is the NiBr$_2$Bipy (10%) complex, and in the case of an Fe/Ni (64/36) anode, the precursor of the catalyst is NiBr$_2$ (5 to 10%) and the ligand placed as cosolvent is pyridine.

2. Homocoupling of a Pyridazine Halide Electrochemically 6,6'-Dimethoxy-3,3'-bipyridazine 15 is the key intermediate in the synthesis of 6,6'-bisubstituted 3,3'-bipyridazine. A simple and effective original synthesis of this intermediate was developed electrochemically. This synthesis uses the consumable anode process described above and involves the homocoupling of 3-chloro-6-methoxypyridazine 14 by virtue of catalysis with nickel complexes (Scheme 1').

Scheme 1'

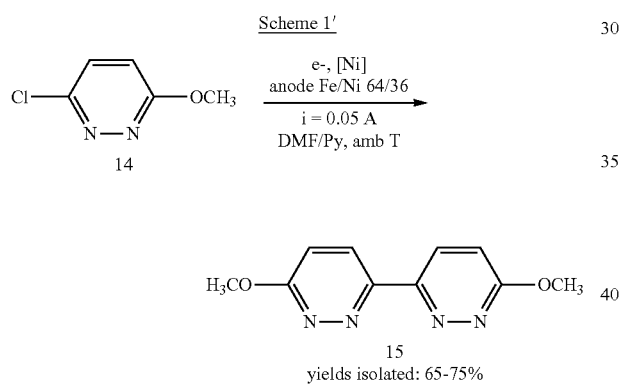

15
yields isolated: 65-75%

The material used is that described in paragraph 1. The anode is an Fe/Ni (64/36) bar and the cathode is a nickel foam (supplier Goodfellow). The solvent is a 50/50 DMF/pyridine mixture and the support electrolyte is constituted of a 1/1 NBu$_4$Er/NBu$_4$I mixture. The reaction is carried out at ambient temperature under an argon atmosphere. A pre-electrolysis in the presence of dibromoethane (300 µl) is carried out for 15 min at an intensity of 0.1 A in the absence of nickel (NiBr$_2$, xH$_2$O, 10%) and of the reactant (3-chloro-6-methoxypyridazine). The latter are subsequently added and the electrolysis is continued at an intensity of 0.05 A. The progression of the reaction is followed by GC analysis of samples of the reaction medium which are hydrolyzed (mixture of a saturated aqueous solution of EDTA/CH$_2$Cl$_2$), this being until complete disappearance of the aryl halide (duration: approximately 15 to 19 h). The solvent is evaporated off under reduced pressure. The residue is taken up in a mixture (saturated aqueous solution of EDTA and of dichloromethane) and subjected to magnetic stirring for one hour. The organic phase is separated from the aqueous phase and the latter is extracted with CH$_2$Cl$_2$ (4 times 100 ml). The combined organic phases are dried over anhydrous sodium sulfate, filtered, and concentrated under reduced pressure. The residue obtained is purified by chromatography on neutral alumina (elution 100% CH$_2$Cl$_2$).

Experimental Data:

6,6'-Dimethoxy-3,3'-bipyridazine 1, CAS RN [24049-46-5]:

White crystals; mass obtained=695 mg; yield=64%; (purification on alumina gel, eluent: 100% dichloromethane). Melting point: 238-239° C. (lit.: 237-238° C.)

$^1$H NMR (CDCl$_3$, 300 MHz, δ ppm): 8.60 (d, 2H, J=9.3 Hz); 7.11 (d, 2H, J=9.3 Hz), 4.19 (s, 6H, OCH$_3$).

$^{13}$C NMR (CDCl$_3$, 75 MHz, δ ppm): 165.47; 152.47; 127.41; 118.21; 55.07.

MS (EI) M/Z (%): 219 (13), 218 (100), 217 (57), 189 (32), 175 (33), 147 (31), 119 (12).

Similarly, the preparation of 6,6'-dichloro-3,3'-bipyridazine 17 was carried out by electrochemical homocoupling of 3,6-dichloropyridazine 1' according to the following reaction (Scheme 2'):

Scheme 2'

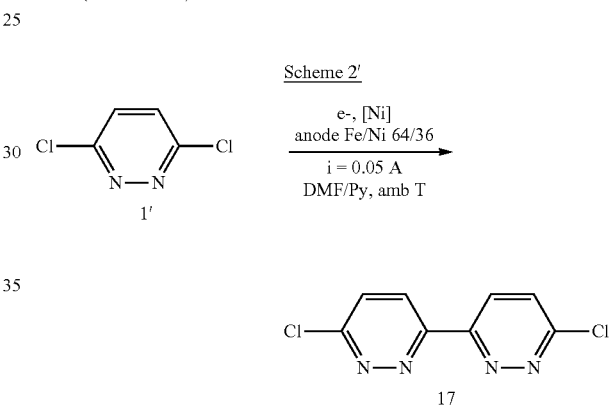

3. Heterocoupling of a Pyridazine Halide Electrochemically

The reaction carried out is the following (Scheme 4'):

Scheme 4'

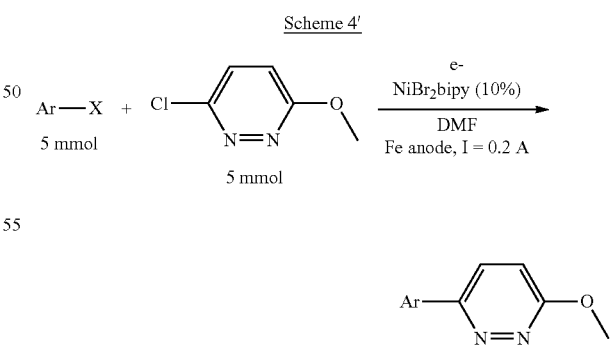

The heterocouplings were carried out, unlike the homocouplings, at an intensity of 0.2 A. The precursor of the catalyst is the NiBr$_2$bipy complex added in catalytic amount (10%). The anode is made of iron (XC10, 0.1% of carbon). The solvent is DMF. The results obtained are given in the table below (Table 1)

TABLE 1 heterocoupling of aromatic halides with 3-chloro-6-methoxypyridazine

| Entry | ArX | Product | Yield isolated (%) |
|---|---|---|---|
| 1 | Ph–I | 3-phenyl-6-methoxypyridazine | 60 |
| 2 | 4-F₃C-C₆H₄–Br | 3-(4-trifluoromethylphenyl)-6-methoxypyridazine | 62 |
| 3 | 4-NC-C₆H₄–Br | 3-(4-cyanophenyl)-6-methoxypyridazine | 58 |
| 4 | 4-MeO₂C-C₆H₄–Br | 3-(4-methoxycarbonylphenyl)-6-methoxypyridazine | 70* |
| 5 | 3-bromothiophene | 3-(thiophen-3-yl)-6-methoxypyridazine | 56* |
| 6 | 3-bromopyridine | 3-(pyridin-3-yl)-6-methoxypyridazine | 33 |

*intensity 0.05 A

The yields obtained are about 60%, except for the 3-bromopyridine (entry 6), where a decrease is observed (33%). For the methyl para-bromobenzoate (entry 4) and the 3-bromothiophene (entry 5), the reactions were carried out at 0.05 A.

According to the retrosynthetic scheme shown below (Retrosynthesis 1'), it is therefore possible to envision two approaches to bipyridazines via electrochemical couplings.

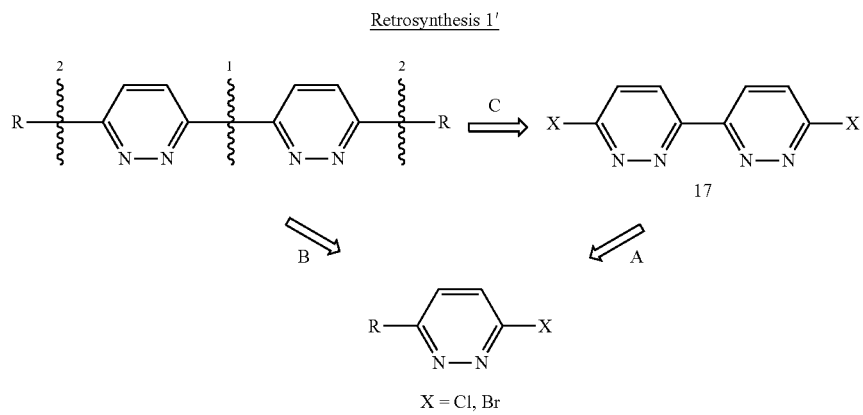

Retrosynthesis 1'

R = X or aryl or other groups

For retrosynthetic pathway A, coupling making it possible to obtain 6,6'-dichloro-3,3'-bipyridazine 17 through homocoupling of 3,6-dichloropyridazine 1' is envisioned (see above).

Starting from 17 many bipyridazine structures, for which R is variable, are accessible chemically or electrochemically.

With regard to retrosynthetic pathway B, the synthesis of 6,6'-bis(pyridin-2-yl)-3,3'-bipyridazines 19 and 2 is carried out in two electrochemical steps according to Scheme 7' via the intermediate 2'.

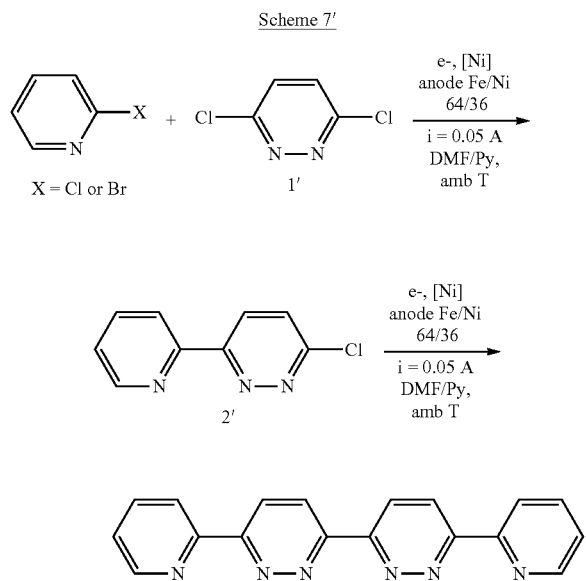

Furthermore, this study approach makes it possible to obtain nonsymmetric bipyridazine analogs for which R and R' are variable (Scheme 8').

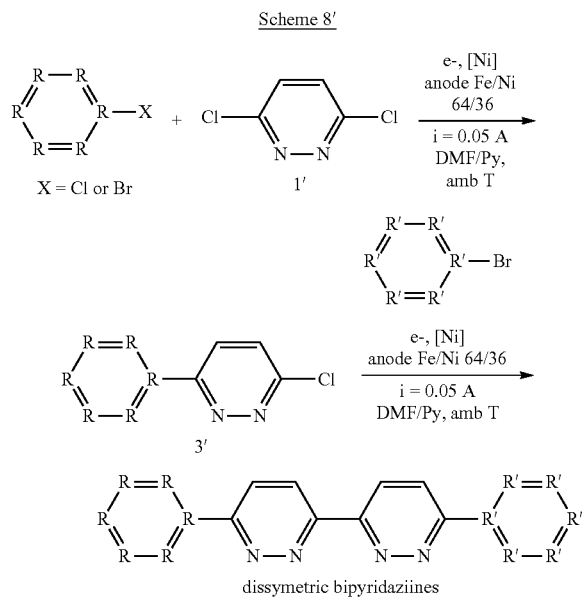

Example 4

Synthesis of Bipyrrole Sequences by Electrosynthesis

Some bipyridazine structures were subjected to electrochemical ring regression conditions. The electroreduction experiment was carried out in a sulfuric acid medium because the 3,3'-bipyridazines 2 and 19 are not readily soluble in the acetic buffer. The conditions were the following: vitreous carbon electrode, v=100 mV/s. The voltammogram of 6,6'-bis(6-methylpyridin-2-yl)-3,3'-bipyridazine 2 clearly indicates a very marked reduction wave at a potential of −0.5 V/SCE and a slight shoulder around −0.6 V/SCE (FIG. 1).

According to the first studies, it was conceivable that the first wave may correspond to a potential of a simultaneous two-electron reduction (two electrons per pyridazine ring), of the two symmetric pyridazine groups of the dimer 2 (4 electrons in total). The formation of a bisdihydropyridazine intermediate 68 could therefore be envisioned and its regression to the dipyrrole 71 logically had to require a further provision of at least four electrons per mole (two electrons per dihydro ring), for a total of eight electrons/mol starting from the bipyridazine 2 (scheme 121).

The preparative electrolysis of this compound was thus carried out in a sulfuric medium by applying a working potential of −0.5 V/SCE for one hour (Q=210 C) and then such electrolysis was continued at a potential of −0.6 V/SCE until almost complete consumption of the precursor (Q=305 C). This preparative electrolysis was monitored by cyclic voltammetry directly in the cathode compartment on a carbon electrode at various stages of the electrosynthesis (FIG. 1: —before electrolysis, —during electrolysis, —at the end of electrolysis). A decrease in the intensity of the wave of reduction of the bipyridazine compound 2 on the various voltammograms clearly shows the reduction of said compound during the preparative electrolysis. The latter was halted after complete disappearance of this wave (experiment lasting 4 h 30, during which at least four electrons were therefore consumed).

At the end of the electrolysis, the amount of Coulombs consumed in this experiment in fact corresponds to only 4.78 electrons per mole of bipyridazine substrate (for a theoretical value of $Q_t$=440 C=8e$^-$).

This electroreduction (Scheme 121) results, according to this procedure, predominantly in the formation of 3-[5-(6-methylpyridin-2-yl)pyrrol-2-yl]-6-(6-methylpyridin-2-yl)pyridazine 70.

The selective reduction of just one pyridazine nucleus out of the two is therefore possible. The mechanism involves either a first 4-electron reduction of the pyridazine dimer, which would result in bis-1,2-dihydropyridazines 68, or two successive steps of 2-electron reduction via the intermediate 69. The latter hypothesis was first of all suggested through the identification, in the medium, of the intermediate 3-[6-(6-methylpyridin-2-yl)dihydropyridazin-3-yl]-6-(6-methylpyridin-2-yl)pyridazine 69 resulting from a first reduction with 2 first electrons.

Scheme 121

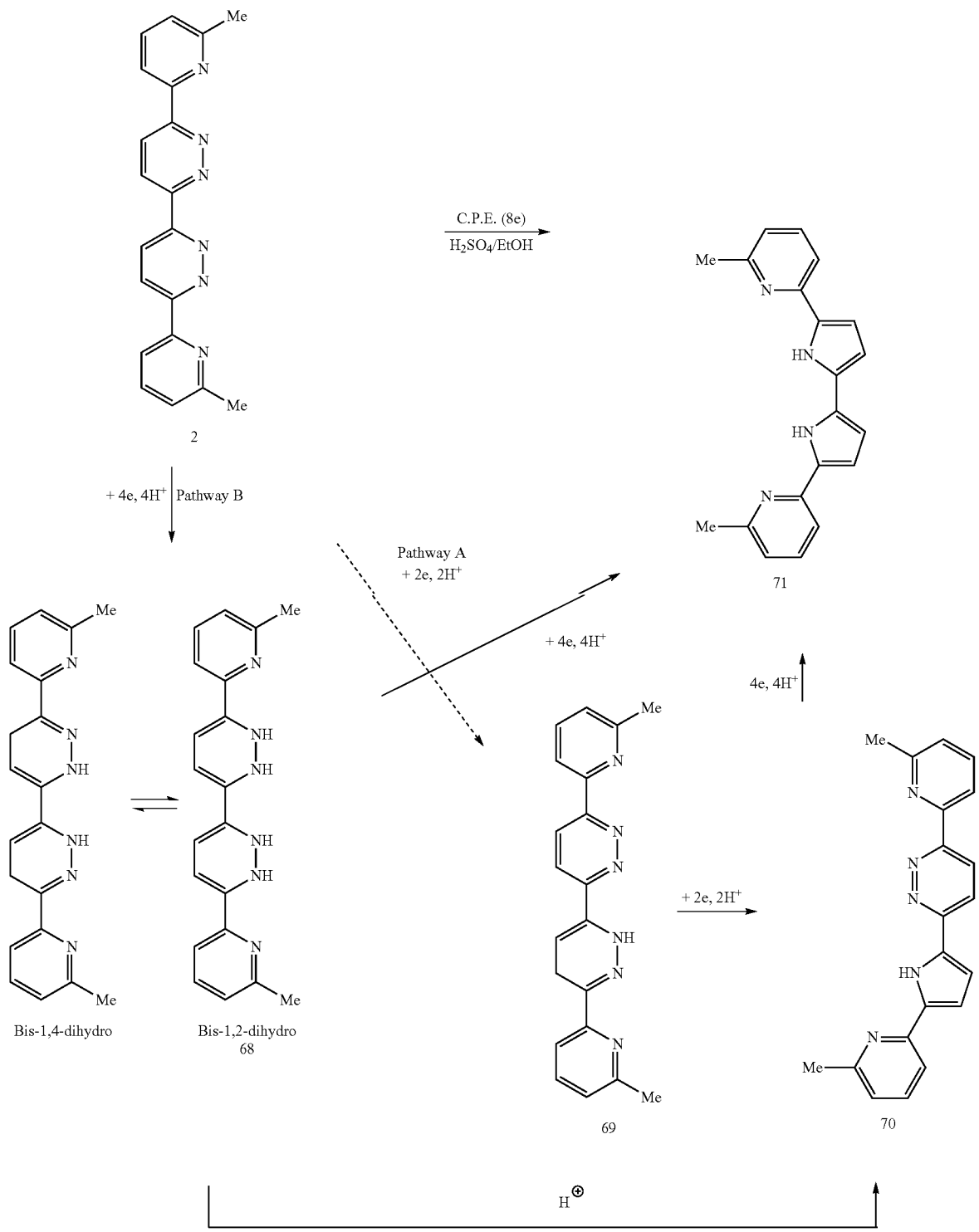

The identification of two compounds was confirmed by virtue of their mass spectrum, respectively m/z=[M−H] 341 for the dihydro 69 and m/z=[M] 327 for the pyrrole compound 70. The analysis of the $^1$H NMR spectrum of the pyrrole 70 indicates the presence of an NH at δ=11 ppm and of 2 pyrrole protons at δ=6.77 and 6.78 ppm ($^3$J=3.9 Hz). The latter also couple with the NH of the pyrrole with respective coupling constants $^4$J of 2.4 Hz and 2.7 Hz.

This alternative offers the possibility of access to alternate pyridazine-pyrrole systems.

The preferred mechanism in fact appears to have to work by forming a bis-1,2-dihydropyridazine 68 (resulting from a 4-electron reduction) which becomes rearranged, in an acidic medium, to a mixed pyrrole-pyridazine system 70. Subsequently, the bipyrrole 71 results from a further 4-electron reduction of the remaining pyridazine.

dominant fractions could be isolated by chromatography: one containing a 1,2,3,4-tetrahydropyridazinylpyrrole 72, and the other containing the expected bipyrrole 71 (Scheme 122).

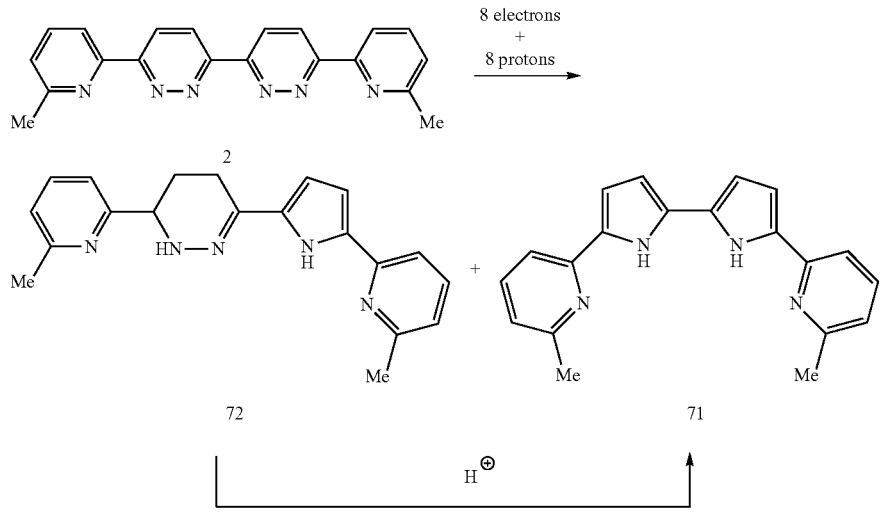

Scheme 122

In fact, according to the experimental protocol which was selected for this electroreduction experiment, in which only 4.78 electrons per mole were consumed, the formation of the bipyrrole 71, which requires 8 electrons per mole of bipyridazine 2, could not be optimal. Its presence was nevertheless demonstrated under these conditions, but in a low proportion. In fact, the $^1$H NMR of the reaction crude indicates unambiguously the NH peak of the pyrroles at δ=9.65 ppm for this symmetric molecule and its mass spectrum complies (m/z=[M+1] 313).

$^1$H NMR (300 MHz, CDCl$_3$) of 71: 9.65 (bs, 2H, NH); 7.45 (t, 2H, $^3$J=7.5 Hz, 2H4'pyridinyl); 7.31 (d, 2H, $^3$J=7.5 Hz, 2H3'pyridinyl); 7.31 (d, 2H, $^3$J=7.5 Hz, 2H5'pyridinyl); 6.66 (m, 2H, 2H pyrrole); 6.41 (m, 2H, 2H pyrrole); 2.49 (s, 6H, CH$_3$).

Preparative Electrolysis of the Bipyridazine 2, Eight-Electron Reduction

The study was repeated with the electroreduction potential being gradually shifted toward more negative values of −0.7 V/SCE to complete disappearance of the substrate (i.e. a consumption of 8.15 electrons per mole of substrate). The disappearance of the principal wave during the previous experiment, coinciding with the appearance of another wave at a potential of approximately −0.8 V/SCE, was observed (FIG. 1). It corresponds to the reduction of 3-[5-(6-methylpyridin-2-yl)pyrrol-2-yl]-6-(6-methylpyridin-2-yl)pyridazine 70 to the corresponding bipyrrole 71.

As in the previous electrolysis, the monitoring was carried out by cyclic voltammetry (FIG. 2).

In FIG. 2, it can be observed that, after the passing of four electrons, starting product still remains, characterized by the first three waves still present. The appearance of a new wave, which is more cathodic, and which is characteristic of the final product of the reaction, can also be noted.

The treatment, identical to the preceding test, itself also gives a mixture of reaction products and the NMR analysis of the reaction crude contains many peaks. However, two pre- The presence of this tetrahydropyridazinepyrrole 72 reaction product leads one to conclude that the 8 electrons indeed serve to reduce the pyridazine, since represents the synthesis intermediate of the bipyrrole 71.

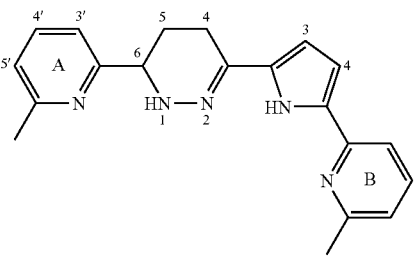

$^1$H NMR (400 MHz, CDCl$_3$) 72:10.07 (bs, 1H, NH pyrrole); 7.62 (t, 1H, $^3$J=7.7 Hz, H4'pyridinylA); 7.41 (t, 1H, $^3$J=7.7 Hz, H4'pyridinylB); 7.34 (d, 1H, $^3$J=7.7 Hz, H3'pyridinylB); 7.26 (d, 1H, $^3$J=7.7 Hz, H3'pyridinylA); 7.09 (d, 1H, $^3$J=7.7 Hz, H5'pyridinylA); 6.88 (d, 1H, $^3$J=7.7 Hz, H5'pyridinylB); 6.64 (m, 1H, H4 pyrrole); 6.33 (m, 1H, H3 pyrrole); 6.02 (bs, 1H, NH tetrahydropyridazine); 4.30 (1d, 1H, $^3$J=, 9.9, 3.09, H6 tetrahydropyridazine); 2.70 (m, 1H, H4 tetrahydropyridazine); 2.65 (m, 1H, H4 tetrahydropyridazine); 6.64 (s, 6H, CH3); 2.54 (m, 1H, H5 tetrahydropyridazine); 2.16 (m, 1H, H5 tetrahydropyridazine);

$^{13}$C NMR (400 MHz, CDCl$_3$) 72:160.4 (C2' pyridinylA); 158.2 (C6' pyridinylA); 157.9 (C6' pyridinylB); 149.7 (C2' pyridinylA); 138.5 (Cq pyrrole); 136.7 (C4' pyridinylA); 136.5 (C4' pyridinylB); 132.6 (Cq pyrrole); 122.2 (C3' pyridinylA); 121.0 (C3' pyridinylB); 120.1 (C5' pyridinylA); 117.5 (C5' pyridinylB); 108.2 (C4 pyrrole); 107.5 (C3 pyrrole); 57.5 (C6 tetrahydropyridazine); 26.0 (C5 tetrahydropyridazine); 24.6 (2 CH3) 22.1 C4 tetrahydropyridazine).

However, an improvement to the process may either relate to the potential to be applied (up to 0.85 V/SCE), or be provided by simply allowing the reaction to continue. The hypotheses are that, at −0.7 V/SCE, the dihydropyridazine 2 is reduced to 72 and that the rearrangement to the bipyrrole 71, in an acidic medium, simply requires a longer reaction time.

Example 5

Reduction of 6,6'-bis(pyridin-2-yl)-3,3'-bipyridazine by Controlled-Potential Preparative Electrolysis The preparative electrolysis is carried out in a sulfuric acid (0.5 mol·L$^{-1}$)/ethanol medium (proportion: 0.5/0.5) in a cell with two compartments separated by sintered glass. The anode, a stainless steel plate with a surface area of 15 cm$^2$, is placed in the anode compartment. The cathode, a layer of mercury with a surface area of 16 cm$^2$, and the reference electrode, the saturated calomel electrode, are introduced into the cathode compartment. The solvent volume in the two compartments is 90 ml. The substrate is introduced into the cathode compartment (194 mg, i.e. 5.7×10$^{-4}$ mol) and the potential applied at the beginning of electrolysis is −0.5 V/SCE (substrate reduction potential), the corresponding intensity is 35 mA. After 1 hour of electrolysis, the latter is continued at −0.6 V/SCE until disappearance of the substrate (4 h 30), the intensity at the end of electrolysis is 8 mA. The electrolysis is monitored by cyclic voltammetry on a carbon electrode (S=3.2 mm$^2$) directly in the cathode compartment. The amount of Coulombs consumed during the electrolysis is 305 C, i.e. 5.57 electrons per mole of substrate. The reaction medium in the cathode compartment is evaporated so as to remove the ethanol, and then neutralized with NaHCO$_3$. After extraction with dichloromethane, the organic phase is dried over Na$_2$SO$_4$ and then evaporated. The monopyrrole compound 3-[5-(pyridin-2-yl)pyrrol-2-yl]-6-(6-methylpyridin-2-yl)pyridazine is purified by silica gel chromatography (yield 50%).

Obtaining the 5,5'-bis(pyridin-2-yl)-2,2'-bipyrrole 112

In order to optimize the electrosynthesis of the bipyrrole, carrying out the electrolyses under the same working conditions (solvent, electrodes), but with the electroreduction potential being gradually shifted to more negative values (E=−0.85 V/SCE), results in the formation of the bipyrrole system.

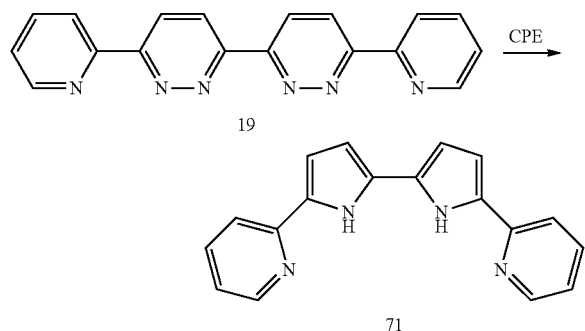

The difficulties in solubilizing the compound 19 meant that it was not possible to perform the electrochemical regression under conventional conditions (EtOH/acetic buffer); only solubilization in 0.5M sulfuric acid is possible. The votammograms recorded in 0.5M sulfuric acid demonstrated three successive reduction waves at potentials E$_c$=−0.363 V, −0.500 V and −0.673 V. Under the same conditions, the pyrrole compound shows a reduction wave corresponding to the reduction of the pyrroles with a potential E$_c$=−0.818 V.

The reaction for performing preparative electrolysis of the bipyridazine 19 electrochemically was carried out in 0.5M H$_2$SO$_4$ medium. A potential E$_t$=−0.650 V/SCE was applied to the working electrode (layer of mercury) until consumption of 8 electrons. The reaction is monitored by cyclic voltammetry and TLC (see FIG. 10).

The bipyrrole compound 112 was obtained with a yield in the region of 10%, along with the monopyrrole compound 107 and the tetrahydropyridazine compound 108. The low yield obtained for the bipyrrole is explained by its partial degradation in the concentrated H$_2$SO$_4$ medium and the difficulties in purification by flash chromatography on silica gel.

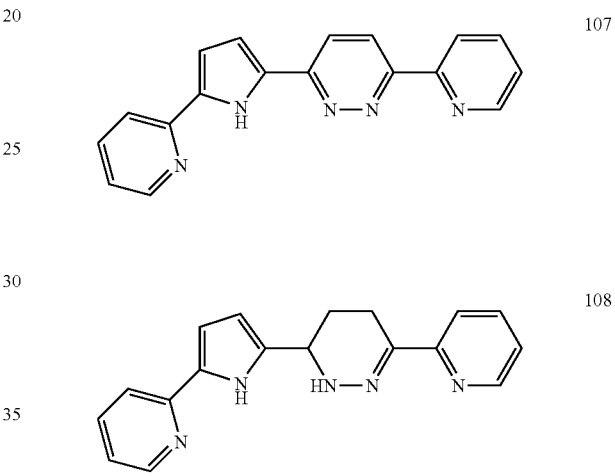

Example 6

Analytical Studies of the Reduction of Polycyclic Pyridazines

The analytic studies show that the 3,6-bis(pyridin-2-yl) pyridazines 80, 82, 83 and 85 show voltammograms similar to their 3,6-dicarbomethoxypyridazine analogs. Thus, the first four-electron peaks are well defined and appear at potentials between −0.9 V and −1.1 V (FIG. 3, cyclic voltammogram of the solvent and of the precursors 80, 82, 83 and 85 in acetic/ethanol medium, C=10$^{-3}$ mol·L$^{-1}$, V=100 mV/s).

The voltammograms of the precursors 4-carbomethoxy-3,6-bis(pyridin-2-yl)pyridazine 84 and 3,6-bis(pyridin-4-yl) pyridazine 81 are more complex, and several reduction waves appear starting from more positive potentials (−0.7 V) (FIG. 4, cyclic voltammograms of the precursors 81 and 84 in acetic buffer+ethanol medium, C=10$^{-3}$ mol·L$^{-1}$, V=100 mV/s).

The values of potentials of the peaks Ep of the first two reduction peaks for these various precursors are given in Table 4.

TABLE 4

| Precursor | $E_p$(peak I) | $E_p$(peak II) |
|---|---|---|
| 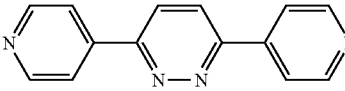 81 | −0.79 V | −0.91 V |
| 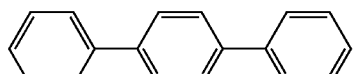 80 | −0.87 V | −1.06 V |
| 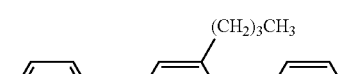 82 | −0.89 V | −1.08 V |
| 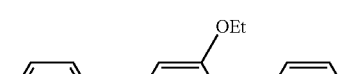 83 | −0.90 V | −1.02 V |
| 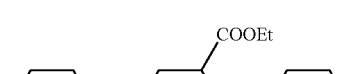 84 | −0.70 V | −1.11 V |
| 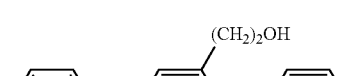 85 | −0.99 V | −1.18 V |

The number of electrons involved per reduction wave was determined by cyclic voltammetry by adding an internal reference (Red/Ox couple of which the number of electrons is known) to the solution. Ferrocenemethanol (Fc) was used as internal reference, the oxidation peak potential of said ferrocenemethanol being 0.28 V/SCE under the analytical conditions of the experiment (Scheme 91)

Scheme 91

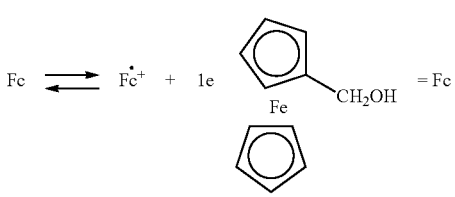

The analytical results confirm that the electroreduction of pyridinylpyridazines to pyrroles requires four electrons. The first two-electron transfer makes it possible to generate the dihydropyridazine intermediates (1,2- or 1,4-dihydropyridazines depending on their relative stability) and the second two-electron transfer brings about the extrusion of a nitrogen atom through the release of ammonia. The potential to be imposed for the preparative electrolyses should therefore lie at the level of the reduction waves corresponding at least to a four-electron reduction.

Example 7

Preparative Electrolysis of 3,6-bis-(pyridinyl)pyridazines

The preparative electrolyses of the various pyridazines (80-85) were carried out using, respectively, a working potential corresponding to the potential of the second reduction wave for the precursors. Said electrolyses were continued until complete disappearance of the precursors and until the consumption of an amount of charges (number of Coulombs) corresponding to the minimum amount of electrons necessary to induce rearrangement of said precursors to pyrrole (four electrons per mole of the substrate reduced).

Starting from virtually the same initial concentration ($10^{-4}$ M), the average time for complete disappearance of the precursors is about 5 to 6 hours. The pyrrole products 86, 87, 88, 89 and 90 were obtained with varying yields ranging from 60% to 90% (Scheme 92, Table 5).

Scheme 92

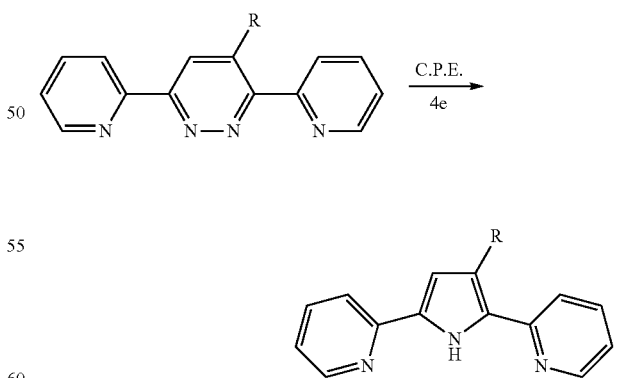

86 R = H
87 R = Bu
88 R = COOEt
89 R = EtO
90 R = (CH$_2$)$_2$OH

TABLE 5

| Precursor | $E_P$ (wave I) | $E_P$ (wave II) | $E_{imposed}$ | ne* | t (h) | PCE yield (pyrroles) | Chemical yield** |
|---|---|---|---|---|---|---|---|
| 80 | −0.87 V | −1.06 V | −1.00 V | 4.06 | 4 | 86 (82%) | 22% |
| 82 | −0.89 V | −1.08 V | −1.00 V | 4.53 | 6 | 87 (85%) | 18% |
| 83 | −0.90 V | −1.02 V | −1.00 V | 4.5 | 5.20 | 88 (75%) | 30% |
| 84 | −0.71 V | −1.12 V | −1.05 V | 5.66 | 6.25 | 89 (60%) | 32% |
| 85 | −0.99 V | −1.18 V | −1.10 V | 4.5 | 5.33 | 90 (92%) | 25% |

*number of electrons consumed/mol. of substrate reduced.
**Zn/AcOH

As indicated by the results, in all cases, the pyridazine ring regression in acetic buffer medium appears to be much more effective according to the electrochemical process than via the chemical process (Zn/AcOH) recommended in the literature.

These results are confirmed in the case of the pyridin-4-ylpyridazine 81, the transformation of which to the pyrrole 91 is performed with an 85% yield instead of 30% via the chemical process (Table 6).

TABLE 6

| Precursor | $E_P$ (wave I) | $E_P$ (wave II) | $E_{imposed}$ | ne* | t (h) | PCE yield (pyrroles) | Chemical yield** |
|---|---|---|---|---|---|---|---|
| 81 | −0.79 V | −0.91 V | −0.95 V | 3.77 | 4.6 | 91 (85%) | 30% |

*number of electrons consumed/mol. of substrate reduced.
**Zn/AcOH

The progression of the reactions by preparative electrolysis was controlled in each case by cyclic voltammetry directly in the cathode compartment on a vitreous carbon electrode, as illustrated by the voltammograms recorded during the electrolysis of the precursor 82 (FIG. 5, cyclic voltammograms during the preparative electrolysis of the precursor 82, —before electrolysis, —during electrolysis, —at the end of electrolysis, vitreous carbon electrode, v=100 mV/s).

The decrease in the intensity of the reduction wave (−1.08 V) for the precursor during the preparative electrolysis is correlated with the transformation during the electrosynthesis. Furthermore, said wave disappears completely at the end of electrolysis, thus making it possible to verify the total consumption of the precursor.

At the end of the electrolysis, voltammograms were also controlled (FIG. 6, voltammograms of the various pyrrole derivatives at the end of preparative electrolysis in the cathode compartment, vitreous carbon electrode, v=100 mV/s). They effectively show the disappearance of the two reduction waves, thereby confirming the mechanistic hypothesis proposed. The first wave is attributed to the two-electron reductions of the pyridazines to dihydropyridazines, and the second corresponds to the nitrogen extrusion so as to give the pyrrole rings.

Example 8

Preparative Electrolysis of 6,6'-dipicoline-4,4'-dimethyl-2-yl[3,3']-bipyridazine 105

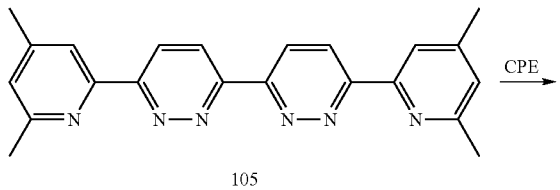

105

-continued

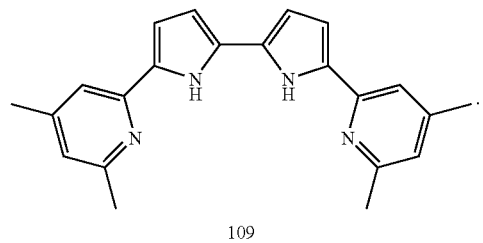

109

The solubility of the bipyridazine was improved by adding alkyl chains to the pyridine substituents (compound 105). It is then possible to solubilize this bipyridazine 105 under milder conditions than $H_2SO_4$ or acetic buffer media: a mixture of THF/acetic buffer (pH=4.6)/acetonitrile solvents. The voltammograms recorded under these conditions demonstrated three successive reduction waves at potentials $E_c$=−0.92 V, −1.03 V and −1.16 V (see FIG. 11).

The preparative electrolysis of the bipyridazine 105 at $E_T$=−1.05 eV made it possible to isolate the bipyrrole 109 with a yield of 35% (table below, entry 1). The results obtained confirm the hypothesis according to which the low yield obtained during the preparative electrolysis of the bipyridazine 105 is due to a degradation of the bipyrrole compound in sulfuric acid.

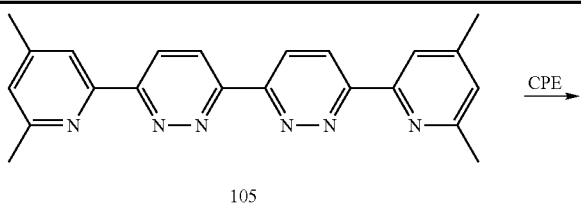

105

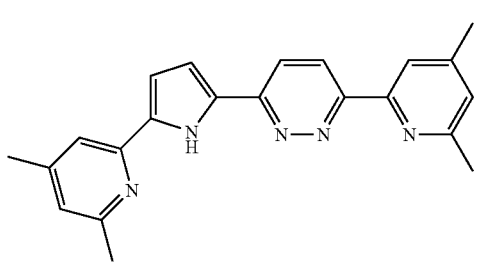

109

| Medium | Potential applied | Results |
|---|---|---|
| THF/acetic buffer pH = 4.6/acetonitrile: 50/45/50 | 1  $E_t = -1.05$ V, 10.3 e | Yield = 35% |
| | 2  $E_t = -1.15$ V. 8 e Halts for volts | Mixture of 2 unseparated compounds, including bipyrrole (109), traces |
| Polarogram Ec = −0.92 V, −1.03 V, −1.16 V | 3  $E_t = -1.15$ V, 10.1 e Without halting + 1 h pause at the end before extraction | Pyrrolepyridazine (110) 20% Pyrroletetrahydropyridazine (111) 20% |
| | 4  $E_t = -0.9$ V, 3.78 e, 40 min pause $E_t = -0.97$ V, 4 e, 40 min pause $E_t = -1.15$ V, 3.1 e, allowed to run overnight | NMR crude, degradation products: waste |

Several experiments were carried out at various potentials and under various conditions (table above, entries 2 to 4). Only one modification (entry 3) was found to be advantageous since it makes it possible to isolate two intermediates: the monopyrrole-pyridazine 110 and the monopyrrole-tetrahydropyridazine 111 with respective yields of 20%.

110

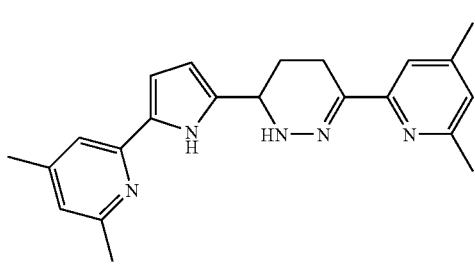

111

Example 9

Synthesis of 2,6-bis(6-(pyridin-2-yl)-pyridazin-3-yl)pyridine 33, N,N-donor

The ligand 33 was synthesized via a double Stille coupling, according to two different protocols (Retrosynthesis 2).

Pathway A: by the action of two equivalents of 2-tributylstannylpyridine 18 on the precursor 2,6-bis(3-chloropyridazin-6-yl)pyridine 32.

Pathway B: by condensation of two residues of 3-tributylstannyl-6-(pyridin-2-yl)pyridazine 30 with 2,6-dibromopyridine 31.

Retrosynthesis 2

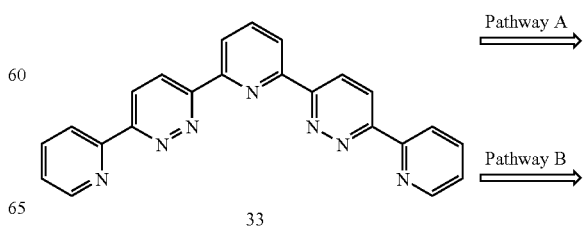

33

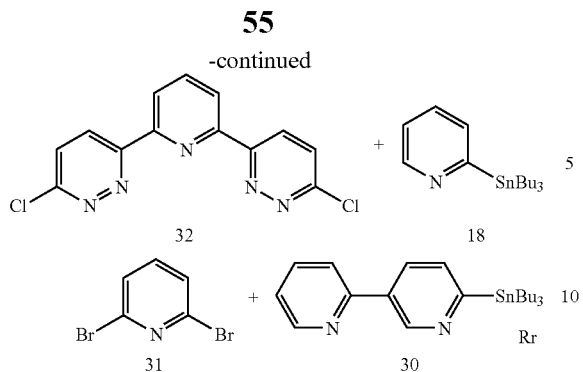

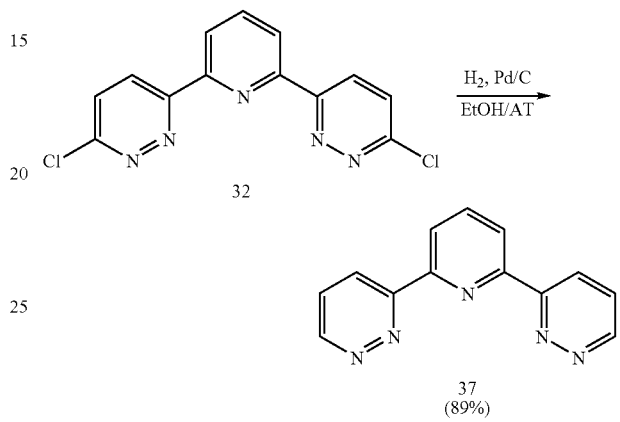

A third pathway, c, which is an alternative to pathway A, was also developed, using Negishi coupling in place of Stille coupling.

1. Pathway A

Preparation of the Precursor 2,6-bis(3-chloropyridazin-6-yl)pyridine 32

The dicarboxylate precursor 35 was generated in situ by condensation of the 2,6-diacetylpyridine 34 with two mol of glyoxylic acid (Scheme 13). The addition of two equivalents of hydrazine to the intermediate 35 at the reflux of acetic acid produces, by double cyclization, followed by dehydration, the 2,6-bis(6-2H-pyridazin-3-one)pyridine 36 with a yield of 75%.

pyridazine)pyridine 32 obtained is an α,α'-bifunctional tridentate ligand which enables an extension of the arrangement of the "pyridine-pyridazine" strand by coupling reactions. This opportunity obviously offers the possibility of subsequently preparing a variety of new heterocyclic sequences.

The reduction of the two "chloro" functions makes it possible to isolate the 2,6-bis(pyridazin-3-yl)pyridine 37, the structure of which is similar to that of 2,2';6',2''-terpyridine (Scheme 14). This reduction was carried out under a dihydrogen atmosphere, catalyzed by palladium-on-charcoal, with a yield of 89%.

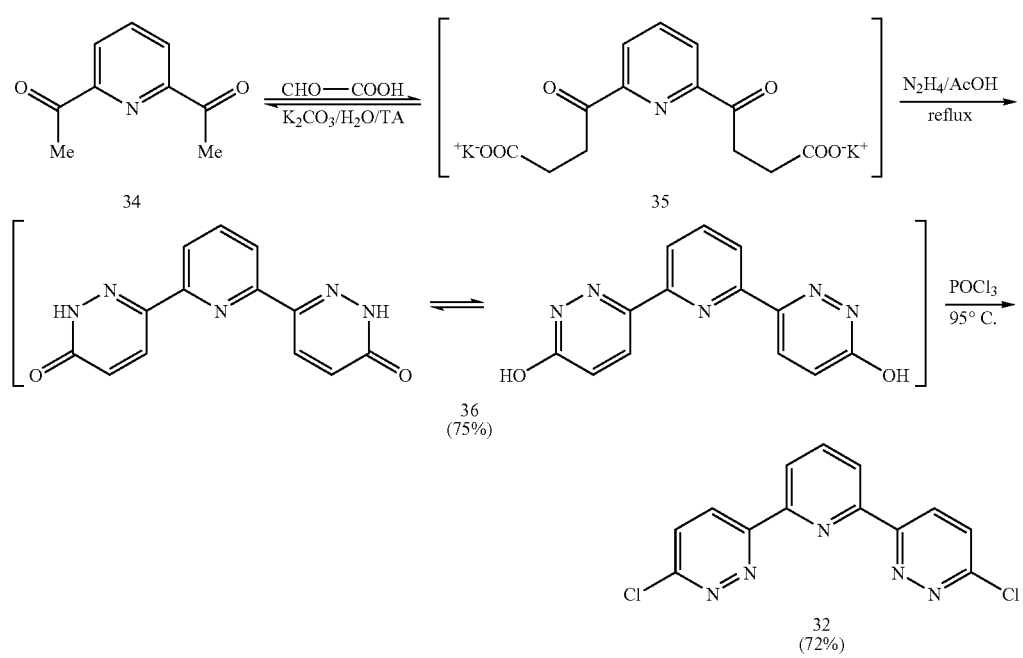

The dipyridazinone 36 can be in equilibrium in its tautomeric form. The ¹H NMR analysis (300 MHz) shows a broad singlet at around 11.38 ppm corresponding to the NH protons of the dione form 36.

The dipyridazinone 36 was subsequently treated with an excess of POCl₃ at 95° C., so as to produce the bis(chloropyridazinyl)pyridine 32, with a yield of 72%. The bis(chloro- Stille Coupling Starting from the 2,6-bis(3-chloropyridazin-6-yl)pyridine 32

The 2,6-bis[6-(pyridin-2-yl)pyridazin-3-yl]pyridine 33 was obtained, with a yield of 41%, by reacting two equivalents of 2-tributylstannylpyridine 18 with the precursor bis(chloropyridazinyl)pyridine 32, under the usual Stille coupling conditions [Pd(PPh$_3$)$_4$, reflux of toluene] (Scheme 15). This moderate yield can be explained by the weak reactivity of the precursor bis(chloropyridazinyl)pyridine 32 (effect of the pyridazine ring), and the dimerization product derived from the stannic pyridine 38 is isolated with a yield of 17%. According to this method, the ligand 33 was obtained in four steps with an overall yield of 22%.

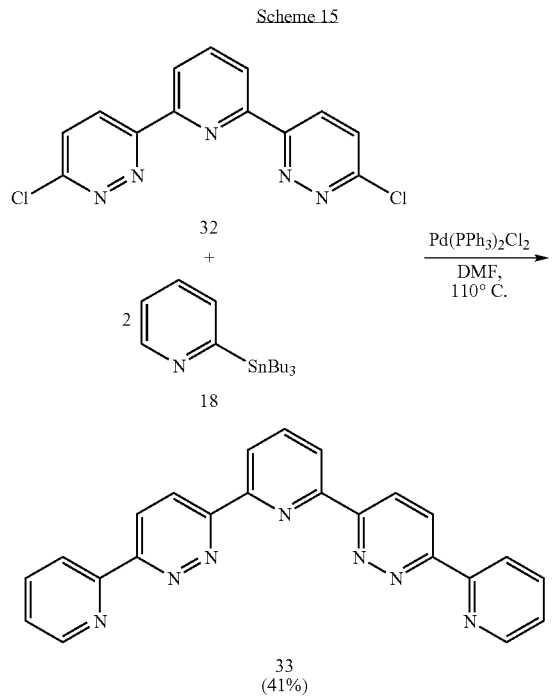

2. Pathway B

The condensation of two stannylated pyridinylpyridazine residues 39, with the 2,6-dibromopyridine 42, according to the conventional Stille coupling conditions (Pd(PPh$_3$)$_4$, reflux of toluene), also makes it possible to isolate the expected product 33 with a yield of 68% (Scheme 16). In this case, the use of the 2,6-dibromopyridine 42 favors the cross-coupling relative to the reaction of the dimerization and demetallation of the 3-tributylstannyl-6-(pyridin-2-yl)pyridazine 39. The product 33 was thus prepared in four steps with an overall yield of 32%.

Scheme 16

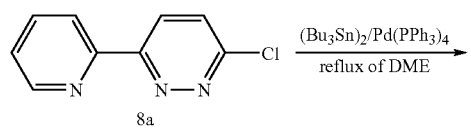

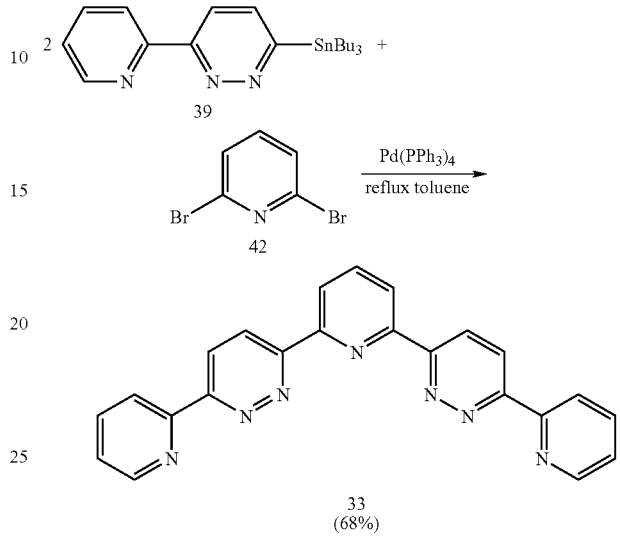

The monosubstituted intermediate, 3-(2-bromopyridin-6-yl)-6-(pyridin-2-yl)pyridazine 43, can also be predominantly isolated, with a yield of 72%, by starting from an equimolar mixture of the starting reactants (Scheme 17).

Scheme 17

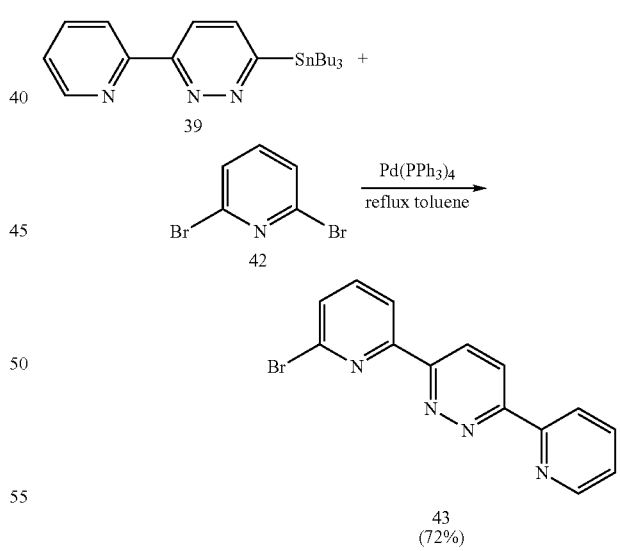

The latter halogenated derivative represents an intermediate of choice for gaining access to a large variety of heterogeneous ligands.

3. Pathway C

A condensation is first carried out between 2,6-diacetylpyridine (34) and two mol of glyoxylic acid. The addition of two mol of hydrazine and of acetic acid allows a double cyclization followed by a dehydration, and results in 2,6-bis(6-2H-pyridazin-3-one)pyridine (36) with a yield of 91%. This compound is subsequently treated with an excess of POCl₃ at reflux for 15 hours, so as to give bis(chloropyridazine)pyridine (32) with a yield of 48%. The Stille coupling is replaced with Negishi coupling. During the latter step, 2,6-bis[(pyridin-2-yl)pyridazin-3-yl]pyridine (33) was obtained with a yield of 17%, and 2,6-bis[6-(6-methylpyridin-2-yl)pyridazin-3-yl]pyridine (49) was obtained with a yield of 73%.

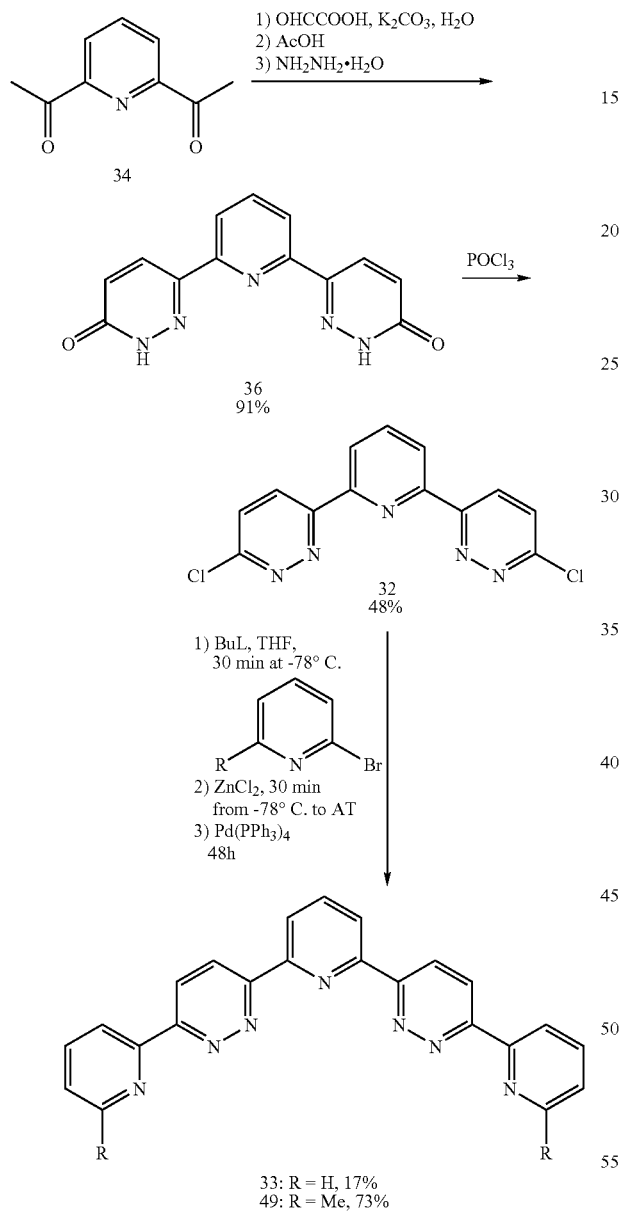

Example 10

Synthesis of 3-(2-carboxypyridin-6-yl)-6-(pyridin-2-yl)pyridazine 45

In order to introduce the monofunctionalization, the chloro(pyridyl)pyridazine 8a was chosen as precursor in the Stille coupling so as to react with the methylated stannylpyridine 22 (Scheme 19), in the equimolar presence of tetrakis(triphenylphosphine)palladium, so as to give exclusively the coupling product 44 with a yield of 90%.

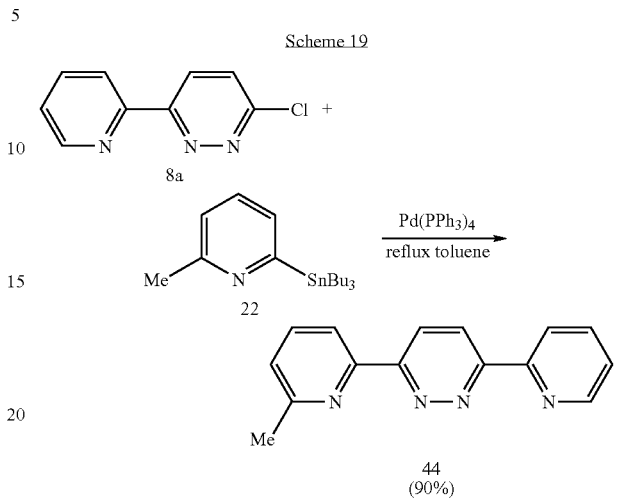

It should be noted that, in this case, no trace of bispyridine homocoupling product is observed in the reaction mixture.

The oxidation of the aromatic methyl in the α-position with respect to the pyridine nitrogen was carried out using selenium dioxide, at 150° C. in o-dichlorobenzene, and the 3-(2-carboxypyridin-6-yl)-6-(pyridin-2-yl)-pyridazine 45 was obtained with a yield of 74% (Scheme 20).

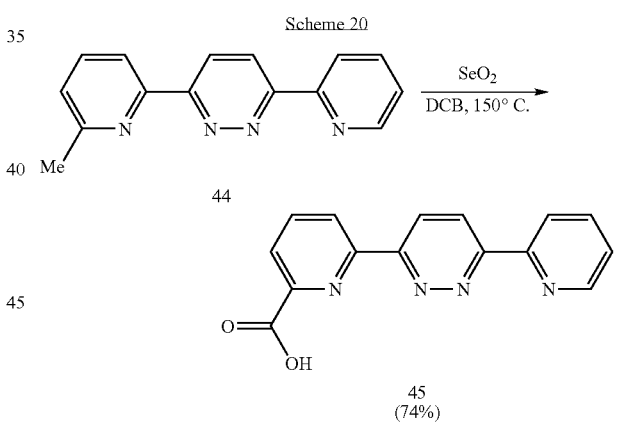

Example 11

Synthesis of the bis-tridentate diacid: 3,6-bis(2-carboxypyridin-6-yl)pyridazine 48

According to the same principle, the pyridazine diacid ligand 48 can be obtained by oxidation of the bis(di-methylpyridyl)pyridazine 47 (Scheme 21). The latter was prepared via a double Stille coupling between the 6-methyl-2-tributylstannylpyridine 22 and the 3,6-dichloropyridazine 46 in the presence of tetrakis(triphenylphosphine)palladium. In this case, a slight excess of stannylated pyridine (3 eq.) was used. Under the same oxidation conditions as previously, the 3,6-bis(2-carboxypyridin-6-yl)pyridazine acid 48 is isolated with a yield of 68%.

Scheme 21

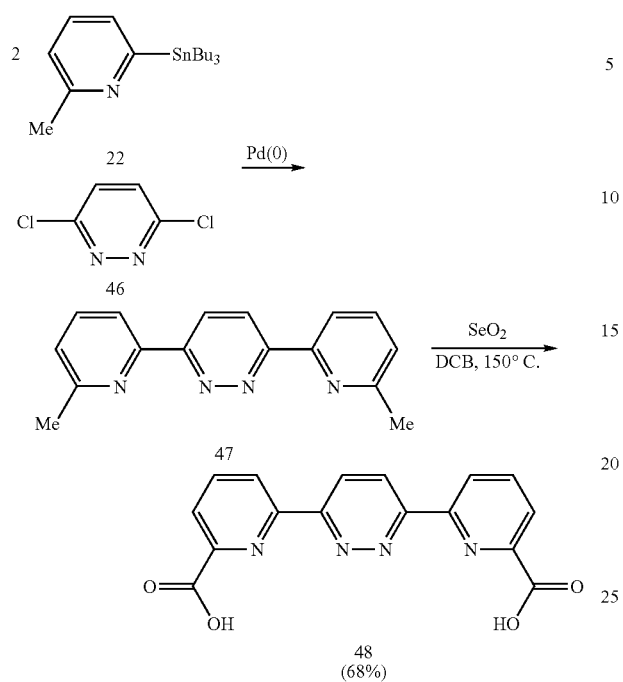

The pyridazine diacid 48 obtained is a bis-tridentate ligand: N-donating (pyridine and pyridazine) and O-donating (diacid). In this example, the presence of two adjacent nitrogen atoms in the pyridazine ring contributes to generating two distinct coordination sites.

Example 12

Synthesis of the 2,6-bis[3-(2-carboxypyridin-6-yl) pyridazin-6-yl]pyridine diacid 50: N—N- and/or N—O-donating tris-tridentate ligand The precursor of bis(chloropyridazinyl)pyridine 32 type can, by means of double Stille coupling [Pd(PPh$_3$)$_2$Cl$_2$, DMF, 110° C.], in the presence of two mol of 6-methyl-2-tributyl-stannylpyridine 22, lead to the 2,6-di[6-(6-methylpyridin-2-yl)pyridazin-3-yl]pyridine 49 (Scheme 22). The dimethylated ligand 49 was obtained with a yield of 53%.

Scheme 22

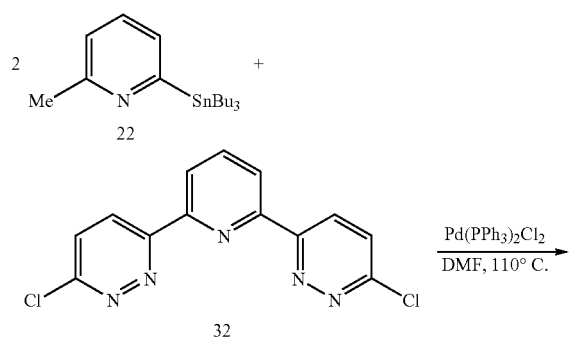

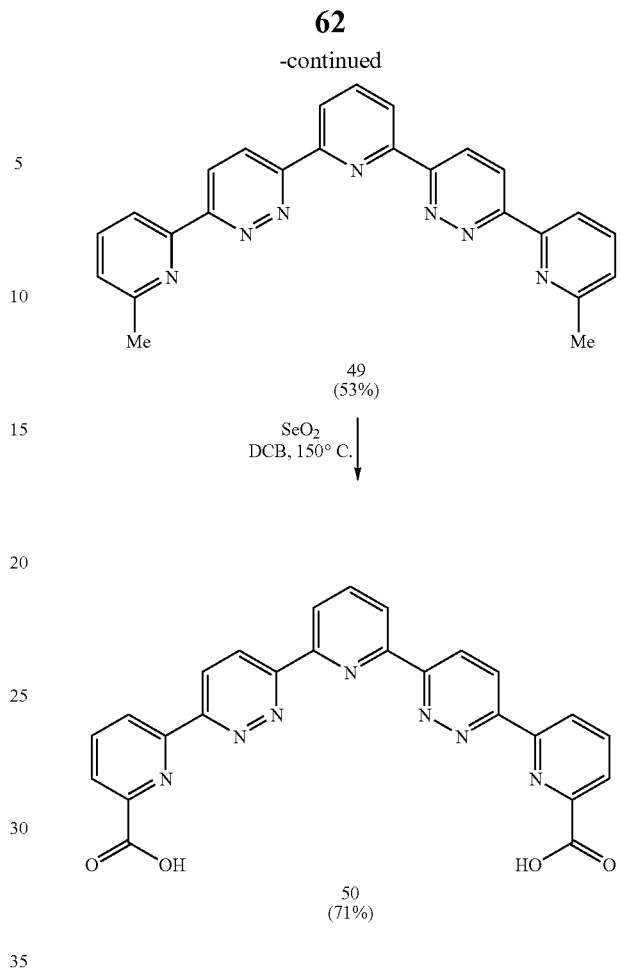

The oxidation of the bipyridazine 49 with selenium dioxide makes it possible to isolate the 2,6-di[3-(2-carboxypyridin-6-yl)pyridazin-6-yl]pyridine acid 50 with a yield of 71%.

The diacid 50 obtained is a ligand which has three coordination sites, a central site which is solely N-donating, and two symmetrical (N,O)-donating tridentate end sites. This compound can be converted to a cyclic ligand by introducing an ethereal alkyl chain using the two acid functions (via the ester or the acid chloride) (compound A below). This conversion, which can be generalized to all the compounds according to the invention having two end acid functions, enables a direct use in radioimmunotherapy, where (N,O)-donating heterogeneous cyclic ligands are highly desired.

A

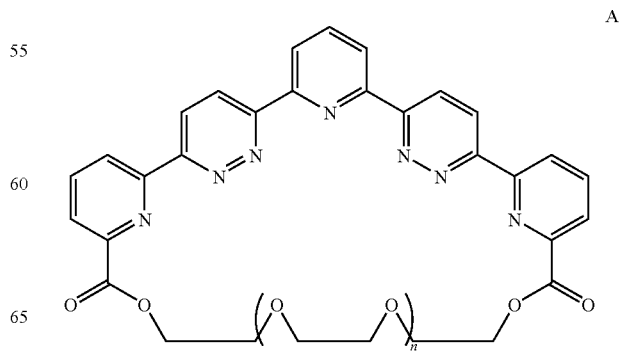

63
-continued

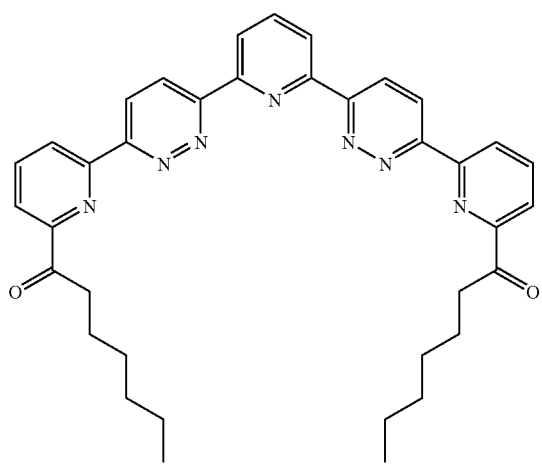

B

The inventors noted in particular that the diacid 50 exhibited capacities for complexation that is cation-selective, for example selective for cations of lanthanide type.

The introduction of hydrophobic (alkyl) chains makes it possible, moreover, to improve the solubility in an organic medium after complexation, for example in the context of a liquid-liquid extraction (compound B above). Conversely, a hydrophilic chain makes it possible to use these same ligands in an optionally aqueous medium.

Example 13

Synthesis of 6,6'-bis[6-(pyridin-2-yl)-pyridazin-3-yl]-2,2'-bipyridine 61

Two methods were explored for the synthesis of the 6,6'-bis[6-(2-pyridyl)pyridazin-3-yl]-2,2'-bipyridine 61, according to the retrosynthetic analysis 3.

Retrosynthesis 3

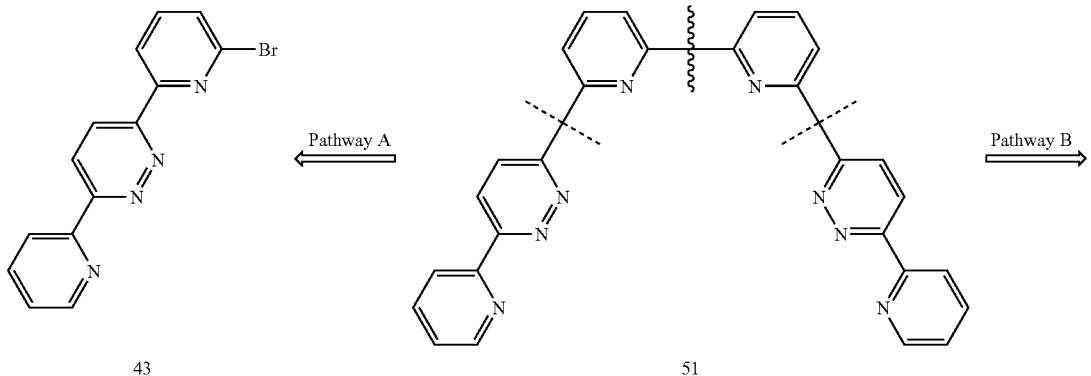

43

51

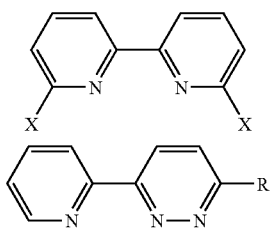

52b (X = Br) and 39 (R = SnBu₃)
or
60 (X = SnBu₃) and 8a (R = Cl)

The first approach (pathway A) was attempted via a homocoupling, of the 2-bromo-6-[3-(pyridin-2-yl)pyridazin-6-yl]pyridine 43, in the presence of a catalytic amount of NiBr$_2$(PPh$_3$)$_2$/Zn and of nBu$_4$NI, in DMF. This procedure did not make it possible to obtain the expected product. Such a result can be explained by the strong coordination potential of the polynitrogenous precursor, which traps the catalytic complex in situ.

The second method (pathway B) consisted in carrying out a double Stille coupling of two equivalents of pyridylpyridazine 39 or 8a, respectively, on α,α'-bisfunctional bipyridine precursors 52b or 60.

1. Synthesis of 6,6'-dihalo-2,2'-bipyridine 52a and 52b

The 6,6'-dichloro-2,2'-bipyridine 52a was synthesized by reacting 2-chloropyridine with a mixture of BuLi/Me$_2$N(CH$_2$)$_2$OLi as base for the regioselective lithiation at C-6 (Scheme 23). The 6-lithio-2-chloropyridine obtained appears to react with the starting chloropyridine so as to give the corresponding coupling product 52a with a yield of 47%.

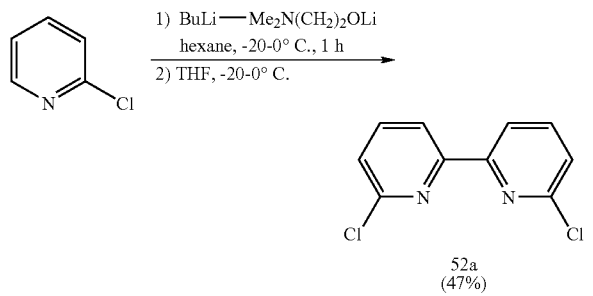

The 6,6'-dibromo-2,2'-bipyridine 52b was also obtained according to a similar procedure via monolithiation of the 2,6-dibromopyridine 42, followed by oxidative coupling, with a yield of 50% (Scheme 24).

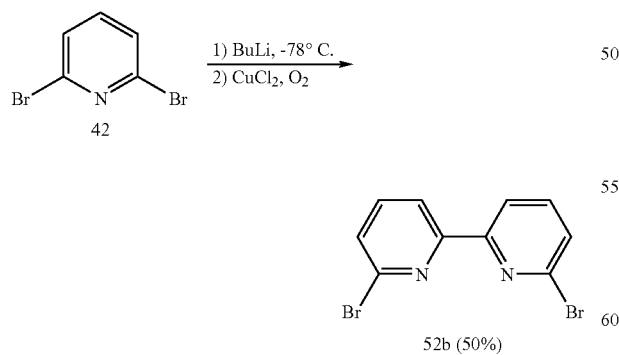

The 6,6'-dichloro-2,2'-bipyridine 52a can also be prepared via Stille heterocoupling between the 2-bromo-6-chloropyridine 55 and the 2-chloro-6-tributylstannylpyridine 56, with a yield of 35% (Scheme 25).

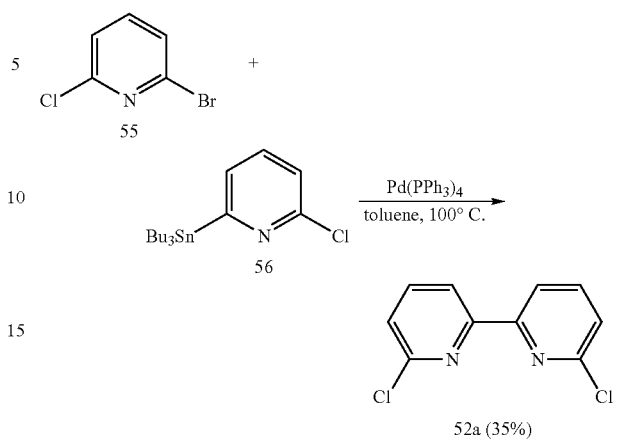

With the aim of improving the preparation of 6,6'-dihalo-2,2'-bipyridines, a different synthesis strategy was envisioned. This synthesis is made up of three steps starting from the 2-chloro-6-methoxypyridine 57; homocoupling of the 2-chloro-6-methoxypyridine 57, followed by hydrolysis of the 6,6'-methoxy groups of the dimer 58, then halogenation of the bipyridinone 59 obtained (Scheme 26).

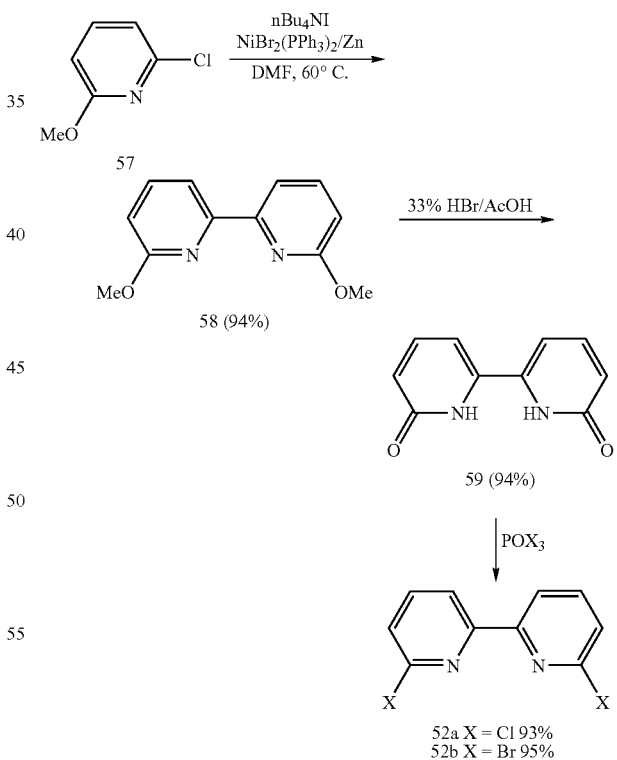

The 2-chloro-6-methoxypyridine 57 is homocoupled in the presence of a stoichiometric amount of a solution (1:0.3:1) of zinc, NiBr$_2$(PPh$_3$)$_2$ and nBu$_4$NI, in DMF at 55° C., so as to give the 6,6'-methoxy-2,2'-bipyridine 58 with a yield of 94%. The hydrolysis of the 6,6'-methoxy groups is carried out with a mixture of 33% of hydrobromic acid in acetic acid, at 95° C.

for 48 h, with a yield of 94%. The bipyridinone 59 treated with an excess of phosphorus oxychloride or of phosphorus oxybromide at 95° C., gives, respectively, the 6,6'-dichloro-2,2'-bipyridine 52a and the 6,6'-dibromo-2,2'-bipyridine 52b with virtually quantitative yields.

Bis-stannylation of 6,6'-dibromo-2,2'-bipyridine 52b

The reaction of the 6,6'-dibromo-2,2'-bipyridine 52b with hexabutyl distannane, in the presence of tetrakis(triphenylphosphine)palladium, makes it possible to isolate the bisstannylated bipyridine 60 with a yield of 86% (Scheme 27).

Scheme 27

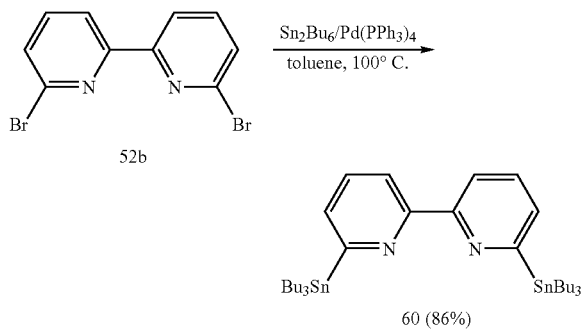

60 (86%)

2. Stille Coupling

This Stille coupling was also carried out in two different ways, either by reacting the brominated bipyridine 52b with two mol of stannylated pyridazine 39, or starting from the distannylated bipyridine 60 in the presence of two equivalents of chloro (or bromo) pyridazine 8a.

a—Starting from Distannic Bipyridine 60

Stille coupling of two mol of 3-chloro-6-(pyridin-2-yl) pyridazine 8a with the precursor 2,2'-bis(tributylstannyl)-6, 6'-bipyridine 60 gives the disubstituted product 61 with a yield of 68% (Scheme 28). In practice, a slight excess of chloropyridazine 8a is added in order for all the monosubstituted product formed to be consumed.

According to this procedure, the 6,6'-di[6-(pyridin-2-yl) pyridazin-3-yl]-2,2'-bipyridine 61 was prepared in seven steps with an overall yield of 30%.

Scheme 28

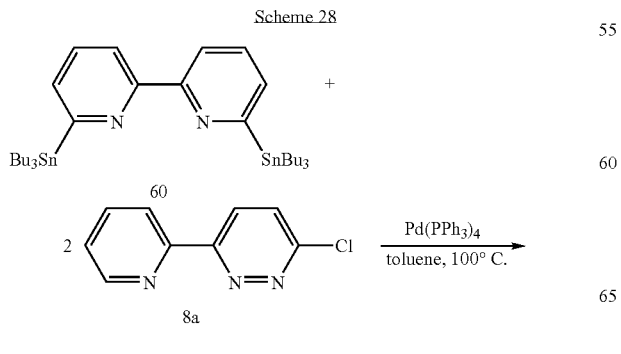

61 (68%)

b—Starting from the Dibrominated Bipyridine 52b

The condensation, according to Stille coupling, of two equivalents of 3-tributylstannyl-6-(pyridin-2-yl)pyridazine 39 with the dibrominated bipyridine precursor 52b gives the expected product 61 with a yield of 51% (Scheme 29).

By virtue of this method, also made up of seven steps, the 6,6'-di[6-(pyridin-2-yl)pyridazin-3-yl]-2,2'-bipyridine 61 was isolated with an overall yield of 23%.

Scheme 29

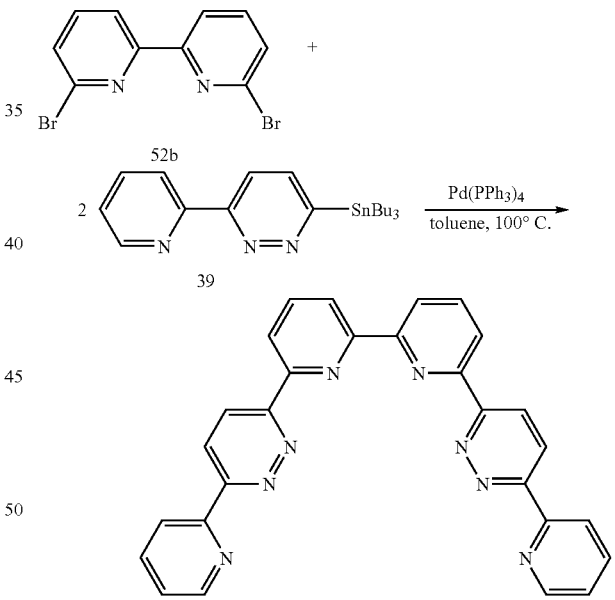

61 (51%)

Example 14

Synthesis of 2,9-di[6-(pyridin-2-yl)pyridazin-3-yl]-1,10-phenanthroline 66

The synthesis of the 2,9-dichloro-1,10-phenanthroline 65a consists of four steps, starting from the unsubstituted 1,10-phenanthroline 62 (Scheme 30).

Scheme 30

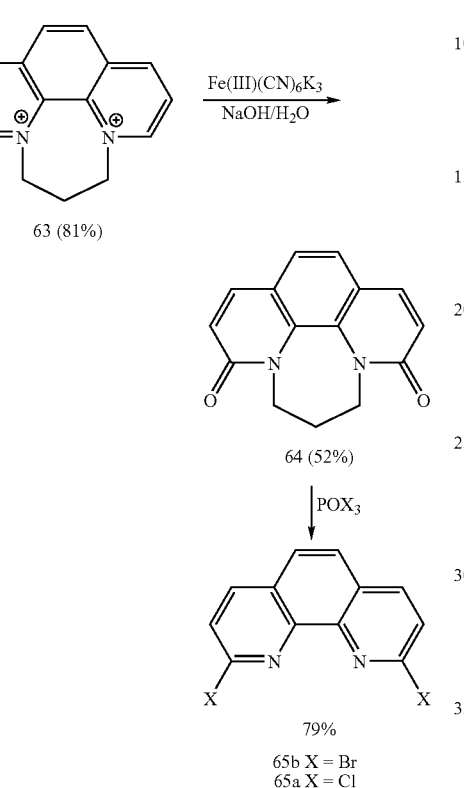

Stille Coupling

The rigid ligand 66 was obtained by Stille bis-coupling, by condensing two residues of tributylstannylpyridazine 39 with the 2,9-dibromo-1,10-phenanthroline 65b, with a yield of 91%, whereas its dichlorinated homolog 65a enables only a more modest yield of 62% to be obtained (Scheme 31).

Scheme 31

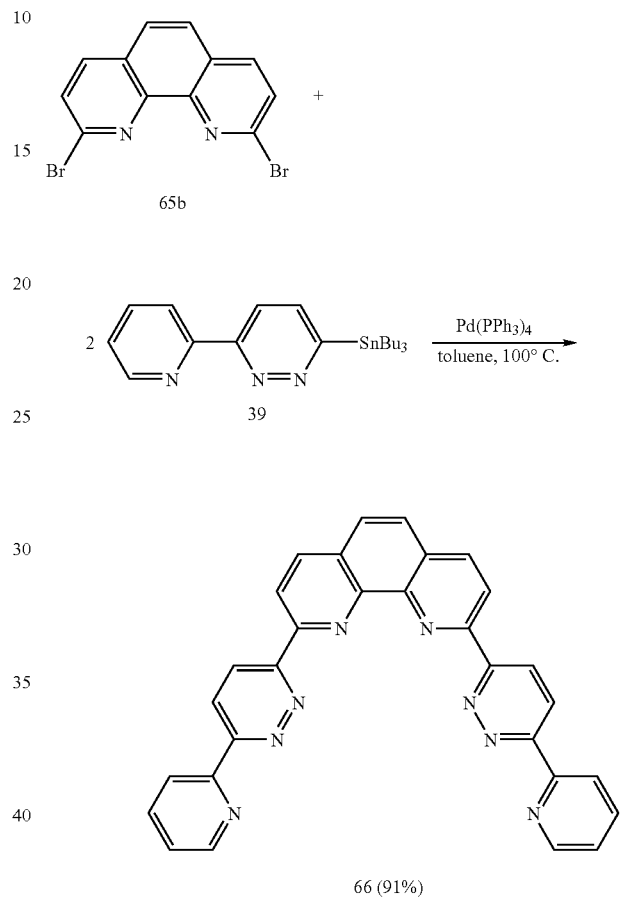

The N,N'-bridged dione 64 is the precursor of the 2,9-dihalo-1,10-phenanthrolines 65a and 65b. It can be prepared by regioselective oxidation of the 1,10-phenanthroline 62 after prior protection of the nitrogen doublets.

Electrophilic addition of 1,3-dibromopropane on the two nitrogens of the 1,10-phenanthroline 62, in nitrobenze at 120° C., makes it possible to isolate the quaternary ammonium salt of the 1,10-phenanthroline 63 with a yield of 81%. The oxidation of the salt 63 was carried out with potassium hexacyanoferrate in an alkaline aqueous solution of sodium hydroxide at 0° C. The N,N'-bridged dione 64 formed was isolated by silica gel chromatography with a yield of 52%. The α,α'-halogenation of the dione 64 follows the same mechanism of halogenation as in the case of the pyridazinone 16, or of the pyridinone 59, with spontaneous opening of the [N—(CH$_2$)$_3$—N] bridge through an aromaticity effect. The 2,9-dichloro-1,10-phenanthroline 65a and the 2,9-dibromo-1,10-phenanthroline 65b were obtained by heating at 95° C., respectively, in an excess of corresponding phosphorus oxyhalide, with a yield of 72% and 79%.

The 2,9-dihalo-1,10-phenanthrolines 65a and 65b represent precursors of choice for the synthesis of many rigid ligands analogous to the ligands prepared starting from 2,2'-bipyridine.

Example 15

Nonlinear Pyridazine Analog Ring Regression

Example of 2,9-di[6-(pyridin-2-yl)pyridazin-3-yl]-1,10-phenanthroline 66

The bipyridazine structure 66 was subjected to the electrochemical ring regression conditions. The electroreduction experiment was carried out in a sulfuric acid medium. The voltammogram of the 2,9-di[6-(pyridin-2-yl)pyridazin-3-yl]-1,10-phenanthroline 66 clearly indicates a very marked reduction peak at a potential of −0.63 V/SCE (FIG. 7, cyclic voltammograms during the preparative electrolysis of the precursor (—before electrolysis, —during electrolysis—at the end of electrolysis; vitreous carbon electrode, v=100 mV/s).

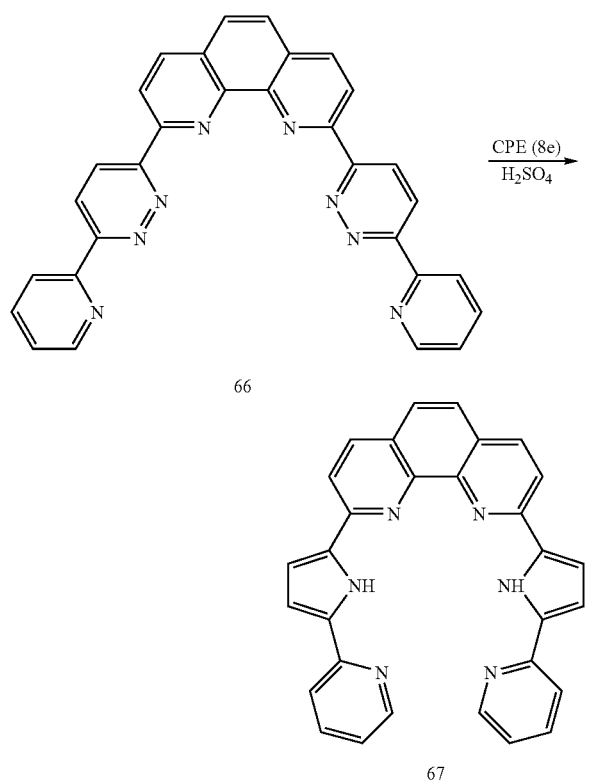

66

67

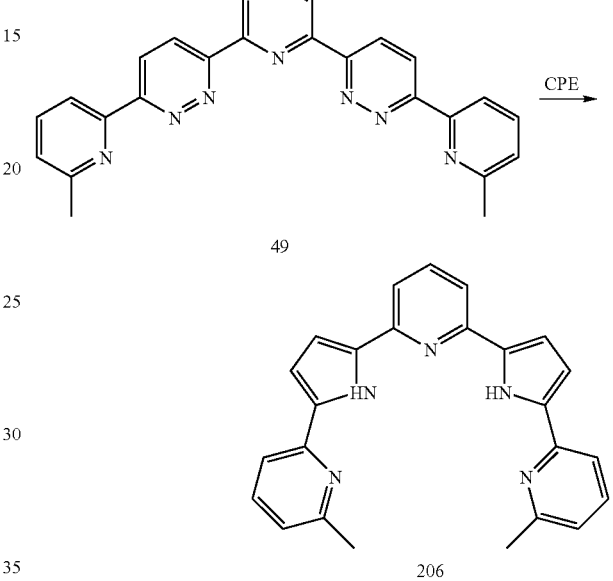

49

206

The wave corresponds to a potential of a simultaneous 4-electron reduction (4 electrons per pyridazine ring). The formation of the corresponding dipyrrole 67 thus logically requires the input of at least 8 electrons per mole of bipyridazine 66.

The preparative electrolysis of this compound in a sulfuric medium was therefore carried out by applying a working potential of −0.5 V/SCE for one hour (Q=239 C) and was then continued at a potential of −0.8 V/SCE until almost total consumption of the precursor (Q=323 C). This preparative electrolysis was monitored by cyclic voltammetry directly in the cathode compartment on a carbon electrode at various stages of the electrosynthesis. A decrease in the intensity of the reduction wave for the bipyridazine compound 66 on the various voltammograms clearly shows the reduction of said compound during the preparative electrolysis. The latter was halted after complete disappearance of this wave (experiment lasting 10 h), during which time at least 8 electrons were therefore consumed.

The identification of 2,9-di[5-(pyridin-2-yl)pyrrolo-2-yl]-1,10-phenanthroline 67 was confirmed by its mass spectrum, m/z=[M] 464. The analysis of the $^1$H NMR spectrum of the dipyrrole indicates the presence of 2 NH at δ=10.94 ppm and of 4 pyrrole protons between δ=6.70-6.90 ppm ($^3$J=3.9 Hz). The latter also couple with the NH of the pyrroles, with respective coupling constants $^4$J of 2.5 Hz and 2.8 Hz.

Optimum formation of the bipyrrole is provided according to the experimental protocol selected for this electroreduction experiment, in which 8 electrons per mole were consumed.

Example of 2,6-bis[6-(6-methylpyridin-2-yl)pyridazin-3-yl]pyridine 49

The preliminary preparative electrolysis results showed that it was advantageous to have compounds sufficiently soluble to allow the electrochemical reduction reaction under the mildest possible conditions. The electrochemical regression was therefore carried out with the 2,6-bis[6-(6-methylpyridin-2-yl)pyridazin-3-yl]pyridine 49, which is soluble under these conditions.

1. Preparative Electrolysis of the 2,6-bis[6-(6-methylpyridin-2-yl)pyridazin-3-yl]pyridine 49 in a 0.5M H$_2$SO$_4$ Medium The voltammograms recorded in 0.5M sulfuric acid demonstrated three successive reduction waves at potentials $E_c$=−0.551 V, −0.774 V and −1.053 V.

In a 0.5M H$_2$SO$_4$ medium, the reaction for preparative electrolysis of the bipyridazine 49 carried out electrochemically was performed at a working potential $E_t$=−0.9 V/SCE until consumption of 8 electrons. The reaction is monitored by cyclic voltammetry and TLC. At the end of the reaction, the bipyrrole 206 was isolated with a yield of 10%, which is probably due to a phenomenon of degradation of the bipyrrole compound in a very acidic medium.

2. Preparative Electrolysis of the 2,6-bis[6-(6-methylpyridin-2-yl)pyridazin-3-yl]pyridine 49 in an acetic acid buffer medium, pH=4.6

The voltammograms (see FIG. 9) recorded in the THF/acetic buffer (pH=4.6)/acetonitrile mixture, starting from the 2,6-bis[6-(6-methylpyridin-2-yl)-pyridazin-3-yl]pyridine 49, demonstrated two successive four-electron reduction waves (light) corresponding to potentials $E_c$=−0.959 V and −1.190 V. Under the same conditions, the bipyrrole compound 206 showed a wave corresponding to the reduction of the pyrroles (dark) with a potential $E_c$=−1.436 V.

In a THF/acetic buffer (pH=4.6)/acetonitrile medium, the reaction for preparative electrolysis of the bipyridazine 49 carried out electrochemically was performed at a working potential $E_t$=−1.2 V/SCE until consumption of 8 electrons. The reaction is monitored by cyclic voltammetry and TLC.

The reaction for preparative electrolysis of the bipyridazine 49 carried out electrochemically was performed in a THF/acetic buffer (pH=4.6)/acetonitrile medium on a working electrode with a layer of mercury, at a potential $E_t$=−1.2 V/SCE until consumption of 8 electrons. The reaction is monitored by cyclic voltammetry and TLC. The preparative electrolysis of the bipyridazine 49 made it possible to isolate the bipyrrole 206 as the sole reaction product, with an optimizable yield of 45%.

The two results are summarized in the following table

| Medium | Potential applied | Results |
| --- | --- | --- |
| H$_2$SO$_4$ medium<br>Ec = −551 mV,<br>−774 mV,<br>−1.053 V | $E_t$ = −0.90 V, 8 e | Yield = 10% |
| THF/acetic buffer<br>pH = 4.6/acetonitrile<br>medium 50/45/5<br>Ec = −0.99 V and<br>−1.190 V | $E_t$ = −1.2 V, 8.27 e | Yield = 45% |

Synthesis of the Compounds Obtained by Ring Regression by Nitrogen Extrusion Carried Out Electrochemically:

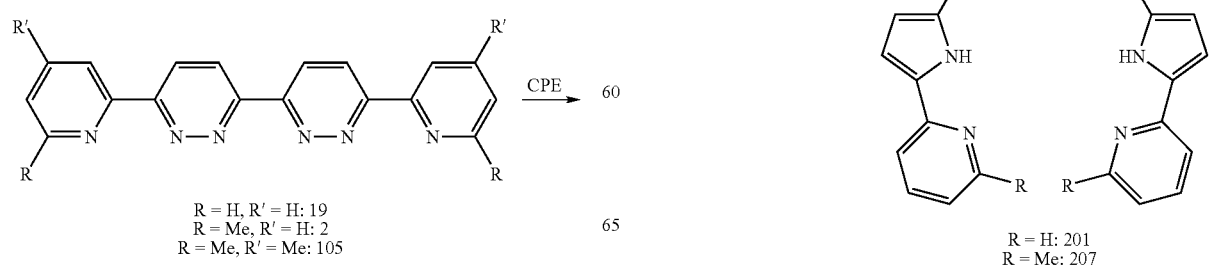

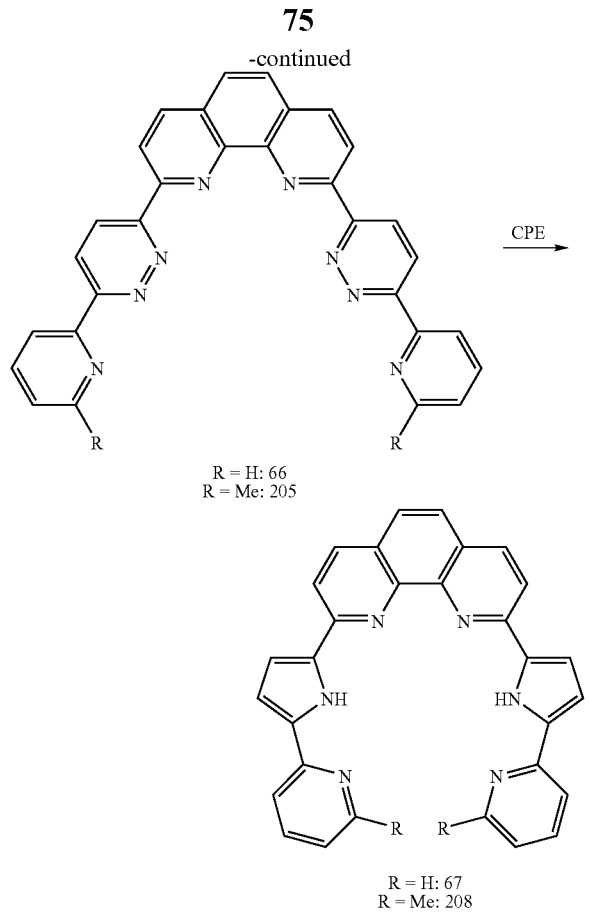

R = H: 66
R = Me: 205

R = H: 67
R = Me: 208

Example 16

Preparation of the Ethers of di(6-pyridin-2-yl)pyridazine, via the 6-(pyridin-2-yl)-2H-pyridazin-3-one 4, and of the 6-(pyridin-2-yl)-2H-pyridazine-3-thione 10

The condensation of glyoxylic acid with the 2-acetylpyridine 4 is carried out according to an aldolization in a basic medium (potassium carbonate) (Scheme 3) (Coates and McKillop, 1992). This step was optimized from 31% to 65% by simply increasing the number of equivalents of the base to 3 eq., whereas the yield from this condensation drops in a more basic medium of potassium hydroxide (Coates and McKillop, 1992). The potassium 2-hydroxy-4-oxo-4-(pyridin-2-yl)butanoate 5 obtained subsequently becomes cyclized, at the reflux of acetic acid in the presence of hydrazine monohydrate, so as to form the intermediate 6 which becomes dehydrated in situ so as to give the 6-(pyridin-2-yl)-2H-pyridazin-3-one 7 with an overall yield of 65%.

The $^1$H NMR analysis (300 MHz) of the 6-(pyridin-2-yl)-pyridazin-3-one 7 reveals two doublets for $C_4$—H and $C_5$—H (J=9.6 Hz and J=9.9 Hz), respectively at 7.01 and 8.27 ppm, and a broad singlet for the proton (NH) at 13.32 ppm.

The chlorination, or the bromination, of the pyridazinone 7 is a conventional reaction carried out, respectively, in an excess of phosphorus oxychloride or phosphorus oxybromide, at 100° C., so as to give the 3-halopyridazines 8a and 8b, with virtually quantitative yields.

Scheme 100

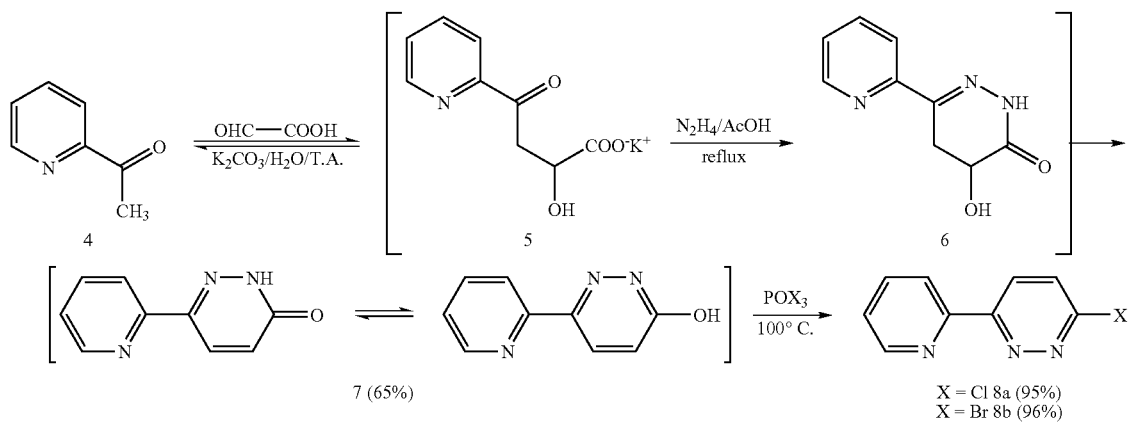

The reaction of the chloropyridazine 8a and of the pyridazinone 7, in the presence of a strong base (sodium hydride), in DMSO, gives the original ethereal product 9 with a yield of 80% (Scheme 4).

Scheme 4

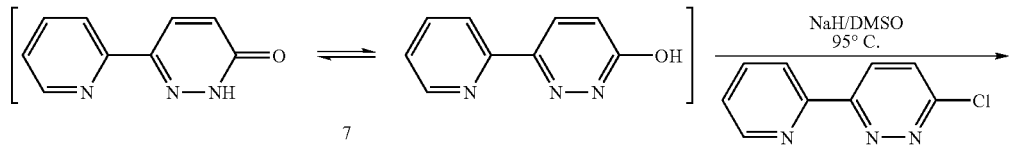

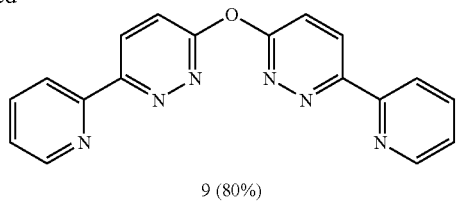

9 (80%)

The $^1$H NMR analyses (300 MHz) show, surprisingly, a resolving of all the signals appearing to indicate a distribution of 12 distinct protons (FIG. 8). This observation could possibly be linked to the existence, in solution, of a dimeric structure, which is nonsymmetric, induced by intermolecular hydrogen bonds, via a molecule of water for example. It will only be possible to verify this argument from the crystalline structure of the molecule, since the electron impact mass spectrum of the product 9 clearly confirms the characterization of an ether-oxide monomer 9 (M+328).

The 3,3'-di[6-(pyridin-2-yl)]pyridazine thioether 11 was also prepared by coupling the 6-(pyridin-2-yl)-2H-pyridazine-3-thione 10 and the 3-chloro-6-(pyridin-2-yl)pyridazine 8a, in the presence of a strong base (NaOH) in DMSO (Scheme 6). The pyridazinethione 10 was prepared previously by reacting phosphorus pentasulfide with the 6-(pyridin-2-yl)-2H-pyridazin-3-one 7 with a yield of 92%.

Scheme 6

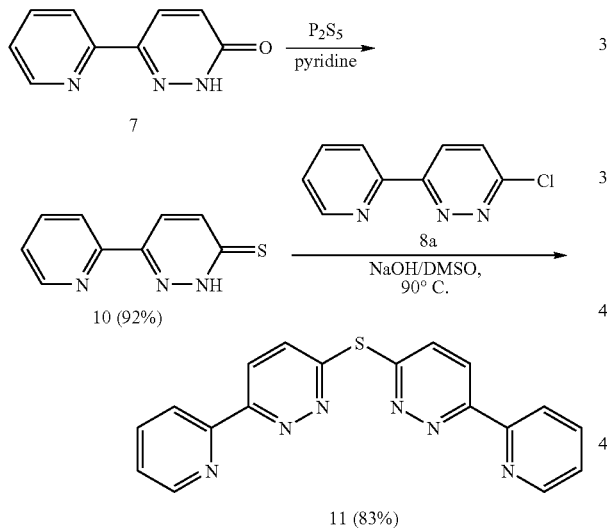

11 (83%)

Example 17

6,6'-bis(6-methylpyridin-2-yl)-3,3'-bipyridazine 2

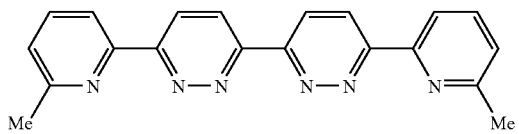

$C_{20}H_{16}N_6$
M = 340.38
Yield = 83%
Yellowish powder
Mp > 260° C.

The 6,6'-bis(6-methylpyridin-2-yl)-3,3'-bipyridazine 2 is obtained according to the general Stille coupling procedure, starting from a reaction mixture of 500 mg (2.21 mmol) of dichlorobipyridazine 17, 2.46 g (6.63 mmol) of 2-methyl-6-tributylstannylpyridine 22, 155 mg (0.221 mmol) of dichlorobis(triphenylphosphine)-palladium(II), and 40 ml of freshly distilled DMF. The reaction mixture is heated at 95-105° C. for 24 h, and the residue obtained is purified by silica gel chromatography (eluent: ethyl acetate/petroleum ether=1/9). The disubstituted product 2 is isolated with a yield of 83%.

Alternatively, the purification of the product 2 can be obtained by decomplexation in a saturated aqueous solution of cold potassium cyanide or of EDTA for at least two hours, after the heating for 24 h mentioned above.

This decomplexation can also be carried out by mixing the product 2 with 40 ml of a saturated aqueous solution of potassium fluoride. The organic phase is subsequently washed with NaHCO$_3$, followed by extraction with CHCl$_3$. The organic phase is dried over MgSO$_4$, filtered and concentrated. Washing with 3 times 150 ml of 1M HCl is applied, and the aqueous phases are combined. After filtration, the mixture is neutralized with Na$_2$CO$_3$ and the precipitate formed 2 is then filtered off.

$^1$H NMR (CDCl$_3$) δppm: 2.66 (s, 6H, CH$_3$); 7.27 (d, 2H, J=8.1, H$_{pyridine}$): 7.79 (t, 2H, J=7.8, H$_{pyridine}$); 8.55 (d, 2H, J=8.1, H$_{pyridine}$); 8.80 (d, 2H, J=9.0, H$_{pyridazine}$); 8.97 (d, 2H, J=9.0, H$_{pyridazine}$).

$^{13}$C NMR (CDCl$_3$) δppm: 24.60, 118.76, 124.58, 125.30, 125.41, 137.36, 152.36, 155.90, 158.49, 159.20.

MS, m/z (I %): 340 (M$^+$, 100%), 312 (M$^+$−2CH$_3$, 49%), 283 (M$^+$−(2CH$_3$+N$_2$), 32%).

Example 18

6-(pyridin-2-yl)-2H-pyridazin-3-one 7

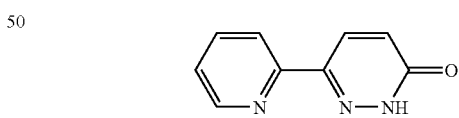

$C_9H_7N_3O$
M = 173.17
Yield = 65%
Brown powder

In a 250 ml three-necked round-bottomed flask equipped with a condenser and a dropping funnel, 17 g (120 mmol) of K$_2$CO$_3$ and 3.8 g (41.5 mmol) of glyoxylic acid monohydrate are dissolved in 50 ml of water. After cooling to 0° C., 5 g (41.5 mmol) of 2-acetylpyridine 4 are added. The reaction mixture is stirred for 2.5 h at ambient temperature and then again cooled to 0° C. After the successive addition of 17.5 ml of acetic acid dropwise and 2.5 ml (41.5 mmol) of hydrazine monohydrate, the mixture is stirred at reflux for 2 h. After cooling to 0° C., and neutralization with K₂CO₃, the precipitate obtained is filtered off, and washed with water and then with isopropanol. The pyridazinone 7 is obtained with a yield of 65%.

$^1$H NMR (DMSO-d$_6$) δppm: 7.01 (d, 1H, J=9.6, H$_{pyridazine}$); 7.42-7.46 (m, 1H, H$_{pyridine}$); 7.91-7.93 (m, 1H, H$_{pyridine}$); 8.04 (d, 1H, J=8.1, H$_{pyridine}$); 8.27 (d, 1H, J=9.9, H$_{pyridazine}$); 8.64 (d, 1H, J=4.8, H$_{pyridine}$); 13.32 (sl, 1H, NH).

$^{13}$C NMR (DMSO-d$_6$) δppm: 118.79, 123.49, 129.34, 130.08, 136.83, 142.89, 148.50, 151.25, 160.09.

MS, m/z (I %): 173 (M$^+$, 71%), 145 (M$^+$–N$_2$, 10%), 117 (M$^+$–CCONH$_2$, 100%).

Example 19

3-chloro-6-(pyridin-2-yl)pyridazine 8a

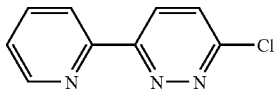

C$_9$H$_6$ClN$_3$
M = 191.62
Yield = 95%
Yellowish crystals 4 g of pyridinylpyridazinone 7 dissolved in an excess (40 ml) of phosphorus oxychloride are refluxed for 8 hours. After cooling, the reaction mixture is poured into 250 ml of ice-cold water and then neutralized, dropwise, with a saturated aqueous solution of NaHCO₃. After extraction with dichloromethane (5×100 ml), the organic phase is dried over MgSO₄ and then concentrated under reduced pressure, to give the chlorinated pyridazine 8a with a yield of 95%.

$^1$H NMR (CDCl$_3$) δppm: 7.37-7.42 (ddd, 1H, J=1.2, 4.5, 7.5, H$_{pyridine}$); 7.63 (d, 1H, J=9.0, H$_{pyridazine}$); 7.89 (dt, 1H, J=1.8, 7.8, H$_{pyridine}$); 8.55 (d, 1H, J=9.0, H$_{pyridazine}$); 8.64 (d, 1H, J=8.7, H$_{pyridine}$); 8.71 (d, 1H, J=4.5, H$_{pyridine}$).

$^{13}$C NMR (CDCl$_3$) δppm: 121.49, 124.95, 126.87, 128.63, 137.18, 149.38, 152.31, 156.78, 157.78.

MS, m/z (I %): 191 (M$^+$, 28%), 163 (M$^+$–N$_2$, 5%), 128 (M$^+$–(N$_2$+Cl), 100%).

Example 20

3-bromo-6-(pyridin-2-yl)pyridazine 8b

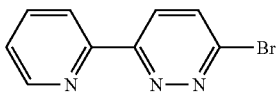

C$_9$H$_6$BrN$_3$
M = 236.07
Yield = 75%
Yellowish crystals 1 g (5.78 mmol) of 6-(pyridin-2-yl)-2H-pyridazin-3-one 7 and an excess (5 g) of phosphorus oxybromide are refluxed for 12 hours. The reaction mixture is poured into 100 ml of ice-cold water and then neutralized, dropwise, with a saturated aqueous solution of NaHCO₃. After extraction with dichloromethane (3×30 ml) the organic phase is dried over MgSO₄ and then concentrated under reduced pressure, to give the brominated pyridazine 8b with a yield of 75%.

$^1$H NMR (CDCl$_3$) δppm: 7.39-7.43 (ddd, 1H, J=0.9, 6.0, 7.5, H$_{pyridine}$); 7.76 (d, 1H, J=8.7, H$_{pyridazine}$); 7.88 (dt, 1H, J=1.8, 5.2, H$_{pyridine}$); 8.44 (d, 1H, J=8.7, H$_{pyridazine}$); 8.63 (d, 1H, J=8.1, H$_{pyridine}$); 8.70 (m, 1H, H$_{pyridine}$).

$^{13}$C NMR (CDCl$_3$) δppm: 121.55, 125.08, 126.61, 132.01, 137.27, 148.35, 149.47, 152.48, 160.00.

MS, m/z (I %): 237 (M$^+$+H, 23%), 235 (M$^+$–H, 22%), 128 (M$^+$–(Br+N$_2$), 100%).

Example 21 di(6-pyridin-2-yl)pyridazine ether 9

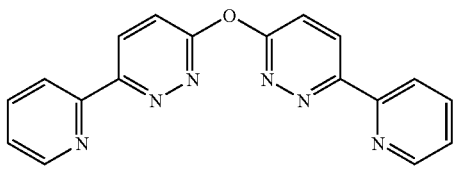

C$_{18}$H$_{12}$N$_6$O
M = 228.33
Yield = 80%
Yellowish powder
Mp = 226° C.

In a 50 ml round-bottomed flask, 300 mg (1.73 mmol) of pyridazinone 7 and 83 mg (3.46 mmol) of sodium hydride are dissolved in 15 ml of DMSO. The mixture is stirred for 15 minutes at 90° C. before adding 335 mg (1.73 mmol) of chloropyridazine 8a and stirring at the same temperature for 4 h. After cooling and extraction with dichloromethane, the organic phase is dried with MgSO₄ and concentrated under reduced pressure. The solid residue is purified by silica gel chromatography (eluent:ethyl acetate/petroleum ether=6/4), to give the ether 9, with a yield of 80%.

$^1$H NMR (CDCl$_3$) δppm: 7.20 (d, 1H, J=9.9, H$_{pyridazine}$); 7.34 (ddd, 1H, J=1.2, J=5.1, J=7.5, H$_{pyridine}$); 7.43 (ddd, 1H, J=0.9, J=5.4, 7.5, H$_{pyridine}$); 8.77 (dt, 1H, J=1.5, J=8.1, H$_{pyridine}$); 7.91 (dt, 1H, J=0.9, J=8.7, H$_{pyridine}$); 8.09 (d, 1H, J=9.9, H$_{pyridazine}$); 8.24 (d, 1H, J=8.1, H$_{pyridine}$); 8.53 (d, 1H, J=9.9, H$_{pyridazine}$); 8.67 (m, 1H, H$_{pyridine}$); 8.75 (m, 3H, 1H$_{pyridazine}$, 2H$_{pyridine}$).

$^{13}$C NMR (CDCl$_3$) δppm: 120.81, 121.89, 124.39, 125.03, 125.70, 125.85, 130.91, 131.75, 136.98, 137.24, 145.47, 149.06, 149.55, 151.63, 152.75, 156.97, 158.58, 159.93.

MS, m/z (I %): 328 (M$^+$, 100%), 299 (M$^+$–N$_2$, 23%), 271 (M$^+$–2N$_2$, 29%), 250 (M$^+$–Py, 38%).

HRMS
Exact mass calculated [M+H]=329.1151
Exact mass found [M+H]=329.1146

Example 22

6-(pyridin-2-yl)-2H-pyridazine-3-thione 10

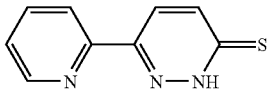

C$_9$H$_7$N$_3$S
M = 189.24
Yield = 92%
Yellowish-green powder 500 mg (2.9 mmol) of pyridazinone 7 and 772 mg (3.5 mmol) of phosphorus pentasulfide are dissolved in 20 ml of anhydrous pyridine. The reaction mixture is brought to reflux for 18 h, and then cooled to ambient temperature. It is then poured into 200 ml of water, and the precipitate thus formed is filtered off and then washed with ice-cold water. The pyridazinethione 10 is obtained with a yield of 92%.

$^1$H NMR (CDCl$_3$) δppm: 7.37-7.39 (m, 1H, H$_{pyridine}$); 7.81-7.84 (m, 2H, H$_{pyridine}$, H$_{pyridazine}$); 8.15 (d, 1H, J=7.5, H$_{pyridine}$); 8.23 (d, 1H, J=8.7, H$_{pyridazine}$); 8.68 (d, 1H, J=4.2, H$_{pyridine}$); 12.34 (bs, 1H, NH).

$^{13}$C NMR (CDCl$_3$) δppm: 120.08, 120.53, 120.55, 124.85, 137.14, 137.16, 137.53, 141.53, 149.36.

MS, m/z (I %): 189 (M$^+$, 100%), 160 (M$^+$, 35%).

Example 23 di(6-pyridin-2-yl)pyridazine thioether 11

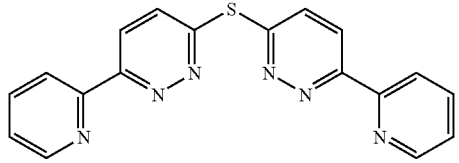

C$_{18}$H$_{12}$N$_6$S
M = 244.39
Yield = 83%
White powder
Mp = 182° C.

A solution of 200 mg (1.06 mmol) of pyridazinethione 10 and 40 mg (1.27 mmol) of sodium hydroxide in DMSO (15 ml) is stirred for 15 minutes at a temperature of 90° C. 222 mg (1.16 mmol) of chloropyridazine 8a are added and the reaction medium is stirred for 3 h at 90° C. After cooling and extraction of the mixture with dichloromethane, the organic phase is dried with MgSO$_4$ and concentrated under reduced pressure. The solid residue obtained is purified by silica gel chromatography (eluent: ethyl acetate/petroleum ether=6/4). The product 11 is obtained with a yield of 83%.

$^1$H NMR (CDCl$_3$) δppm: 7.37-7.42 (m, 2H, H$_{pyridine}$); 7.84-7.92 (m, 4H, H$_{pyridine}$, H$_{pyridazine}$); 8.54 (d, 2H, J=8.7, H$_{pyridazine}$); 8.64 (d, 2H, J=8.1, H$_{pyridine}$); 8.69-8.72 (m, 2H, H$_{pyridine}$).

$^{13}$C NMR (CDCl$_3$) δppm: 121.49, 124.86, 124.98, 129.83, 137.15, 149.44, 152.80, 157.27, 159.79.

MS, m/z (I %): 344 (M$^+$, 54%), 316 (M$^+$-N$_2$, 6%), 266 (M$^+$-Py, 100%), 78 (Py$^+$, 52%).

HRMS
Exact mass calculated [M+H]=345.0922
Exact mass found [M+H]=345.0919

Example 24

6,6'-dimethoxy-3,3'-bipyridazine 15

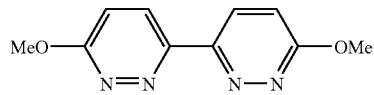

C$_{10}$H$_{10}$N$_4$O$_2$
M = 218.21
Yield = 96%
White powder

In a 100 ml two-necked flask, 1.55 g (2.1 mmol) of dichlorobis(triphenylphosphine)nickel(II), 452 mg (6.95 mmol) of zinc and 2.23 g (6.95 mmol) of tetrabutylammonium bromide are solubilized in 40 ml of freshly distilled DMF. After degassing, the solution is stirred at ambient temperature for 30 min (the green starting solution turns brown). 1 g (6.95 mmol) of 3-chloro-6-methoxypyridazine 14 is added to this solution, and the reaction mixture is heated at 55° C. for 8 hours. After the solvent has been evaporated off under reduced pressure, the residue is taken up in a saturated solution of ammonium chloride, the suspension is extracted with 4×40 ml of dichloromethane and the organic phase is dried over MgSO$_4$ and then concentrated under reduced pressure. The reaction crude is chromatographed on silica gel (eluent:ethyl acetate/petroleum ether=4/6), to give the bipyridazine 15 with a yield of 96%.

$^1$H NMR (CDCl$_3$) δppm: 4.16 (s, 6H, OCH$_3$); 7.10 (d, 2H, J=9.3, H$_{pyridazine}$); 8.59 (d, 2H, J=9.3, H$_{pyridazine}$).

$^{13}$C NMR (CDCl$_3$) δppm: 54.96, 118.07, 127.25, 152.40, 165.35.

MS, m/z (I %): 218 (M$^+$, 100%), 189 (M$^+$-N$_2$, 22%), 175 (M$^+$-(N$_2$+CH$_3$), 31%).

Example 25

6,6'-(2,2'-H)-bipyridazine-3,3'-dione 16

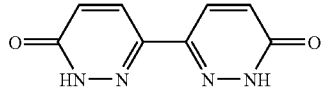

C$_8$H$_6$N$_4$O$_2$
M = 190.16
Yield = 97%
White powder

In a 100 ml round-bottomed flask, 1 g (4.58 mmol) of 6,6'-dimethoxy-3,3'-bipyridazine 15 is dissolved in 5 ml of a solution of HBr at 33% in acetic acid. The reaction mixture is brought to reflux for 48 h. After the solvent has been evaporated off, the solid is washed with acetone, suspended in 15 ml of water, and neutralized at boiling with a concentrated sodium hydroxide solution. After filtration and drying, the product 16 is obtained with a yield of 97%.

$^1$H NMR (TFA-d$_1$) δppm: 7.35 (d, 2H, J=9.9, H$_{pyridazine}$); 8.38 (d, 2H, J=9.9, H$_{pyridazine}$).

$^{13}$C NMR (TFA-d$_1$) δppm: 130.71, 134.58, 146.06, 166.29.

MS, m/z (I %): 190 (M$^+$, 100%), 175 (M$^+$-N$_2$, 57%).

Example 26

6,6'-dichloro-3,3'-bipyridazine 17

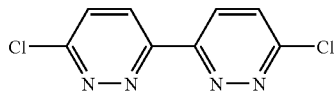

C$_8$H$_4$Cl$_2$N$_4$
M = 227.05
Yield = 95%
Yellowish powder

In a 250 ml round-bottomed flask, 4 g (21.05 mmol) of bipyridazinedione 16 in solution in 40 ml of phosphorus oxychloride are refluxed for 18 hours. The reaction mixture is poured into 250 ml of ice-cold water and then neutralized, dropwise, with a saturated aqueous solution of NaHCO$_3$. After extraction with dichloromethane, the organic phase is dried over MgSO$_4$ and then concentrated under reduced pressure, to give the dichlorobispyridazine 17 with a yield of 95%.

$^1$H NMR (CDCl$_3$) δppm: 7.73 (d, 2H, J=8.7, H$_{pyridazine}$); 8.77 (d, 2H, J=8.7, H$_{pyridazine}$).

$^{13}$C NMR (CDCl$_3$) δppm: 126.98, 127.68, 129.22, 130.80.

MS, m/z (I %): 228 (M$^+$+1, 27%), 227 (M$^+$, 8%), 226 (M$^+$−1, 41%) 163 (M$^+$−(N$_2$+Cl), 100%).

Example 27

6,6'-bis(pyridin-2-yl)-3,3'-bipyridazine 19

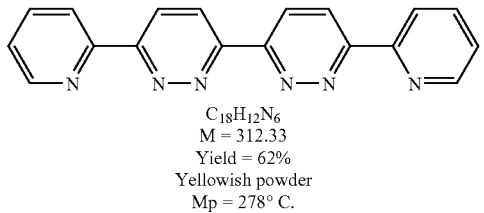 [SMILES: c1ccc(-c2ccc(-c3ccc(-c4ccccn4)nn3)nn2)nc1]

C$_{18}$H$_{12}$N$_6$
M = 312.33
Yield = 62%
Yellowish powder
Mp = 278° C.

The 6,6'-bis(pyridin-2-yl)-3,3'-bipyridazine 19 was prepared according to the general Stille coupling procedure, starting from a reaction mixture of 500 mg (4.42 mmol) of dichlorobipyridazine 17, 2.03 g (5.52 mmol) of 6-tributylstannylpyridine 18 and 387 mg (0.55 mmol) of dichlorobis(triphenylphosphine)-palladium(II), in 40 ml of DMF. The reaction mixture is heated at 95° C. for 24 h. The residue obtained is purified by silica gel chromatography (eluent: ethyl acetate/petroleum ether=1/9). The disubstituted product 19 is isolated with a yield of 62%.

$^1$H NMR (CDCl$_3$) δppm: 7.45 (m, 2H, H$_{pyridine}$); 7.94 (dt, J=1.8, 7.2, 2H, H$_{pyridine}$); 8.79 (m, 6H, 2H$_{pyridazine}$, 4H$_{pyridine}$); 8.80 (d, J=9.0, 2H, H$_{pyridazine}$); 9.01 (d, J=9.0, 2H, H$_{pyridazine}$).

$^{13}$C NMR (CDCl$_3$) δppm: 121.78, 125.03, 125.41, 125.46, 137.25, 149.62, 153.08, 156.02, 159.17.

MS, m/z (I %): 312 (M$^+$, 100%), 284 (M$^+$−N$_2$, 54%), 255 (M$^+$−2N$_2$, 55%), 91 (PyCH$^+$, 89%).

HRMS

Exact mass calculated [M+Na]=335.1021

Exact mass found [M+Na]=335.1029

Example 28

6-methyl-2-tributylstannylpyridine 22

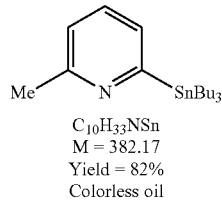

C$_{10}$H$_{33}$NSn
M = 382.17
Yield = 82%
Colorless oil

In a Schlenk tube at −10° C., 1.7 ml (2.6 mmol) of butyllithium (1.5M in hexane) are added, dropwise, to a solution of 0.4 ml (2.6 mmol) of freshly distilled diisopropylamine in anhydrous THF (50 ml). After 5 min, 0.70 ml (2.6 mmol) of tributyltin hydride is added. The stirring is maintained for 30 min at 0° C. A pale green solution of tributylstannyllithium is obtained, which solution will be cooled to −78° C. before adding, dropwise, 294.5 μl (2.6 mmol) of 2-bromo-6-methylpyridine. The mixture is kept at −78° C. for two hours. After a return to ambient temperature, the solvent is evaporated off under vacuum. The residue is taken up with dichloromethane and then washed with water. The organic phase is dried over MgSO$_4$, and evaporated to dryness. The product is purified by chromatography on an alumina column (eluent: ethyl acetate/petroleum ether=0.5/9.5), the stannylated pyridine 22 being isolated in the form of a yellow oil, with a yield of 82%.

$^1$H NMR (CDCl$_3$) δppm: 0.86-0.91 (m, 9H, CH3); 1.07-1.12 (m, 12H, CH2); 1.28-1.36 (m, 12H, CH2); 1.44-1.59 (m, 12H, CH2); 2.54 (s, 3H, CH$_3$); 6.95 (d, 1H, J=7.8, H$_{pyridine}$); 7.18 (d, 1H, J=7.5, H$_{pyridine}$); (t, 1H, J=7.5, H$_{pyridine}$).

$^{13}$C NMR (CDCl$_3$) δppm: 13.58, 13.67, 27.30, 27.81, 29.04, 120.63, 121.46, 129.32, 133.23, 158.53.

Example 29

6,6'-di(1-ethoxyvinyl)-3,3'-bipyridazine 24

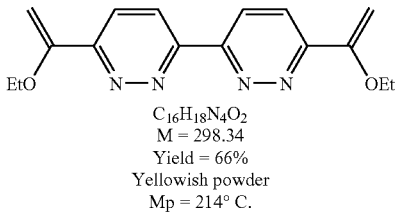 [SMILES: C=C(OCC)c1ccc(-c2ccc(C(=C)OCC)nn2)nn1]

C$_{16}$H$_{18}$N$_4$O$_2$
M = 298.34
Yield = 66%
Yellowish powder
Mp = 214° C.

500 mg (2.21 mmol) of dichlorobipyridazine, 1.591 g (4.42 mmol) of 1-(ethoxyvinyl)tri(n-butyl)tin, 77.4 mg (0.11 mmol) of dichlorobis(triphenylphosphine)-palladium(II) and 50 ml of freshly distilled DMF are introduced into a 100 ml round-bottomed flask equipped with a magnetic stirrer and with a condenser. The reaction medium is stirred at reflux for 24 h. After cooling to ambient temperature, the reaction medium is diluted with 80 ml of dichloromethane, then poured into a saturated solution of KF, and after filtration, the filtrate is washed with a saturated aqueous solution of NaHCO$_3$ and the organic phase is dried over MgSO$_4$ and concentrated under reduced pressure. The residue obtained is chromatographed on silica gel (eluent: a mixture of ethyl acetate/petroleum ether (20/80)). 6,6'-Di(1-ethoxyvinyl)-3, 3'-bipyridazine (18) is isolated with a yield of 66%.

$^1$H NMR (CDCl$_3$) δppm: δ1.47 (t, 6H, J=6.9 Hz, CH$_3$); 4.03 (q, 4H, J=6.9 Hz, OCH$_2$); 4.57 (d, 2H, J=2.4 Hz, H$_{vinyl}$); 5.85 (d, 2H, J=2.1 HZ, H$_{vinyle}$); 8.00 (d, 2H, J=9.0 Hz, H$_{pyridazine}$); 8.81 (d, 2H, J=8.7 Hz, H$_{pyridazine}$).

Example 30

2,6-bis(3-chloropyridazin-6-yl)pyridine 32

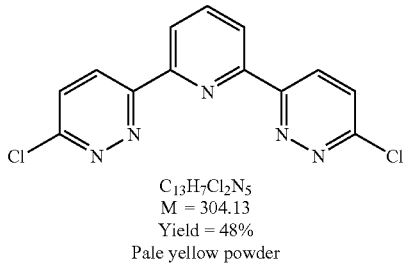

C$_{13}$H$_7$Cl$_2$N$_5$
M = 304.13
Yield = 48%
Pale yellow powder

This compound is obtained in the form of a brownish powder, according to procedure C, from the 6,6'-(pyridin-2,6-diyl)dipyridazin-3(2H)-one 36 (1.9 g, 6.247 mmol) and POCl$_3$ (15 ml). The residue is purified by silica column chromatography (EtOAc) to give the desired product with a yield of 48%.

$^1$H NMR (CDCl$_3$) δ(ppm): 7.67 (d, J=9.0, 2H, H$_{pyridazine}$), 8.10 (t, J=7.9, 1H, H$_{pyridine}$), 8.62 (d, J=9.0, 2H, H$_{pyridazine}$), 8.77 (d, J=7.9, 2H, H$_{pyridine}$).

$^{13}$C NMR (CDCl$_3$) δ (ppm): 122.9, 126.7, 128.7, 138.8, 152.3, 157.2, 157.4.

MS, m/z (I %): 303 (M$^+$, 17%); 240 (M$^+$−(Cl+N$_2$), 100%), 205 (M$^+$−(2Cl+N$_2$), 9%).

Example 31

2,6-bis[6-(pyridin-2-yl)pyridazin-3-yl]-pyridine 33

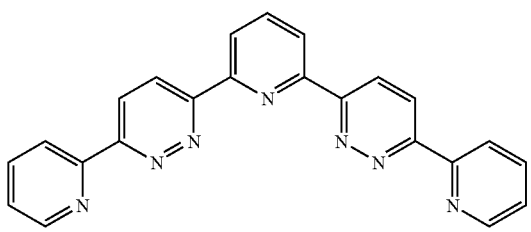

C$_{23}$H$_{15}$N$_7$
389.41
Yield = 17%
Pale yellow powder

This compound is synthesized according to procedure E, from the 2,6-bis(6-chloropyridazin-3-yl)pyridine 32 (0.50 g, 1.65 mmol), 2-bromopyridine (0.537 g, 4.13 mmol), zinc chloride (0.69 g, 4.13 mmol), butyllithium (2.5 M in hexane, 3.6 ml, 4.13 mmol), tetrakis(triphenylphosphine)palladium (0) (0.19 g, 0.165 mmol) and THF (80 ml). Silica chromatography (PE/EtOAc: gradient of 80/20 to 0/100) gives the pure product in the form of a pale yellow powder with a yield of 17%.

$^1$H NMR (CDCl$_3$) δ(ppm): 7.41 (ddd, J=7.5, 4.8, 1.2, 2H, H$_{pyridine}$ 7.90 (dt, J=7.8, 1.8, 2H, H$_{pyridine}$),) 8.10 (t, J=8.1, 1H, H$_{pyridine}$), 8.71-8.88 (m, 10H, 4H$_{pyridazine}$, 6H$_{pyridine}$).

$^{13}$C NMR (CDCl$_3$) δ (ppm): 121.7, 122.6, 124.8, 125.1, 128.5, 137.2, 138.5, 149.5, 153.1, 153.3, 157.8, 158.3.

MS, m/z (I %): 389 (M$^+$, 46%), 361 (M$^+$−N$_2$, 64%), 128 (PyC$_4$H$_2^+$, 100%).

UV/fluorescence profiles (DCM): see FIG. 14.

Example 32

2,6-bis(3-oxo-2H-pyridazin-6-yl)pyridine 36

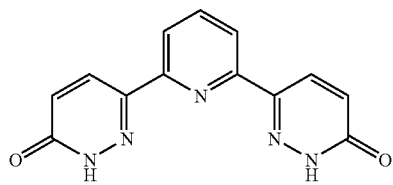

C$_{13}$H$_9$N$_5$O$_2$
M = 267.24
Yield = 75%
Yellow powder
Mp = 284° C.

In a 100 ml round-bottomed flask equipped with a condenser, 1.70 g (12.3 mmol) of K$_2$CO$_3$ and 1.13 g (12.26 mmol) of glyoxylic acid monohydrate are dissolved in 20 ml of water at 0° C. 1 g (6.13 mmol) of 2,6-diacetylpyridine 34 is added and the reaction mixture is stirred for 2.5 h at ambient temperature and is then again cooled in an ice bath. After the addition of 5.25 ml of acetic acid, dropwise, and 2.50 ml of hydrazine monohydrate, the mixture is brought to reflux for 2 h. After cooling to 0° C., K$_2$CO$_3$ is added until pH=7, and the solid precipitate obtained is filtered and then washed successively with water and with isopropanol. The pyridazinedione 36 is isolated with a yield of 75%.

$^1$H NMR (DMSO-d$_6$) δppm: 7.05 (d, 2H, J=9.9, H$_{pyridazine}$); 8.05-8.12 (m, 3H, H$_{pyridine}$); 8.52 (d, 2H, J=9.9, H$_{pyridazine}$), 11.38 (sl, 1H, NH).

$^{13}$C NMR (DMSO-d$_6$) δppm: 119.48, 129.94, 131.02, 138.82, 143.22, 151.39, 160.88.

MS, m/z (I %): 267 (M$^+$, 100%), 238 (M$^+$−N$_2$, 6%), 211 (M$^+$−2N$_2$, 32%).

Example 33

2,6-bis(3-pyridazinyl)pyridine 37

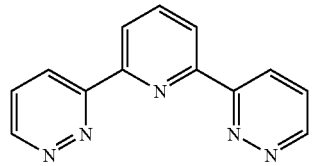

C$_{13}$H$_9$N$_5$
M = 235.24
Yield = 89%
Yellowish powder
Mp = 214° C.

500 mg (1.65 mmol) of 2,6-bis(3-chloropyridazin-6-yl)-pyridine 32 and 17.5 mg (0.08 mmol) of palladium-on-charcoal are dissolved in 50 ml of ethanol. The mixture is stirred at ambient temperature under a hydrogen pressure for 24 hours. The solution is filtered, evaporated under reduced pressure, and then chromatographed on silica gel (eluent: ethyl acetate/petroleum ether: 8/2). The 2,6-bis(3'-pyridazinyl)pyridine 37 is isolated with a yield of 89%.

$^1$H NMR (CDCl$_3$) δppm: 7.65 (dd, J=4.8, 8.7, 2H, H$_{pyridazine}$); 8.10 (t, J=8.1, 1H, H$_{pyridine}$); 8.68 (dd, J=1.8, 8.4, 2H, H$_{pyridazine}$); 8.81 (d, J=7.5, 2H, H$_{pyridine}$); 9.25. (dd, J=1.5, 4.8, 2H H$_{pyridazine}$).

$^{13}$C NMR (CDCl$_3$) δppm: 122.66, 124.40, 127.03, 138.59, 151.34, 153.13, 158.35.

MS, m/z (I %): 235 (M$^+$, 49%), 207 (M$^+$−N$_2$, 100%), 179 (M$^+$−2N$_2$, 9%).

HRMS
Exact mass calculated [M+H]=236.0936
Exact mass found [M+H]=236.0920

Example 34

6-(pyridin-2-yl)-3-(tributylstannyl)-pyridazine 39

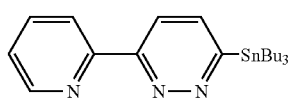

C$_{21}$H$_{33}$N$_3$Sn
M = 446.22
Yield = 76%
Yellow oil

In a Schlenk tube surmounted by a condenser, 1 g (5.24 mmol) of chloropyridazine 8a and 190 mg (0.79 mmol) of tetrakis(triphenylphosphine)palladium(0) are solubilized in 40 ml of freshly distilled DME. The medium is degassed while cold and under vacuum. After a return to ambient temperature, 3.04 g (5.24 mmol) of hexabutylditin are added. The solution is refluxed for 18 hours. The solvent is evaporated off under reduced pressure, and the residue is purified by chromatography on a neutral alumina gel (eluent: petroleum ether/ethyl acetate=95/5). The stannylated pyridazine 39 is obtained with a yield of 76%.

$^1$H NMR (CDCl$_3$) δppm: 0.84-0.92 (m, 9H, CH$_3$); 1.19-1.37 (m, 12H, CH$_2$); 1.56-1.62 (m, 6H, CH$_2$); 7.33-7.37 (m, 1H, H$_{pyridine}$); 7.63 (d, 1H, J=8.4, H$_{pyridazine}$); 7.84 (dt, 1H, J=1.8, 7.6, H$_{pyridine}$); 8.35 (d, 1H, J=8.4, H$_{pyridazine}$); 8.67-8.72 (m, 2H, 2H$_{pyridine}$).

$^{13}$C NMR (CDCl$_3$) δppm: 9.99, 13.52, 27.16, 28.87, 121.28, 121.36, 124.35, 134.12, 136.98, 149.15, 154.08, 156.38, 174.85.

Example 35

3-(6-bromopyridin-2-yl)-6-(pyridin-2-yl)-pyridazine 43

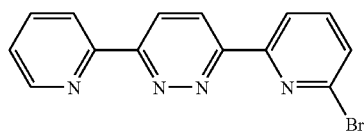

C$_{14}$H$_9$BrN$_4$
M = 313.15
Yield = 72%
White powder

The 3-(6-bromopyridin-2-yl)-6-(pyridin-2-yl)pyridazine was prepared according to the general Stille coupling method, starting from a mixture of 1.6 g (6.74 mmol) of 2,6-dibromobipyridine 42, 3 g (6.74 mmol) of 6-(pyridin-2-yl)-3-(tributylstannyl)pyridazine 39, 546 mg (0.47 mmol) of tetrakis(triphenylphosphine)-palladium(0) and 50 ml of freshly distilled toluene. The mixture is refluxed for 24 h. The residue obtained is chromatographed on a silica gel (eluent: ethyl acetate/petroleum ether=1/9). The brominated product 43 is isolated with a yield of 72%.

$^1$H NMR (CDCl$_3$) δppm: 7.40-7.44 (m, 1H, H$_{pyridine}$); 7.59 (dd, 1H, J=7.5, J=0.9, H$_{pyridine}$); 7.76 (t, 1H, J=7.5, H$_{pyridine}$); 7.88-7.94 (m, 1H, H$_{pyridine}$); 8.64-8.76 (m, 5H, 4H$_{pyridine}$, 1H$_{pyridazine}$).

$^{13}$C NMR (CDCl$_3$) δppm: 121.36, 121.90, 126.92, 124.97, 125.00, 125.48, 129.19, 133.12, 137.47, 139.50, 143.13, 149.36, 149.38.

MS, m/z (I %): 314 (M$^+$+2, 92%), 312 (M$^+$, 89%), 284 (M$^+$–N$_2$, 35%), 205 (M$^+$–(N$_2$+Br), 100%).

Example 36

3-(6-methylpyridin-2-yl)-6-(pyridin-2-yl)-pyridazine 44

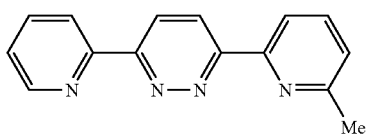

C$_{15}$H$_{12}$N$_4$
M = 248.28
Yield = 90%
White powder
Mp = 107° C.

The 3-(6-methylpyridin-2-yl)-6-(pyridin-2-yl)pyridazine 44 was prepared according to the general Stille coupling method, starting from a mixture of 2 g (5.23 mmol) of 6-methyl-2-tributylstannylpyridine 22, 666 mg (3.49 mmol) of 3-chloro-6-(pyridin-2-yl)pyridazine 8a, 208 mg (0.18 mmol) of tetrakis(triphenylphosphine)palladium(0) and 50 ml of freshly distilled toluene. The reaction medium is stirred at reflux for 18 h. The residue obtained is chromatographed on silica gel (eluent: ethyl acetate/petroleum ether=2/8). The coupling product 44 is isolated with a yield of 90%.

$^1$H NMR (CDCl$_3$) δ ppm: 2.62 (s, 3H, CH$_3$); 7.22 (d, 1H, J=7.8, H$_{pyridazine}$); 7.37 (ddd, 1H, J=0.9, 4.8, 7.5, H$_{pyridine}$); 7.76 (t, 1H, J=8.1, H$_{pyridine}$); 7.68 (dt, 1H, H$_{pyridine}$); 8.52 (d, 1H, J=7.8, H$_{pyridazine}$); 8.61-8.75 (m, 4H, 4H$_{pyridine}$).

$^{13}$C NMR (CDCl$_3$) δ ppm: 24.49, 118.69, 121.66, 124.34, 124.69, 124.99, 125.19, 137.21, 137.35, 149.33, 152.60, 153.42, 157.89, 158.27, 158.33.

MS, m/z (I %): 248 (M$^+$, 94%), 220 (M$^+$–N$_2$, 100%), 205 (M$^+$–(N$_2$+CH$_3$), 35%).

HRMS
Exact mass calculated [M+H]=249.1140
Exact mass found [M+H]=249.1141

Example 37

3-(2-carboxypyridin-6-yl)-6-(pyridin-2-yl)-pyridazine 45

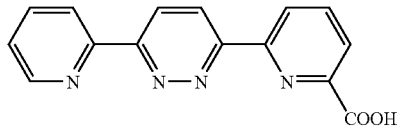

C$_{15}$H$_{10}$N$_4$O$_2$
M = 278.27
Yield = 74%
Orangey-red powder
Mp = 224° C.

400 mg (2.42 mmol) of pyridazine 44, 177 mg (1.60 mmol) of selenium dioxide and 7 ml of o-dichlorobenzene are introduced into a 100 ml round-bottomed flask equipped with a condenser. The mixture is heated at 150° C. for 4 hours, and then cooled to ambient temperature. An excess of water is added to the precipitate formed, which is filtered off and washed with water. The solid obtained is dried, so as to give the acid 45 with a yield of 74%.

$^1$H NMR (DMSO-d$_6$) δppm: 7.59 (ddd, 1H, J=1.2, 4.8, 7.5, H$_{pyridine}$); 8.07 (dt, 1H, J=2.1, 8.1, H$_{pyridine}$); 8.1-8.3 (m, 2H, H$_{pyridine}$); 8.64 (d, 1H, J=8.4, H$_{pyridine}$); 8.72 (d, 1H, J=9.0, H$_{pyridazine}$); 8.79 (m, 1H, H$_{pyridine}$); 8.82-8.85 (m, 2H, H$_{pyridine}$, H$_{pyridazine}$); 9.71 (bs, 1H, COOH).

$^{13}$C NMR (DMSO-d$_6$) δppm: 121.1, 123.98, 125.09, 125.28, 125.48, 125.72, 137.65, 139.11, 148.32, 149.70, 152.53, 152.65, 157.12, 157.96, 165.64.

MS, m/z (I %): 279 (M$^+$, 39%), 278 (M$^+$–H, 100%), 250 (M$^+$–N$_2$, 32%), 205 (M$^+$–(N$_2$+COOH), 80%).

HRMS
Exact mass calculated [M]=278.0804
Exact mass found [M]=278.0781

Example 38

3,6-bis(6-methylpyridin-2-yl)pyridazine 47

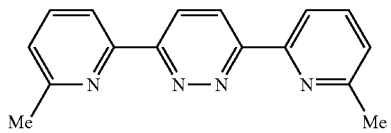

C$_{16}$H$_{14}$N$_4$
M = 262.31
Yield = 52%
Yellowish crystals
Mp = 141° C.

The 3,6-bis(6-methylpyridin-2-yl)pyridazine 47 is obtained according to the general Stille procedure, starting from a reaction mixture of 1.55 g (4.06 mmol) of 6-methyl-2-(tributylstannyl)pyridine 22, 300 mg (2.03 mmol) of 3,6-dichloropyridazine 46, 231 mg (0.20 mmol) of tetrakis(triphenylphosphine)palladium(0) and 50 ml of freshly distilled toluene. The reaction medium is stirred at reflux for 18 h and the residue obtained is purified by silica gel chromatography (eluent: ethyl acetate/petroleum ether=3/7). The disubstituted product 47 is isolated with a yield of 52%.

$^1$H NMR (CDCl$_3$) δppm: 2.65 (s, 6H, CH$_3$); 7.24 (d, J=6.3, 2H, H$_{pyridine}$); 7.77 (t, J=7.8, 2H, H$_{pyridine}$); 8.54 (d, J=8.7, 2H, H$_{pyridine}$); 8.68 (s, 2H, H$_{pyridazine}$).
$^{13}$C NMR (CDCl$_3$) δppm: 24.35, 118.60, 124.18, 124.96, 137.14, 137.22, 152.78, 158.17, 158.21.
MS, m/z (I %): 262 (M$^+$, 100%), 234 (M$^+$-N$_2$, 85%), 142 (M$^+$-(N$_2$+Py-CH$_3$), 48%).
HRMS
Exact mass calculated [M+H]=263.1297
Exact mass found [M+H]=263.1317

Example 39

3,6-bis(2-carboxypyridin-6-yl)pyridazine 48

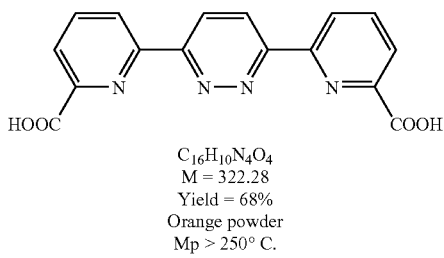 [SMILES: O=C(O)c1cccc(-c2ccc(-c3cccc(C(=O)O)n3)nn2)n1]

C$_{16}$H$_{10}$N$_4$O$_4$
M = 322.28
Yield = 68%
Orange powder
Mp > 250° C.

The diacid 48 is obtained according to a procedure similar to the preparation of the acid 45, from a mixture of 230 mg (0.88 mmol) of pyridazine 47, 126 mg (1.14 mmol) of selenium dioxide and 7 ml of o-dichlorobenzene. The mixture is heated at 150° C. for 12 hours, so as to give the diacid 48 with a yield of 68%.

$^1$H NMR (DMSO-d$_6$) δppm: 8.21-8.29 (m, 4H, H$_{pyridine}$); 8.82-8.85 (m, 2H, H$_{pyridine}$, H$_{pyridazine}$); 13.41 (1s, 2H, COOH).
$^{13}$C NMR (DMSO-d$_6$), δppm: 124.13, 125.53, 125.83, 139.15, 148.38, 152.64, 157.38, 165.64.
MS, m/z (I %): 322 (M$^+$, 100%), 294 (M$^+$-N$_2$, 41%), 278 (M$^+$-COOH, 47%).
HRMS
Exact mass calculated [M−H]=321.0624
Exact mass found [M−H]=321.0623

Example 40

2,6-bis[6-(6-methylpyridin-2-yl)pyridazin-3-yl)pyridine 49

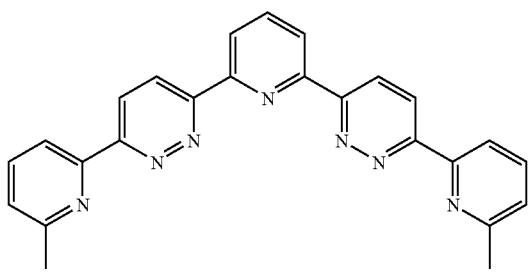

C$_{25}$H$_{19}$N$_7$
417.47
Yield = 73%
Pale yellow powder

This compound is synthesized according to procedure E, from the 2,6-bis(6-chloropyridazin-3-yl)pyridine 32 (0.50 g, 1.65 mmol), the 2-bromopicoline 104 (0.71 g, 4.13 mmol), zinc chloride (0.69 g, 4.13 mmol), butyllithium (2.5M in hexane, 3.6 ml, 4.13 mmol), tetrakis(triphenylphosphine)palladium(0) (0.19 g, 0.165 mmol) and THF (80 ml). Silica chromatography (PE/EtOAc: gradient of 80/20 to 0/100) gives the pure product in the form of a pale yellow powder with a yield of 73%.

$^1$H NMR (CDCl$_3$) δ(ppm): 2.66 (s, 6H, CH$_3$), 7.26 (d, J=7.8, 2H, H$_{pyridazine}$), 7.78 (t, J=7.5, 2H, H$_{pyridine}$), 8.10 (t, J=7.7, 1H, H$_{pyridine}$), 8.56 (d, J=7.9, 2H, H$_{pyridazine}$), 8.77 (dd, J=8.9, 12.4, 4H, H$_{pyridine}$), 8.86 (d, J=7.2H, H$_{pyridine}$).
$^{13}$C NMR (CDCl$_3$) δ (ppm): 24.6, 118.7, 122.5, 124.4, 124.9, 125.2, 137.3, 138.4, 152.6, 153.2, 157.7, 158.4, 158.6.
MS, m/z (I %): 417 (M$^+$, 100%), 389 (M$^{+4}$-N$_2$, 94%).
UV/fluorescence (DCM): see FIG. 12.

Example 41

2,6-bis[3-(2-carboxypyridin-6-yl)pyridazin-6-yl]pyridine 50

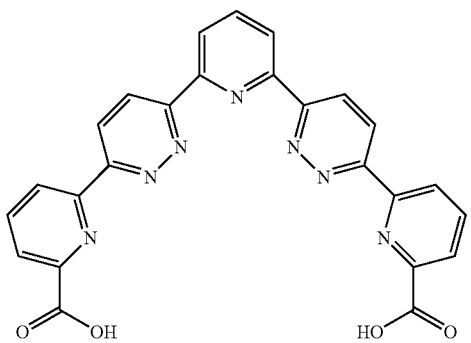

C$_{25}$H$_{15}$N$_7$O$_4$
M = 477.43
Yield = 71%
Orange powder
Mp = 251° C.

The diacid 50 is obtained according to the procedure used for preparing the acid (48), from a mixture of 300 mg (0.72 mmol) of pyridazine 49, 104 mg (0.93 mmol) of selenium dioxide and 10 ml of o-dichlorobenzene. The solution is heated at 150° C. for 18 hours with stirring, and the acid 50 is isolated with a yield of 71%.

$^1$H NMR (TFA-d$_1$) δppm: 8.40-8.51 (m, 3H, H$_{pyridine}$); 8.63 (d, 2H, J=7.8, H$_{pyridine}$); 8.84 (m, 4H, H$_{pyridine}$); 9.57 (d, 2H, J=9.0, H$_{pyridazine}$); 9.63 (d, 2H, J=9.0, H$_{pyridazine}$).

$^{13}$C NMR (TFA-d$_1$) δppm: 126.23, 126.70, 127.45, 127.47, 129.60, 130.69, 143.42, 143.47, 145.94, 147.25, 148.98, 151.39, 153.58.

MS, m/z (I %): 477 (M$^+$, 7%), 389 (M$^+$−2COOH, 88%), 361 (M$^+$−(2COOH+N$_2$), 100%).

HRMS

Exact mass calculated [M+H]=476.1107

Exact mass found [M+H]=476.1092

Example 42

6,6'-dibromo-2,2'-bipyridine 52b

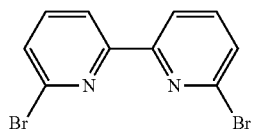

52b

C$_{10}$H$_6$Br$_2$N$_2$
338.00
Yield = 55%
White powder

In a three-necked round-bottomed flask, the 2,6-dibromopyridine (42) (2.32 g, 10 mmol) is solubilized in 250 ml of diethyl ether cooled to −78° C. The assembly is equipped with a solids-addition funnel containing copper chloride (2) (pre-dried, 2 g, 14.9 mmol). Butyllithium (2.4M in hexane, 4.6 ml, 11 mmol) is added dropwise and the reaction medium is stirred for 2 hours at −78° C. The copper chloride is added slowly over 30 minutes and the mixture is stirred for a further 30 minutes at −78° C. Dry oxygen bubbling is carried out for 1 hour at −78° C. and then for 1 hour at ambient temperature. The reaction medium is treated with 200 ml of water and 50 ml of a 1M solution of HCl, and a precipitate appears. The solution is filtered and the resulting solid is recrystallized from THF. The brownish solid is subsequently solubilized in THF and filtered through a Millipore filter. The solution is concentrated under vacuum and the desired product is obtained in the form of a white powder with a yield of 79%.

$^1$H NMR (CDCl$_3$) δ(ppm): 7.50 (dd, J=0.6, 8.1, 2H, H$_{pyridine}$), 7.66 (t, J=7.8, 2H, H$_{pyridine}$), 8.37 (dd, J=0.6, 8.4, 2H, H$_{pyridine}$).

$^{13}$C NMR (CDCl$_3$) δ (ppm): 119.71, 128.15, 138.86, 141.15, 155.16.

MS, m/z (I %): 314 (M$^+$+2, 100%), 312 (M$^+$, 45%), 233 (M$^+$−Hr, 54%), 153 (M$^+$−2Br, 32%).

Example 43

6,6'-dimethoxy-2,2'-bipyridine 58

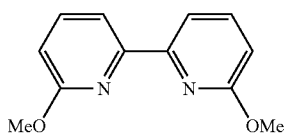

C$_{12}$H$_{12}$N$_2$O$_2$
M = 216.24
Yield = 94%
White powder

The synthesis of the bipyridine 58 is carried out according to the procedure used for preparing the bipyridazinone 15, by preparing a catalytic mixture of 7.77 g (10.5 mmol) of dichlorobis(triphenylphosphine)-nickel(II), 2.27 g (35 mmol) of zinc and 11.235 g (35 mmol) of tetrabutylammonium bromide in 100 ml of DMF for coupling 5 g (35 mmol) of 2-chloro-6-methoxypyridine 57 (12 hours). The bipyridine 58 was isolated with a yield of 94%.

$^1$H NMR (CDCl$_3$) δppm; 4.03 (s, 6H, OCH$_3$); 6.75 (d, 2H, J=8.4, H$_{pyridine}$); 8.01. (d, 2H, J=7.2, H$_{pyridine}$); 7.68 (t, 2H, J=7.8, H$_{pyridine}$).

$^{13}$C NMR (CDCl$_3$) δppm: 53.07, 110.76, 113.50, 139.10, 153.28, 163.26.

MS, m/z (I %); 216 (M$^+$, 93%) 215 (M$^+$−1, 100%), 185 (M$^+$−OMe, 45%).

Example 44

6,6'-(1,1'H)-bipyridine-2,2'-dione 59

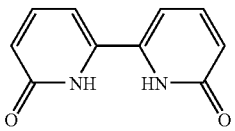

C$_{10}$H$_8$N$_2$O$_2$
M = 188.18
Yield = 94%
White powder

Applying the same hydrolysis procedure used during the preparation of bipyridazinedione 16, 1 g (5.32 mmol) of 6,6'-dimethoxy-3,3'-bipyridine (12) is dissolved in 5 ml of a solution of HBr at 33% in acetic acid. The reaction mixture is brought to reflux for 48 h. After treatment, the product 59 is obtained with a yield of 94%.

$^1$H NMR (TFA-d$_1$) δppm: 7.18 (d, 2H, J=9.0, H$_{pyridine}$); 7.39 (d, 2H, J=7.8, H$_{pyridine}$); 8.04 (t, 2H, J=8.7, H$_{pyridine}$).

$^{13}$C NMR (TFA-d$_1$) δppm: 114.64, 121.30, 139.89, 148.90, 166.19.

MS, m/z (I %): 188 (M$^+$, 100%), 160 (M$^+$−CO, 39%), 132 (M$^+$−2CO, 39%).

Example 45

6,6'-bis(tributylstannyl)-2,2'-bipyridine 60

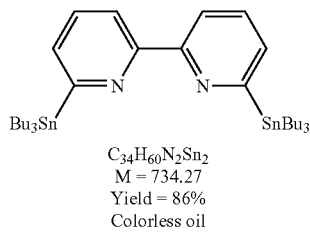

C$_{34}$H$_{60}$N$_2$Sn$_2$
M = 734.27
Yield = 86%
Colorless oil

In a Schlenk tube equipped with a condenser, 817 mg (2.62 mmol) of 6,6'-dibromo-2,2'-bipyridazine 52b and 190 mg (0.787 mmol) of tetrakis(triphenylphosphine)-palladium(0) are solubilized in 30 ml of freshly distilled DME. The medium is degassed while cold and under vacuum. After a return to ambient temperature, 3.04 g (5.24 mmol) of hexabutylditin are added. The solution is refluxed for 24 hours. The solvent is evaporated off under reduced pressure, and the residue is purified by chromatography on a neutral alumina gel (eluent: petroleum ether/ethyl acetate=95/5). The stannylated bipyridine 60 is obtained with a yield of 86%.

$^1$H NMR (CDCl$_3$) δppm: 0.90 (t, 18H, J=7.2, CH$_3$); 1.13-1.19 (m, 12H, CH$_2$); 1.34-1.41 (m, 12H, CH$_2$); 1.61-1.66 (m, 12H, CH$_2$); 7.38 (dd, 2H, J=1.2, 7.2; H$_{pyridine}$); 7.62 (t, 2H, J=7.5, H$_{pyridine}$); 8.37 (dd, 2H, J=1.2, 8.1 HZ; H$_{pyridine}$).

$^{13}$C NMR (CDCl$_3$) δppm: 10.03, 13.73, 27.38, 29.14, 119.30, 131.97, 133.86, 156.75, 172.75.

Example 46

6,6'-bis[6-(pyridin-2-yl)pyridazin-3-yl]-2,2'-bipyridine 61

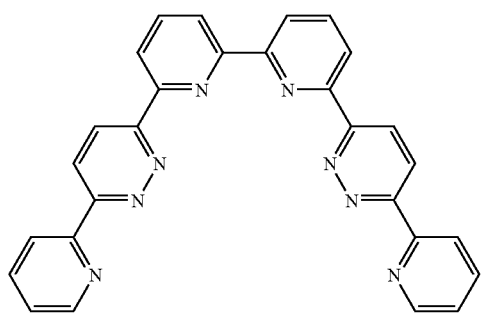 [SMILES: c1ccc(-c2ccc(-c3cccc(-c4cccc(-c5ccc(-c6ccccn6)nn5)n4)n3)nn2)nc1]

C$_{28}$H$_{18}$N$_8$
M = 466.50
Yield = 68%
Pinkish-brown powder
Mp > 260° C.

The 6,6'-bis[6-(pyridin-2-yl)pyridazin-3-yl]-2,2'-bipyridine 61 was prepared according to the general Stille coupling procedure, starting from a reaction mixture of 1.17 g (6.15 mmol) of chloropyridazine 8a, 1.50 g (2.05 mmol) of 6,6'-ditributylstannyl-2,2'-bipyridine 60, 238 mg (0.20 mmol) of tetrakis(triphenylphosphine)palladium(0) and 60 ml of freshly distilled toluene. The medium is brought to reflux for 36 h, and the residue obtained is purified by silica gel chromatography (eluent: ethyl acetate/petroleum ether=1/9). The disubstituted product 61 is isolated with a yield of 68%.

$^1$H NMR (TFA-d$_1$) δppm: 8.19-8.23 (m, 2H, H$_{pyridine}$); 8.69-8.83 (m, 10H, $^2$H$_{pyridazine}$; 8H$_{pyridine}$); 8.95-9.08 (m, 6H, 2H$_{pyridazine}$, 4H$_{pyridine}$).

$^{13}$C NMR (TFA-d1) δppm: 126.23, 126.70, 127.45, 127.47, 129.60, 130.69, 143.42, 143.47, 145.94, 147.25, 148.98, 151.39, 153.58.

MS, m/z (I %): 466 (M$^+$, 87%), 438 (M$^+$-N$_2$, 100%), 409 (M$^+$-2N$_2$, 18%).

HRMS

Exact mass calculated [M+Na]=489.1552

Exact mass found [M+Na]=489.1517

Example 47

3,6,7,9-tetrahydro-5H-[1,10]diazepino-[1,2,3,4-lmn][1,10]phenanthroline-3,9-diones 64

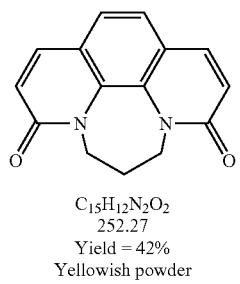

C$_{15}$H$_{12}$N$_2$O$_2$
252.27
Yield = 42%
Yellowish powder

The phenanthroline 62 (2.51 g, 13.9 mmol) is placed in a round-bottomed flask and is solubilized in the minimum amount of freshly distilled nitrobenzene. 1,3-Dibromopropane (6.3 ml, 61.9 mmol) is subsequently added to the solution. The medium is heated at 120° C. for 2 h, and the color of the solution changes from yellow to orange. After a return to ambient temperature, the precipitate formed is filtered off and washed with toluene, and recrystallized from a 5/1 mixture of ethanol/water. After filtration and drying, the bis-quaternary salt is isolated with a yield of 81%.

Potassium hexacyanoferrate (3) (11.6 g, 35.2 mmol), sodium hydroxide (5.33 g) and 30 ml of water are placed in a round-bottomed flask. The solution is cooled to 0° C. and the bis-quaternary salt (1.51 g, 3.9 mmol) solubilized in 50 ml of water is added dropwise while keeping the temperature of the medium below 5° C. for 2 hours. The mixture is neutralized under mild conditions with hydrochloric acid at low temperature, and extracted with DSM. The organic phase is dried over MgSO$_4$ and concentrated under vacuum. The residue is chromatographed on silica (DCM/MeOH: 95/5), and the desired product is obtained with a yield of 52%.

$^1$H NMR (CDCl$_3$) δ(ppm): 2.45 (q, J=6.5, 2H, CH$_2$), 4.32 (t, 4H, NCH$_2$), 6.79 (d, J=9.5, 2H, H$_{phenanthroline}$), 7.36 (s, 2H, H$_{phenanthroline}$) 7.72 (d, J=9.5, 2H, H$_{phenanthroline}$).

$^{13}$C NMR (CDCl$_3$) δ(ppm): 25.70, 45.71, 122.73, 123.10, 132.09, 138.81, 162.64.

Example 48

2,9-dibromo[1,10]phenanthroline 65b

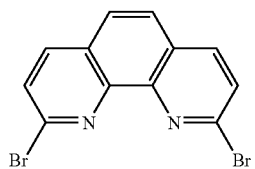

C₁₂H₆N₂O₂
338.00
Yield = 79%
Brownish powder

POBr₃ (5 g), PBr₃ (5 g) and the compound 64 (1 g) are added to a round-bottomed flask. The medium is refluxed for 18 hours. After a return to ambient temperature, the solution is poured into ice, neutralized with 1M sodium hydroxide and extracted with DSM. The organic phase is dried over Na₂SO₄ and concentrated under vacuum. The compound is obtained in the form of a brownish powder with a yield of 79%.

$^1$H NMR (CDCl₃) δ(ppm): 7.78 (d, J=8.4, 2H, H$_{phenanthroline}$), 7.81 (s, 2H, H$_{phenanthroline}$), 8.08 (d, J=8.4, 2H, H$_{phenanthroline}$).
$^{13}$C NMR (CDCl₃) δ (ppm): 126.51, 127.87, 128.51, 138.20, 143.04, 145.43.
MS, m/z (I %): 338 (M⁺, 100%), 259 (M⁺−Br, 60%), 180 (M⁺−Br₂, 85%).

Example 49

2,9-bis[6-(pyridin-2-yl)pyridazin-3-yl][1,10]phenanthroline 66

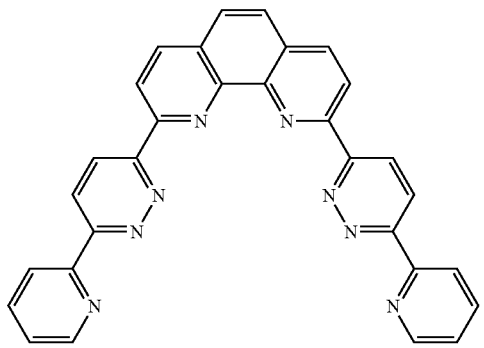 [SMILES: c1ccc(-c2ccc(-c3ccc4ccc5ccc(-c6ccc(-c7ccccn7)nn6)nc5c4n3)nn2)nc1]

C₃₀H₁₈N₈
M = 490.52
Yield = 91%
Light yellow powder
Mp > 270° C.

The 2,9-di[6-(pyridin-2-yl)pyridazin-3-yl]-1,10-phenanthroline 66 was prepared according to the general Stille coupling procedure, starting from a reaction mixture of 340 mg (1.10 mmol) of 1,10-dibromophenanthroline 65b, 1.35 g (3.03 mmol) of 3-pyridyl-6-tributylstannylpyridazine 39, 116 mg (0.10 mmol) of dichlorobis(triphenylphosphine)palladium(II) and 50 ml of freshly distilled DMF. The reaction medium is brought to reflux for 36 h. The residue obtained is purified by silica gel chromatography (eluent: ethyl acetate/petroleum ether=1/9). The disubstituted product 66 is isolated with a yield of 91%.

$^1$H NMR (CDCl₃) δppm: 7.50 (m, 2H, 2H$_{pyridine}$); 7.94 (m, 4H, H₅, H₆ 2H$_{pyridine}$); 8.51 (d, 2H, J=8.1, H$_{pyridazine}$); 8.79-8.84 (m, 4H, H$_{pyridine}$); 8.89 (d, 2H, J=9.3, H₃, H₈); 8.21 (d, 2H, J=8.4, H$_{pyridazine}$) 8.32 (d, 2H, J=8.4, H₄, H₄, H₇).
$^{13}$C NMR (CDCl₃) δppm: 121.12, 121.77, 124.85, 125.31, 126.06, 127.38, 129.75, 132.78, 137.19, 137.51, 137.56, 147.19, 149.56, 153.18, 158.21.
MS, m/z (I %): 490 (M⁺, 53%), 462 (M⁺−N₂, 100%), 433 (M⁺−2N₂, 15%), 384 (M⁺−(Py+N₂), 27%).
HRMS
Exact mass calculated [M+Na]=513.1552
Exact mass found [M+Na]=513.1586

Example 50

6,6'-(pyridine-2,6-diyl)dipyridazin-3(2H)-one 36

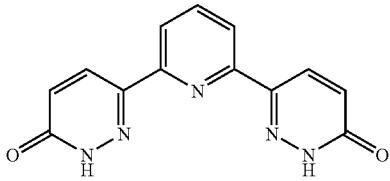

C₁₃H₉N₅O₂
M = 267.24
Yield = 91%
Pale yellow powder

In a round-bottomed flask surmounted by a condenser, cooled to 0° C., glyoxylic acid monohydrate (2.27 g, 30.67 mmol) is added to a solution of K₂CO₃ (6.83 g, 49.43 mmol) in 40 ml of water. When the medium becomes homogeneous, the 2,6-diacetylpyridine (34) (2 g, 12.26 mmol) is added and the solution is heated at 50° C. for 2 h 30. The medium is subsequently cooled to 0° C., and glacial acetic acid (10.5 ml) followed by hydrazine monohydrate (5 ml) are added dropwise. The solution is brought to reflux for 2 hours. The medium is subsequently cooled to 0° C. and neutralized with powdered K₂CO₃. The precipitate formed is filtered off, and washed with water and then with isopropanol. A pale yellow powder is obtained with a yield of 91%.

$^1$H NMR (DMSO-d6) δ(ppm): 7.05 (d, J=9.9, 2H, H$_{pyridazine}$), 8.05-8.12 (m, 3H, H$_{pyridine}$), 8.52 (d, J=9.9, 2H, H$_{pyridazine}$), 11.38 (bs, 1H, NH).
$^{13}$C NMR (DMSO-d6) δ (ppm): 119.5, 129.9, 131.0, 138.8, 143.2, 151.4, 160.9.
MS, m/z (I %): 267 (M⁺, 100%), 238 (M⁺−N₂, 6%), 211 (M⁺−2N₂, 32%).

Example 51

2,6-bis(5-(6-methylpyridin-2-yl)pyrrol-2-yl)pyridine 206

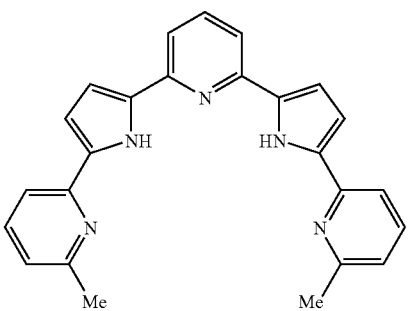

C₂₅H₂₁N₅
M = 391.47
Yield = 45%
Yellowish oil

This compound is obtained from the 2,6-bis(6-(6-methylpyridin-2-yl)pyridazin-3-yl)pyridine 49 with the THF/acetic buffer/CH$_3$CN: 5/4/1 solvent system (E=−1.2 V/SCE). The residue is purified by silica column chromatography (EtOAc), to give the desired product with a yield of 45%.

$^1$H NMR (CDCl$_3$) δ(ppm): 2.64 (s, 6H, CH$_3$), 6.78 (m, 4H, H$_{pyrrole}$), 6.91 (d, J=7.1, 2H, H$_{pyridine}$), 7.36 (d, J=7.8, 1H, H$_{pyridine}$), 7.45 (d, J=7.6, 2H, H$_{pyridine}$), 7.52 (d, J=7.5, 2H, H$_{pyridine}$), 7.58 (dt, J=0.8, 7.4, 1H, H$_{pyridine}$).

$^{13}$C NMR (CDCl$_3$) δ (ppm): 24.7, 108.9, 109.9, 115.6, 116.4, 120.4, 133.0, 133.9, 136.8, 136.9, 149.5, 150.1, 157.5

MS, m/z (I %): 392.1 (M+H$^+$, 100%).

UV/fluorescence profiles (DCM): see FIG. 13.

Example 52

Therapeutic activity of the compounds according to the invention

| Compound No. | Structure | KB cells | | Parasitology IC50 or 80 | | | | | |
|---|---|---|---|---|---|---|---|---|---|
| | | Cytotoxicity | | Leishmania mexicana | | Candida albicans | | Aspergillus fumigatus | |
| | | % inhibition at [10$^{-5}$] | IC50 μM | IC50 μg/mL | μM | μg/mL | μM | μg/mL | μM | μg/mL |
| 37 | *structure: dichloro-bis(pyridazinyl)pyridine* | 32 | | | | | | | | |
| 36 | *structure: bis(oxo-pyridazinyl)pyridine* | 95 | 2.6 | | 41 | 11 | >100 | >26.7 | | |
| 9 | *structure: bis(pyridinyl-pyridazinyl) ether* | 18 | 67 | 1.81 | >100 | >22.8 | >100 | >22.8 | >100 | >22.8 |
| 33 | *structure: bis(pyridinyl-pyridazinyl)pyridine* | 98 | 103 | 6.27 | 0.19 | 0.05 | 6.4 | 1.85 | IC80 = 32 | IC80 = 9.26 |

-continued

| Compound No. | Structure | KB cells Cytotoxicity | | Parasitology IC50 or 80 | | | | | |
|---|---|---|---|---|---|---|---|---|---|
| | | % inhibition at [10⁻⁵] | IC50 μM | IC50 μg/mL | Leishmania mexicana | | Candida albicans | | Aspergillus fumigatus | |
| | | | | | μM | μg/mL | μM | μg/mL | μM | μg/mL |
| 61 | | 80 | 4.5 | | <1 | <0.47 | 15 | 7 | | |
| 50 | | 49 | | | 8 | 3.8 | 63 | 30.1 | | |
| 11 | | 11 | | | 3 | 8.73 | 99 | 24.2 | | |

-continued

| Compound No. | Structure | KB cells Cytotoxicity | | Parasitology IC50 or 80 | | | |
|---|---|---|---|---|---|---|---|
| | | % inhibition at [10$^{-5}$] | IC50 μM IC50 μg/mL | Leishmania mexicana | | Candida albicans | Aspergillus fumigatus |
| | | | | μM | μg/mL | μM  μg/mL | μM  μg/mL |
| 66 | (structure) | 0 | | 16 | 7.84 | >100  49.1 | |

Antiparasitic Pharmaceutical Specialty Products:
Activity against *Leishmania mexicana* (IC50 μg/ml)

| Specialty product | promastigotes μg/ml | amastigotes μg/ml |
|---|---|---|
| Ketoconazole | 0.3 ± 0.5 | 1.3 ± 0.2 |
| Amphotericin B | 0.04 ± 0.03 | 0.47 ± 0.05 |
| Miltefosine | >2 | 1.42 ± 0.14 |

It will be noted that the IC50 values at the promastigote stage for the reference molecules given above are about 0.4 μg/ml for Amphotericin B, about 0.3 μg/ml for ketoconazole and greater than 2 μg/ml for miltefosine. However, the compounds of the invention have IC50 values of about 0.05 to 0.1 μg/ml.

Example 53

| | IC$_{50}$ of the referent molecules | | | | | |
|---|---|---|---|---|---|---|
| | Caco (colon) | | Sub7 (liver) | | Fibroblast (skin) | |
| IC$_{50}$ μM | 24 h | 48 h | 24 h | 48 h | 24 h | 48 H |
| Roscovitine standard | 6 | 3 | 10 | 4 | >25 | >25 |
| Taxol standard | 0.01 | <0.008 | 0.01 | <0.01 | >25 | >25 |
| Doxorubicine stand | 1 | 0.06 | 0.4 | 0.04 | 2 | 1 |
| 5FU standard means cells ± SD | 0.5* | 0.5* | >25 | >25 | >25 | >25 |
| Control DMSO | 06 ± 1 | 124 ± 10 | 120 ± 9 | 127 ± 5 | 114 ± 7 | 113 ± 6 |
| Control culture | 17 ± 1 | 120 ± 7 | 119 ± 5 | 128 ± 7 | 115 ± 4 | 115 ± 4 |

| | IC$_{50}$ of the referent molecules | | | | | | |
|---|---|---|---|---|---|---|---|
| | Caco (colon) | | Huh7 (liver) | | Fibroblast (skin) | | |
| IC$_{50}$ μM | 24 h | 48 h | 24 h | 48 h | 24 h | 48 h | comments |
| | | | | | | | ← |
| | 49 | 6 | 2 | >25 | | | ← |
| | | | | | >25 | | |
| | 50 | 10 | >25 | | | | ← |
| | 11 | 5 | 2 | 20 | | | |

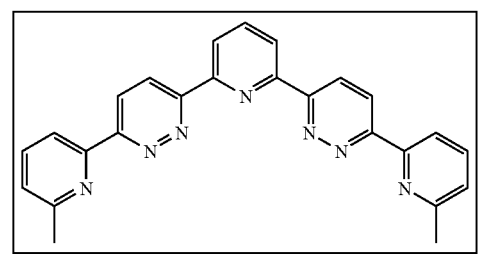 [SMILES: Cc1cccc(-c2ccc(-c3cccc(-c4ccc(-c5cccc(C)n5)nn4)n3)nn2)n1]

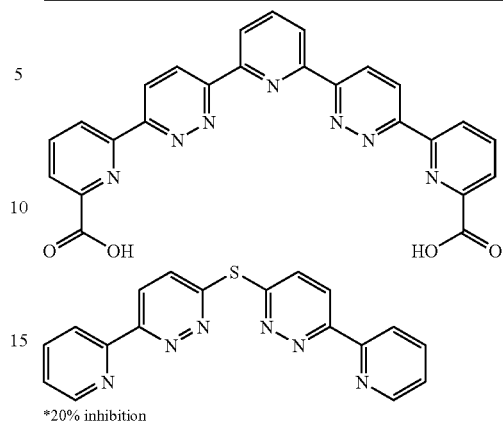

*20% inhibition

The invention claimed is:
1. A compound of formula

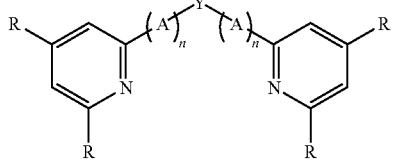
(Ia)

in which:
A is

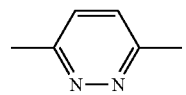

n is an integer equal to 1 or 2,
Y represents an oxygen atom, a sulfur atom, a methylene group, a hydroxymethylene group, a carbonyl group, a thiocarbonyl group,

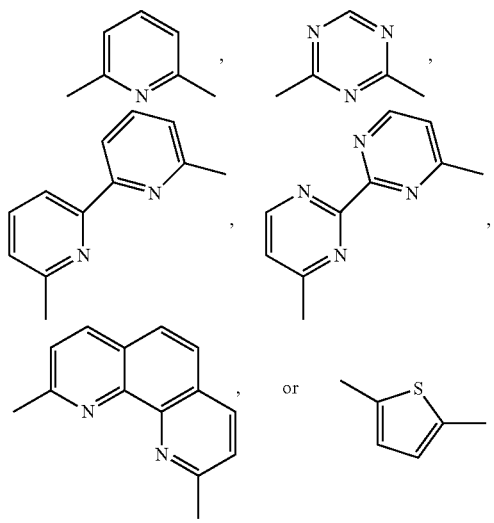

the groups R, which may be identical or different, represent a hydrogen, an alkyl, alkylamine, hydroxylalkyl or alkyloxy chain containing from 1 to 6 carbons, or a —COOH, —CONH$_2$, —COOR2 or —CONHR2 group in which R2 is an alkyl chain containing from 1 to 6 carbons, or, when the substituents R are identical in the 2-pyridinyl groups, the substituents R2 may together form an ethereal cyclic alkyl chain.

2. The compound of claim 1 wherein Y is

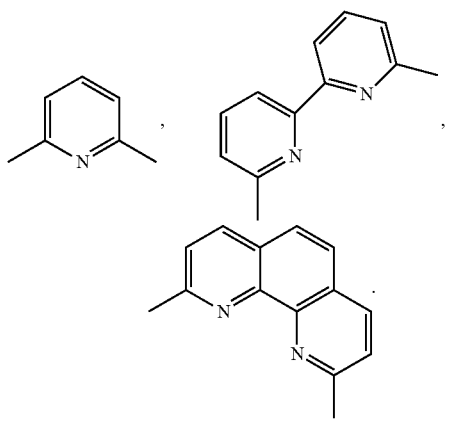

3. A compound selected from the group consisting of
di(6-pyridin-2-yl)pyridazine ether,
di(6-pyridin-2-yl)pyridazine thioether,
2,6-bis[6-(pyridin-2-yl)pyridazin-3-yl]pyridine,
2,6-bis[6-(6-methylpyridin-2-yl)pyridazin-3-yl]pyridine,
2,6-bis[3-(2-carboxypyridin-6-yl)pyridazin-6-yl]pyridine,
6,6'-bis[6-(pyridin-2-yl)pyridazin-3-yl]-2,2'-bipyridine,
2,9-bis[6-(pyridin-2-yl)pyridazin-3-yl]-1,10-phenanthroline,
2,6-bis[6-(6-methylpyridin-2-yl)pyridazin-3-yl]-2,2'-bipyridine, and
2,9-bis[6-(6-methylpyridin-2-yl)pyridazin-3-yl]-1,10-phenanthroline.

* * * * *